(12) United States Patent
Marcucci et al.

(10) Patent No.: US 11,918,553 B2
(45) Date of Patent: Mar. 5, 2024

(54) ANTI-ONCOGENIC PHYTOCHEMICALS COMPRISING SUBSTITUTED HENICOSANOIC ACID AND HENICOSENOIC ACID

(71) Applicant: Ostentus Therapeutics, Inc., Newport Coast, CA (US)

(72) Inventors: Guido Marcucci, Monrovia, CA (US); Antonio G. Cagnolo, Newport Beach, CA (US); Richard T. Nguyen, Covina, CA (US); William Graff, Newport Coast, CA (US)

(73) Assignee: Ostentus Therapeutics, Inc., Newport Coast, CA (US)

( * ) Notice: Subject to any disclaimer, the term of this patent is extended or adjusted under 35 U.S.C. 154(b) by 0 days.

(21) Appl. No.: 18/336,124

(22) Filed: Jun. 16, 2023

(65) Prior Publication Data
US 2024/0009163 A1 Jan. 11, 2024

Related U.S. Application Data

(63) Continuation of application No. 18/192,624, filed on Mar. 29, 2023.

(60) Provisional application No. 63/362,121, filed on Mar. 29, 2022.

(51) Int. Cl.
| | | |
|---|---|---|
| *A61K 31/185* | (2006.01) | |
| *A61K 31/20* | (2006.01) | |
| *A61K 36/28* | (2006.01) | |
| *A61P 1/00* | (2006.01) | |
| *A61P 1/18* | (2006.01) | |
| *A61P 11/00* | (2006.01) | |
| *A61P 15/08* | (2006.01) | |
| *A61P 35/00* | (2006.01) | |
| *A61P 35/02* | (2006.01) | |
| *A61P 35/04* | (2006.01) | |

(52) U.S. Cl.
CPC .............. *A61K 31/20* (2013.01); *A61K 36/28* (2013.01); *A61P 1/00* (2018.01); *A61P 1/18* (2018.01); *A61P 11/00* (2018.01); *A61P 15/08* (2018.01); *A61P 35/00* (2018.01); *A61P 35/02* (2018.01); *A61P 35/04* (2018.01); *A61K 2236/11* (2013.01); *A61K 2236/15* (2013.01); *A61K 2236/53* (2013.01)

(58) Field of Classification Search
CPC .................................................... A61K 31/185
USPC ............................................................ 514/715
See application file for complete search history.

(56) References Cited

U.S. PATENT DOCUMENTS

2023/0055105 A1    2/2023   Takemura et al.

FOREIGN PATENT DOCUMENTS

WO    WO-2023192918 A2 * 10/2023 ............. A61K 31/20

OTHER PUBLICATIONS

Pubchem, Compound Summary of 21-Hydroxyhenicosanoic Acid, CID 5282920 (2006).
WIPO, PCT Form USA 210 International Search Report for International Patent Application Serial No. PCT/US2023/065118, pp. 4 (dated Sep. 29, 2023).
WIPO, PCT Form USA 237 Written Opinion for International Patent Application Serial No. PCT/US2023/065118, pp. 9 (dated Sep. 29, 2023).

* cited by examiner

*Primary Examiner* — Douglas M Willis
(74) *Attorney, Agent, or Firm* — UltimatEdge IP Law Group, P.C.; Dean G. Stathakis

(57) ABSTRACT

The present specification discloses one or more anti-oncogenic phytochemicals comprising one or more compounds of chemical formula I:

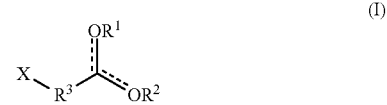

wherein $R^1$ is independently selected from H, $CH_3$ or $C_2H_5$ or is not present; $R^2$ is independently selected from H, $CH_3$ or $C_2H_5$ or is not present; provided that when $R^1$ is not present, $R^2$ is selected from H, $CH_3$ or $C_2H_5$ and when $R^2$ is not present $R^1$ is selected from H, $CH_3$ or $C_2H_5$: $R^3$ is a $C_{4-40}$ straight or branched chain, alkyl or alkylene and optionally substituted with one or more groups independently selected from $CH_3$, OH, SH, $NH_2$, OMe, OEt, N(H)Me and $NMe_2$; and X is independently selected from $CH_3$, OH, SH, $NH_2$, OMe, OEt, N(H)Me, and $NMe_2$, as well as, extracts, pharmaceutical compositions and medicaments comprising the one or more anti-oncogenic phytochemicals disclosed herein, methods of preparing such extracts, pharmaceutical compositions, and medicaments comprising the one or more anti-oncogenic phytochemicals, and methods and uses for treating a neoplasm or a cancer using one or more anti-oncogenic phytochemicals as well as extracts, pharmaceutical compositions and medicaments comprising one or more anti-oncogenic phytochemicals disclosed herein.

20 Claims, 33 Drawing Sheets

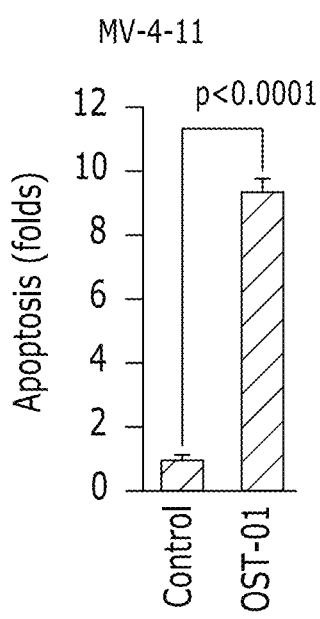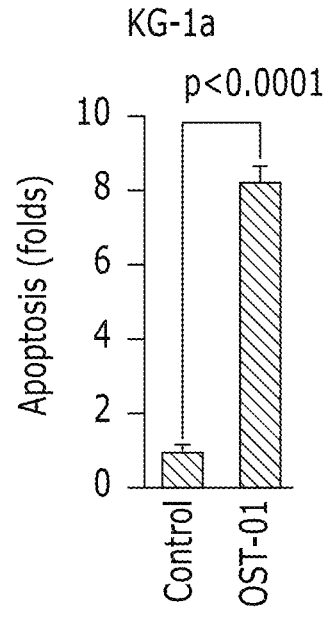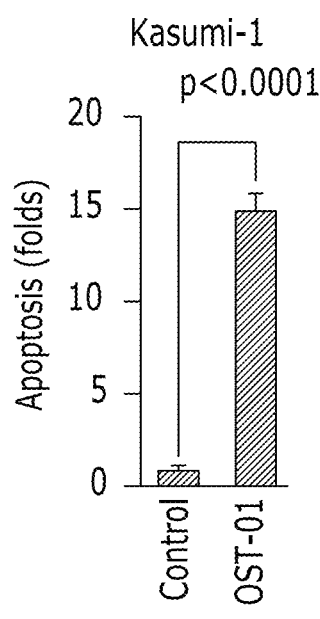
FIG. 3A  FIG. 3B  FIG. 3C
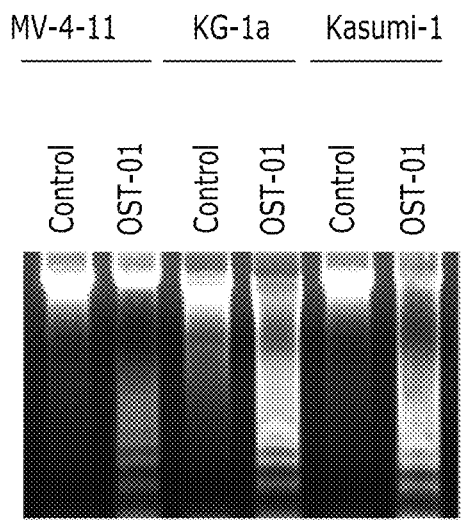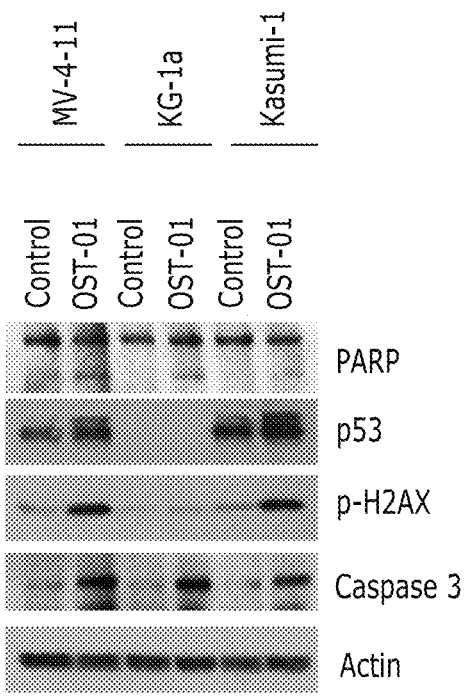
FIG. 4  FIG. 5

KG-1a

Kasumi-1

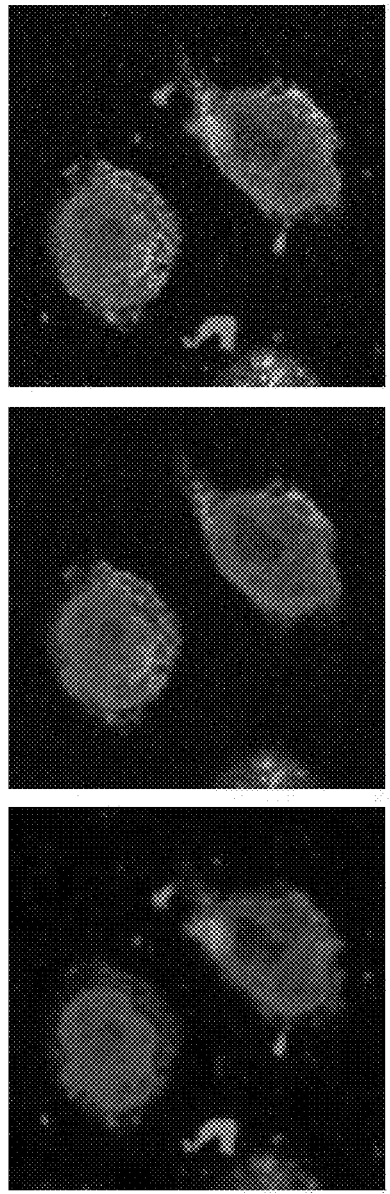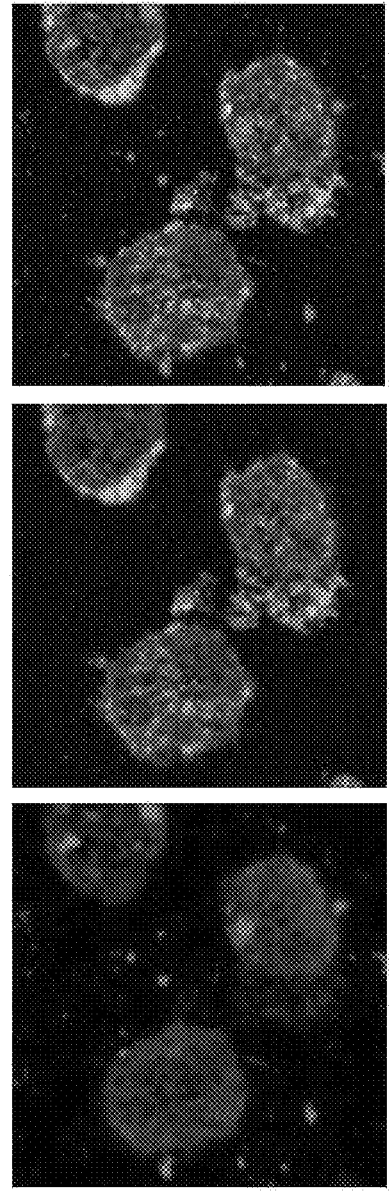

KG-1a

Kasumi-1

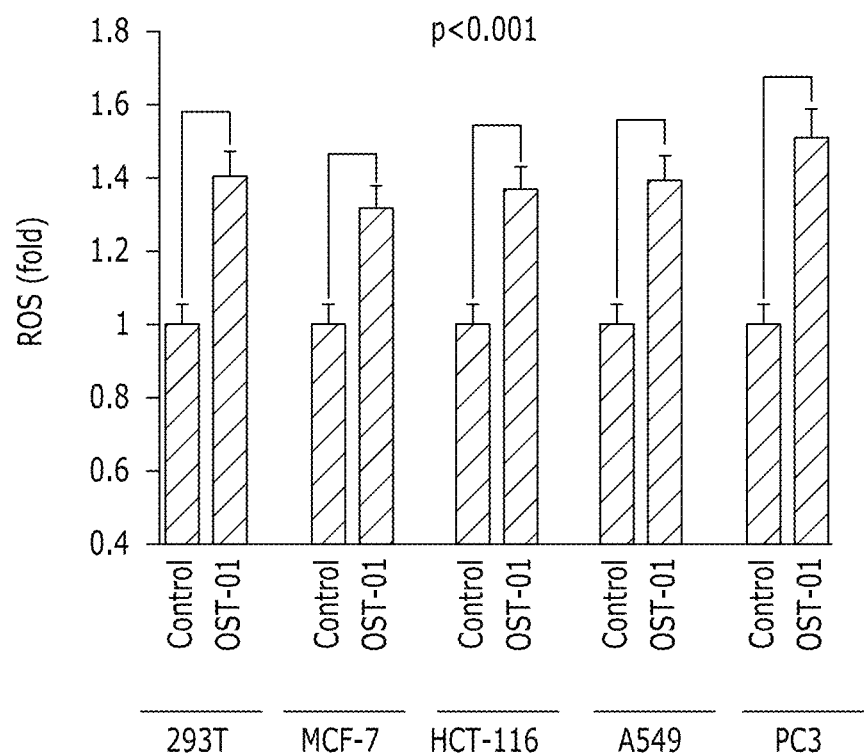
FIG. 16
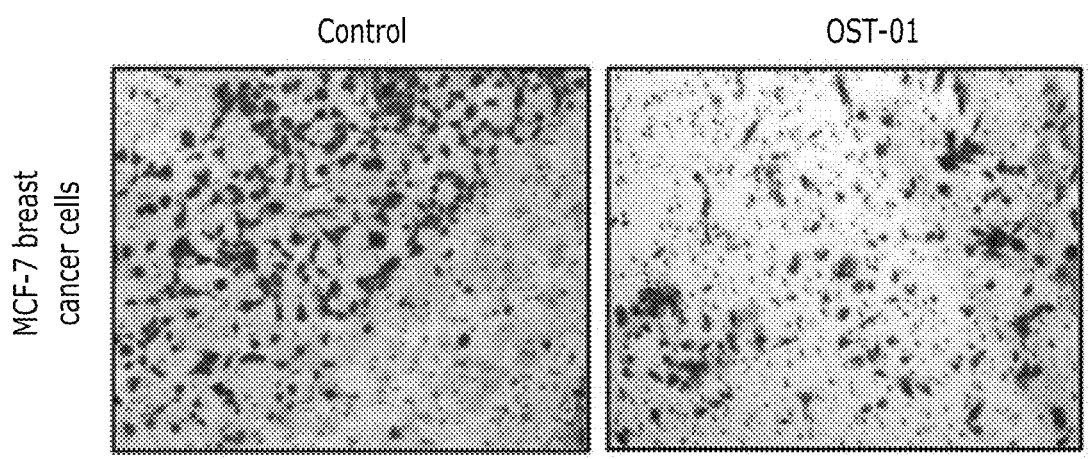
FIG. 17A                    FIG. 17B

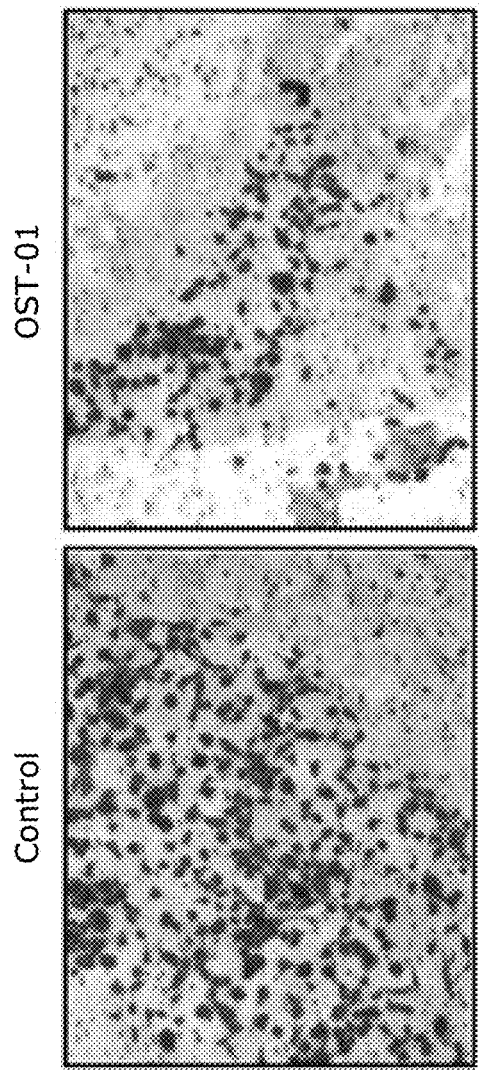
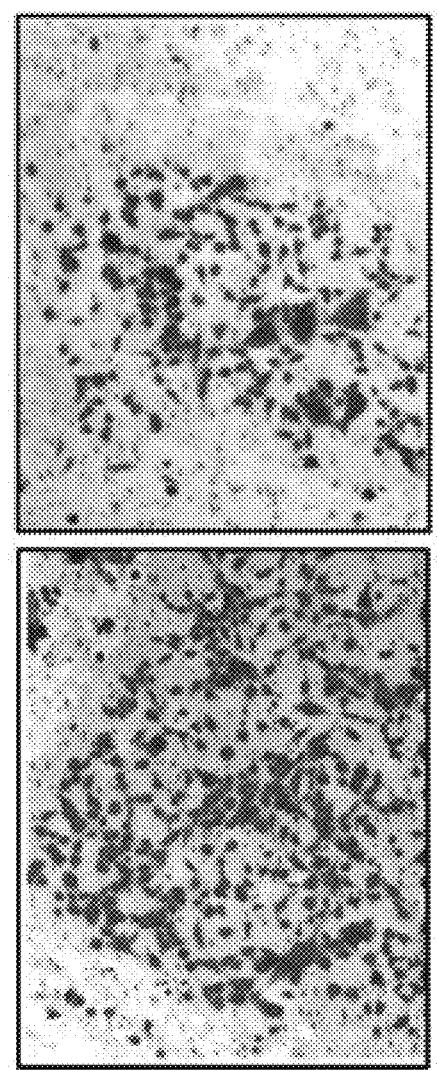

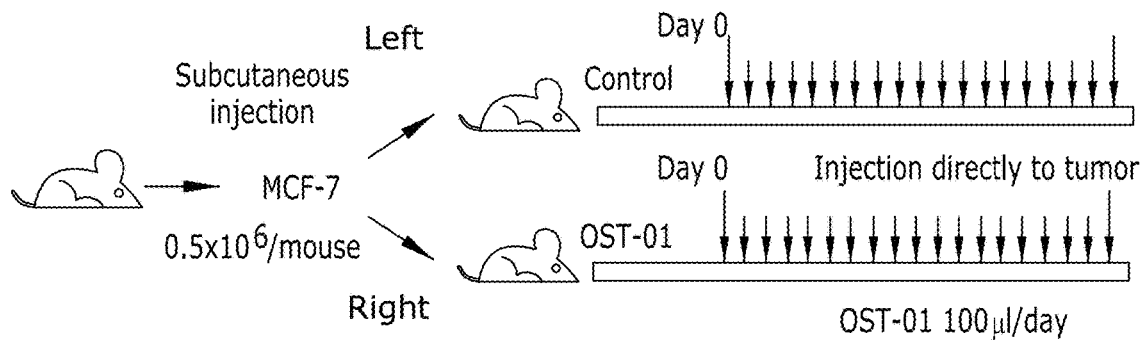
*FIG. 18A*
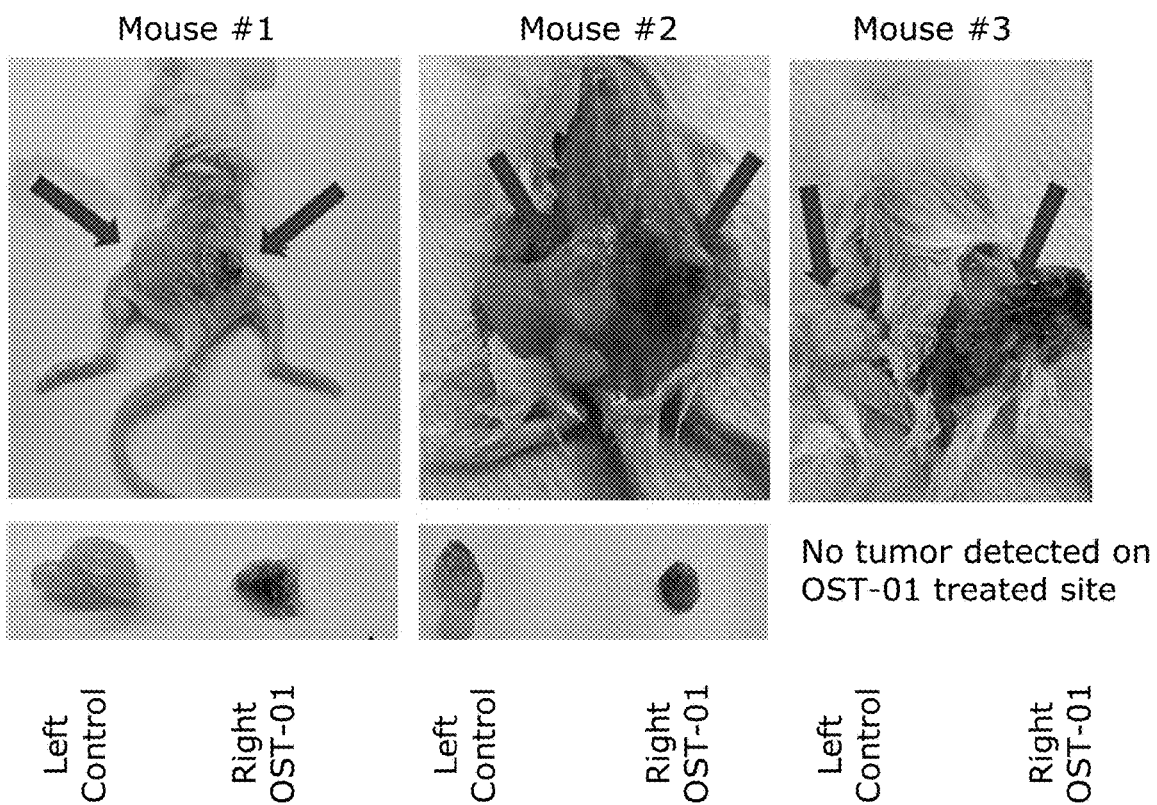
*FIG. 18B*   *FIG. 18C*   *FIG. 18D*

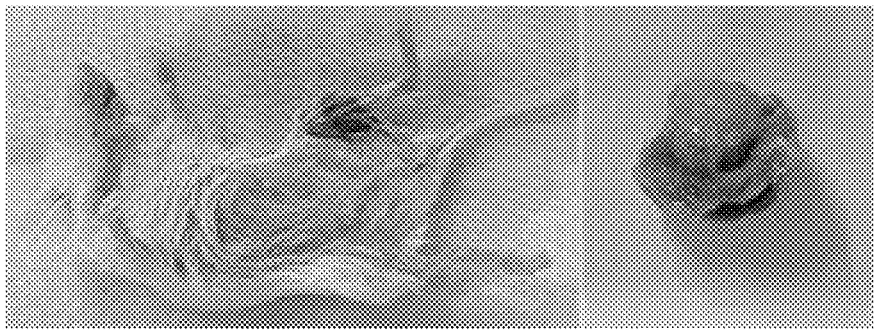
FIG. 20I  OST-01
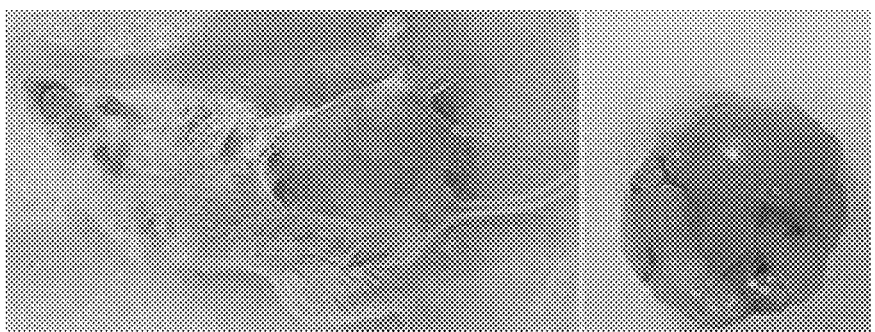
FIG. 20H  OST-01
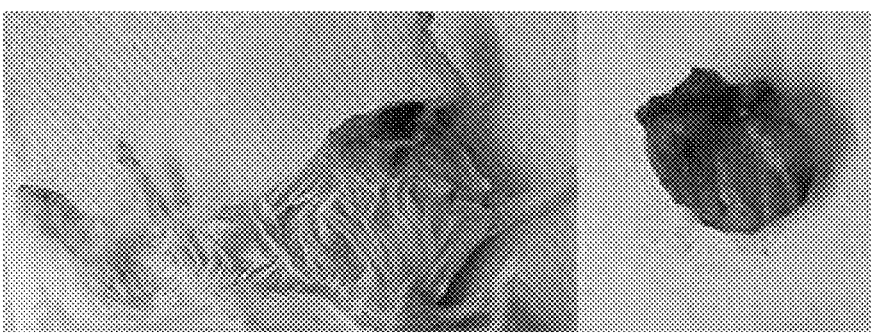
FIG. 20G  Control
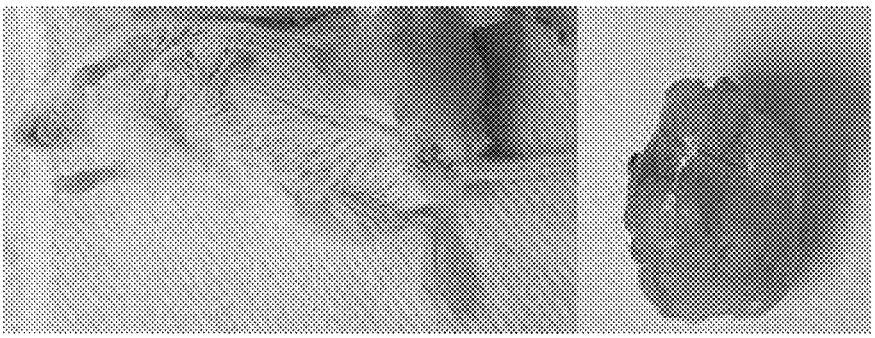
FIG. 20F  Control C-myc
Control                OST-01
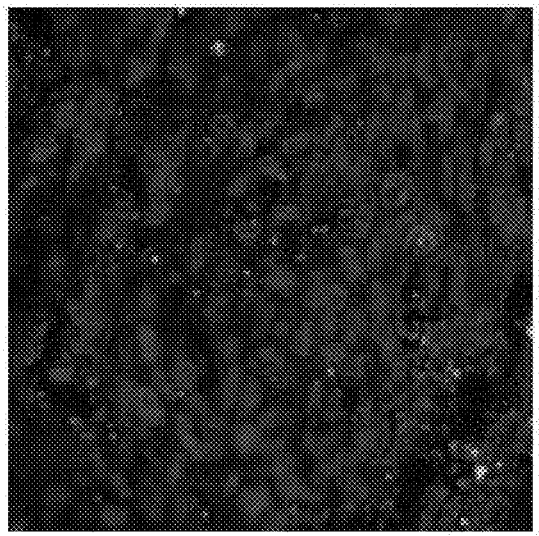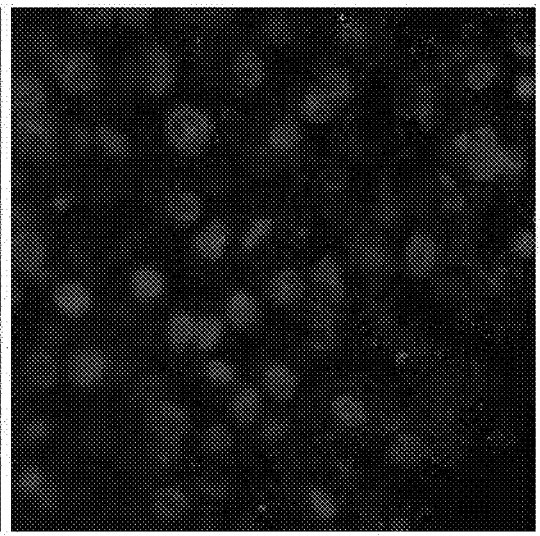
*FIG. 21A*
P-AKT
Control                OST-01
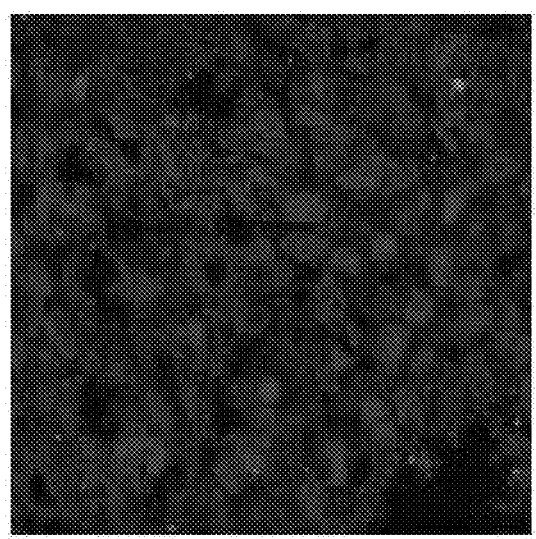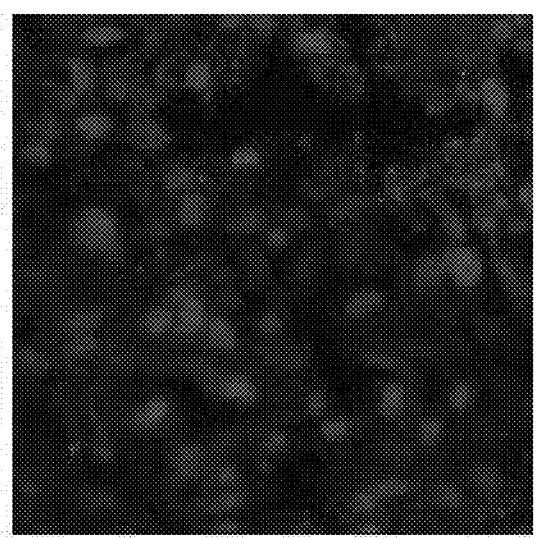
*FIG. 21B*

PCNA
Control          OST
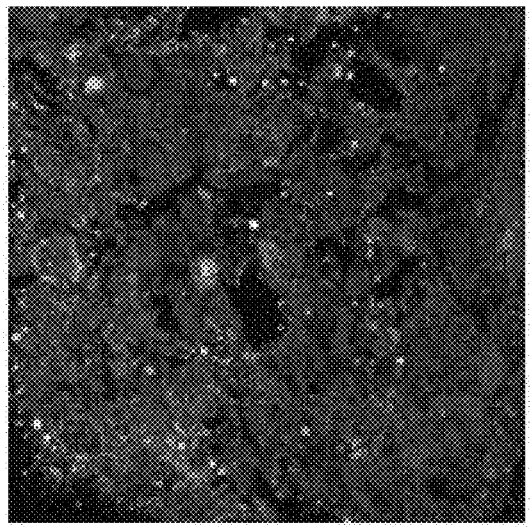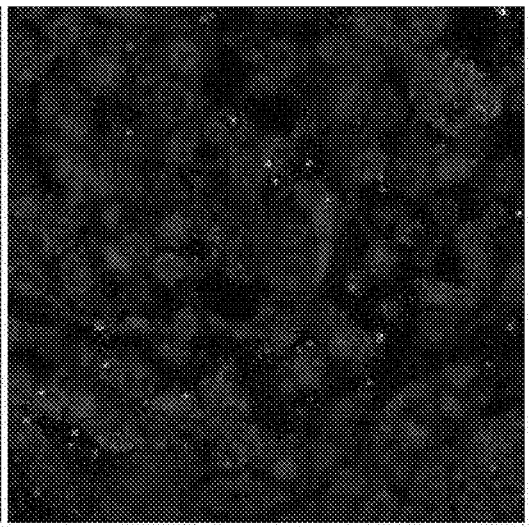
*FIG. 21C*
Cleaved caspase 3
Control          OST-01
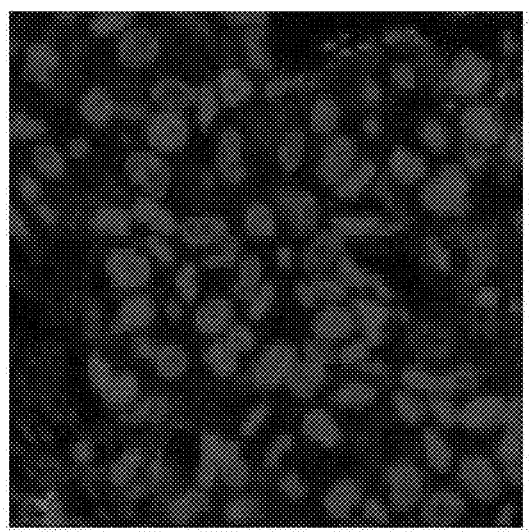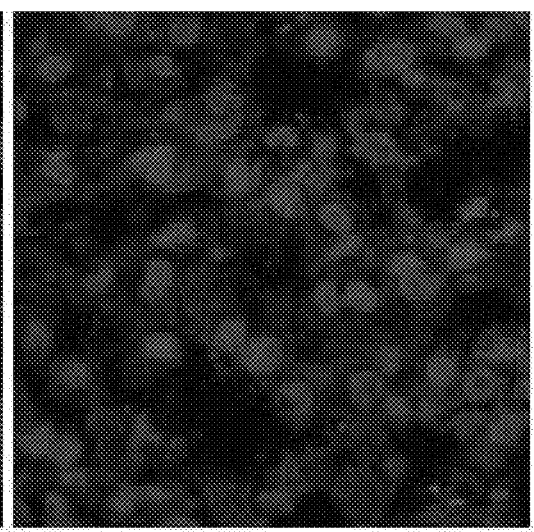
*FIG. 21D* pH2AX
Control            OST
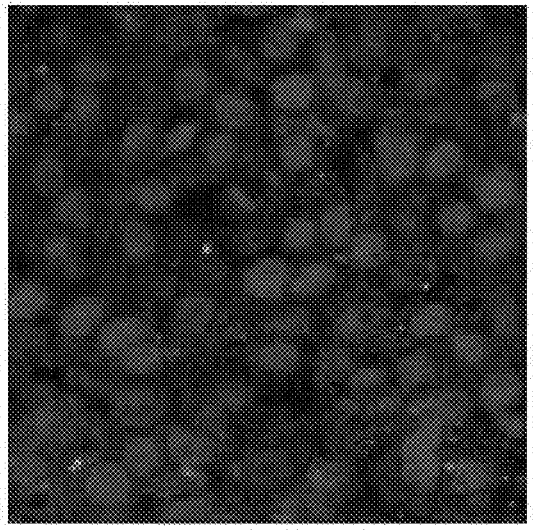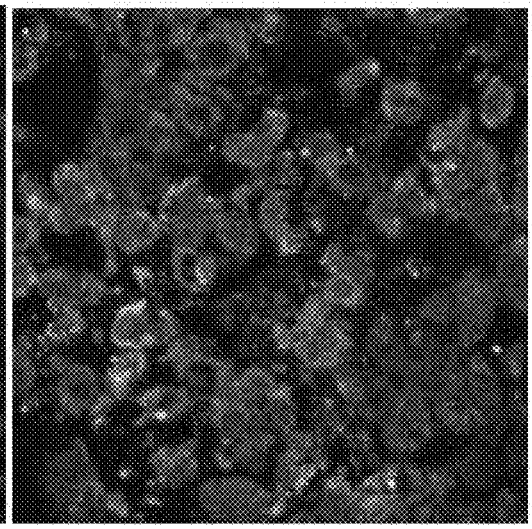
FIG. 21E
p53
Control            OST-01
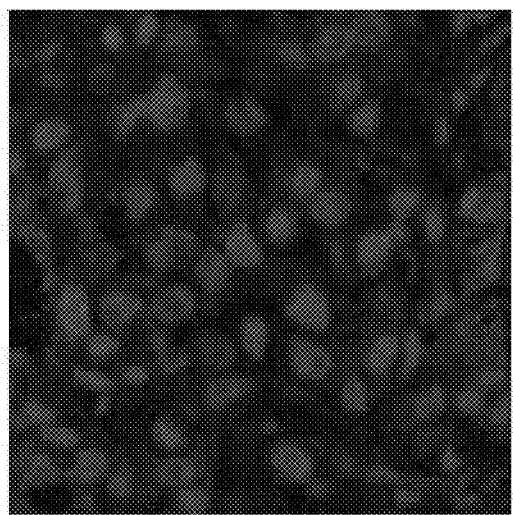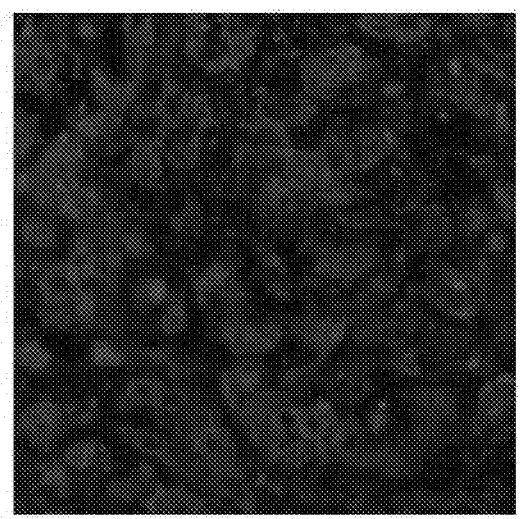
FIG. 21F

ANTI-ONCOGENIC PHYTOCHEMICALS COMPRISING SUBSTITUTED HENICOSANOIC ACID AND HENICOSENOIC ACID This application is a continuation that claims the benefit of priority and is entitled to the filing date pursuant to 35 U.S.C. § 120 of U.S. Non-Provisional patent application Ser. No. 18/192,624, filed Mar. 29, 2023, a 35 U.S.C. § 111 patent application that claims the benefit of priority and is entitled to the filing date pursuant to 35 U.S.C. § 119(e) of U.S. Provisional Patent Application 63/362,121, filed Mar. 29, 2022, the content of which is hereby incorporated by reference in its entirety.

According to the World Health Organization (WHO), cancer is among the leading causes of death worldwide. This organization estimated that cancer is the first or second leading cause of death before the age of 70 years in at least 112 of 183 countries and ranks third or fourth in additional 23 countries. Overall, the burden of cancer incidence and mortality is rapidly growing world-wide. This reflects both aging and growth of the population as well as changes in the prevalence and distribution of the main risk factors for cancer, several of which are associated with socio-economic development. For example, the WHO reported that in 2018 there were 18.1 million new cases and 9.5 million cancer-related deaths. However, by 2040, the number of new cancer cases per year is expected to rise to more than 30 million and the number of cancer-related deaths to 16.3 million. Generally, cancer rates are highest in countries whose populations have the highest life expectancy, education level, and standard of living.

According to estimated new cases in 2021, the National Cancer Institute (NCI) reported that the most common cancers, in descending order, are breast, lung, prostate, and colorectal cancer. The three most common cancers in women are breast, lung, and colorectal, and these will account for an estimated 50% of all new cancer diagnoses in 2021. For men, prostate, lung, and colorectal cancers account for an estimated 43% of all cancers diagnosed in 2020.

With or without surgical removal, currently available options for cancer treatment include chemotherapy, hormone therapy, hyperthermia therapy, immunotherapy, photodynamic therapy, radiation therapy, or stem cell transplant therapy. These treatments can be used alone or in various combinations. The primarily available chemotherapeutic agents are antimetabolites (e.g., methotrexate), DNA-interactive agents (e.g., cisplatin, doxorubicin), and anti-tubulin agents (e.g., taxanes). The major disadvantages of chemotherapy are early and long-term onset of drug resistance that can lead to cancer treatment refractoriness and recurrence, and toxicity due to off-targeted effect on healthy tissues and organ that can restrain the use of many anticancer drugs to younger individuals with no-comorbidities. In addition, many chemotherapeutic agents are cancer specific and only work on selected types of cancer. Finally, their use is generally very costly and beyond the reach of a large number of individuals suffering from a cancer. Unfortunately, cancer is a disease mainly prevalent in the aging population which often present with co-morbidities ("unfit" individuals) that preclude the use of most effective treatments.

To overcome the problems of present therapy, the search for new promising anticancer agents with better efficacy, lesser side effects and lack of cross-resistance with currently available cancer therapeutics is highly needed. What is needed is a treatment that has the ability to inhibit or reduce a cancer cells ability to survive and/or divide while at the same time the treatment: (1) is tolerated by an individual; (2) works against many different cancers; and (3) is affordable so that all individuals suffering from a cancer can be administered the treatment. Development of phytochemicals from plants and their derivatives is one promising option to find novel therapeutics with high activity and low side effects for cancer patients. Such phytochemicals have should have significant antitumor potential and be useful in older and unfit individuals.

The present specification discloses the identification of a potent anti-oncogenic phytochemical and its derivatives as well as methods and uses in treating a wide range of non-solid and solid cancers.

SUMMARY

Aspects of the present specification disclose compositions comprising one or more anti-oncogenic phytochemicals. A disclosed anti-oncogenic phytochemical can comprise one or more trichothecenes, such as, e.g., one or more Type A trichothecenes, one or more Type B trichothecenes, one or more Type C trichothecenes, one or more Type D trichothecenes, or any combination thereof.

Other aspects disclose a product by process where an extract comprising one or more anti-oncogenic phytochemicals disclosed herein is prepared by a method disclosed herein. A disclosed method of preparation can comprise the steps of preparing a macerate comprising a solvent and a plant material from one or more plant species belonging to the family Asteraceae; incubating the macerate for a period of time in order to solubilize the one or more anti-oncogenic phytochemicals disclosed herein; and purifying the macerate to produce the extract comprising one or more anti-oncogenic phytochemicals.

Other aspects disclose a product by process where a pharmaceutical composition comprising one or more anti-oncogenic phytochemicals disclosed herein is prepared by a method disclosed herein. A disclosed method of preparation can comprise the steps of preparing a macerate comprising a solvent and a plant material from one or more plant species belonging to the family Asteraceae; incubating the macerate for a period of time in order to solubilize the one or more anti-oncogenic phytochemicals disclosed herein; and purifying the macerate to produce the pharmaceutical composition comprising one or more anti-oncogenic phytochemicals.

Other aspects disclose a product by process where a medicament comprising one or more anti-oncogenic phytochemicals disclosed herein is prepared by a method disclosed herein. A disclosed method of preparation can comprise the steps of preparing a macerate comprising a solvent and a plant material from one or more plant species belonging to the family Asteraceae; incubating the macerate for a period of time in order to solubilize the one or more anti-oncogenic phytochemicals disclosed herein; and purifying the macerate to produce the medicament comprising one or more anti-oncogenic phytochemicals.

Other aspects of the present specification disclose a method of treating a cancer in an individual. A disclosed method of treatment can comprise administering a pharmaceutical composition disclosed herein or medicaments disclosed herein to an individual. Other aspects of the present specification disclose a method of treating a neoplasm in an individual. A disclosed method of treatment can comprise administering a pharmaceutical composition disclosed herein or medicaments disclosed herein to an individual.

Other aspects of the present specification disclose pharmaceutical compositions disclosed herein or a medicament disclosed herein for use in the treatment of a cancer. Other aspects of the present specification disclose pharmaceutical compositions disclosed herein or a medicament disclosed herein for use in the treatment of a neoplasm.

Other aspects of the present specification disclose use of pharmaceutical compositions disclosed herein or medicaments disclosed herein in the treatment of a cancer. Other aspects of the present specification disclose use of pharmaceutical compositions disclosed herein or medicaments disclosed herein in the treatment of a neoplasm.

Other aspects of the present specification disclose use of pharmaceutical compositions disclosed herein in the manufacture of a medicament for the treatment of a cancer. Other aspects of the present specification disclose use of pharmaceutical compositions disclosed herein in the manufacture of a medicament for the treatment of a neoplasm.

BRIEF DESCRIPTION OF DRAWINGS

The accompanying drawings, which are incorporated in and constitute a part of this specification, illustrate aspects of the disclosed subject matter in at least one of its exemplary embodiments, which are further defined in detail in the following description. Features, elements, and aspects of the disclosure are referenced by numerals with like numerals in different drawings representing the same, equivalent, or similar features, elements, or aspects, in accordance with one or more embodiments. The drawings are not necessarily to scale, emphasis instead being placed upon illustrating the principles herein described and provided by exemplary embodiments of the invention. In such drawings:

FIG. 1B showing the results of KG-1a cells treated with either OST-01 or a vehicle control; and FIG. 1C showing the results of Kasumi-1 cells treated with either OST-01 or a vehicle control;

FIGS. 3A-3C show bar graphs of cells stained with Annexin V obtained from apoptosis flow cytometry assays with FIG. 3A showing the results of MV-4-11 cells treated with either OST-01 or a vehicle control; FIG. 3B showing the results of KG-1a cells treated with either OST-01 or a vehicle control; and FIG. 3C showing the results of Kasumi-1 cells treated with either OST-01 or a vehicle control;

FIG. 4 shows a representative gel staining obtained from a DNA ladder assay examining the degree of genomic DNA fragmentation occurring in cells from three different AML cell lines treated with either OST-01 or a vehicle control;

FIG. 5 shows a representative blot staining obtained from immunoblotting analyses examining the expression levels of the apoptosis biomarker the cleaved form of PARP, p53, phosphorylated H2A.X and the cleaved form of caspase-3 in cells from three different AML cell lines treated with either OST-01 or a vehicle control;

FIG. 6B showing KG-1a cells treated with OST-01; FIG. 6C showing Kasumi-1 cells treated with a vehicle control; and FIG. 6D showing Kasumi-1 cells treated with OST-01. Arrowheads identify representative mitochondria. Scale bar, 1000 nm;

FIGS. 7A-7F show representative confocal images of cationic carbocyanine dye JC-1 staining obtained from mitochondrial membrane potential assays with FIG. 7A showing a red channel image of Kasumi-1 cells treated with a vehicle control; FIG. 7B showing a green channel image Kasumi-1 cells treated with a vehicle control; FIG. 7C showing a merged red/green channel image Kasumi-1 cells treated with a vehicle control; FIG. 7D showing a red channel image of Kasumi-1 cells treated with OST-01; FIG. 7E showing a green channel image Kasumi-1 cells treated with OST-01; and FIG. 7F showing a merged red/green channel image Kasumi-1 cells treated with OST-01;

FIG. 8B showing KG-1a cells treated with a vehicle control; FIG. 8C showing Kasumi-1 cells treated with OST-01; and FIG. 8D showing Kasumi-1 cells treated with a vehicle control;

FIG. 9B showing KG-1a cells treated with a vehicle control; FIG. 9C showing Kasumi-1 cells treated with OST-01; and FIG. 9D showing Kasumi-1 cells treated with a vehicle control;

FIG. 11B showing extracellular acidification (ECAR) rates of KG-1a cells treated with either 1 µL OST-01, 2 µL OST-01, or a vehicle control;

FIG. 12A showing a graph comparing 5' external transcribed sequence (ETS) pre-rRNA transcription occurring in AML blast cells treated with either OST-01 or a vehicle control with 5' external transcribed sequence (ETS) pre-rRNA transcription occurring in MNCs treated with either OST-01 or a vehicle control; FIG. 12B showing images comparing RNA labeling with [$^{32}$P] from total RNA isolated from AML blast cells treated with either OST-01 or a vehicle control with RNA labeling with [$^{32}$P] from total RNA isolated from MNCs treated with either OST-01 or a vehicle control;

FIG. 13A showing a graph of 5'ETS pre-rRNA levels from AML blast cells treated with either OST-01 or a vehicle control; FIG. 13B showing a graph of 5'ETS pre-rRNA levels from MNCs treated with either OST-01 or a vehicle control; FIG. 13C showing RNA labeling with [$^{32}$P] from AML blast cells treated with either OST-01 or a vehicle control; FIG. 13D showing RNA labeling with [$^{32}$P] from MNCs treated with either OST-01 or a vehicle control; FIG. 13E showing a graph comparing cell proliferation levels occurring in AML blast cells treated with either OST-01 or a vehicle control with cell proliferation levels occurring in MNCs treated with either OST-01 or a vehicle control; FIG. 13F showing a graph comparing apoptosis levels occurring in AML blast cells treated with either OST-01 or a vehicle control with apoptosis levels occurring in MNCs treated with either OST-01 or a vehicle control.

FIG. 14B showing a graph of white blood cell counts from animals treated with either OST-01 or a vehicle control; FIG. 14C showing a graph of survival of animals treated with either OST-01 or a vehicle control; FIG. 14D showing a photograph of spleens taken from animals treated with either OST-01 or a vehicle control; FIG. 14E showing a photograph of spleens taken from animals treated with either OST-01 or a vehicle control; FIG. 14F showing photographs of representative bioluminescence images of animals treated with either OST-01 or a vehicle control with x indicating death of an animal; and FIG. 14G showing a graph of survival of animals treated with either OST-01 or a vehicle control;

FIG. 16 shows bar graphs of cells obtained from superoxide activity assays showing cells from five different solid cancer cell lines treated with either OST-01 or a vehicle control;

FIGS. 17A-17F show representative microscopy images of crystal violet-stained cells obtained from cell invasion assays with FIG. 17A showing MCF-7 cells treated with a vehicle control; FIG. 17B showing MCF-7 cells treated with OST-01; FIG. 17C showing HCT-116 cells treated with a vehicle control; FIG. 17D showing HCT-116 cells treated with OST-01; FIG. 17E showing A549 cells treated with a vehicle control; and FIG. 17F showing A549 cells treated with OST-01;

FIGS. 18A-18G show results obtained from two different breast tumor xenograft mouse models with FIG. 18A showing a diagram of the study design of breast tumor xenograft mouse model using MCF-7 breast cancer cells; FIG. 18B showing a photograph of tumors in situ and isolated from animal from xenograft mouse model using MCF-7 breast cancer cells treated with either OST-01 or a vehicle control by intratumor injection; FIG. 18C showing a photograph of tumors in situ and isolated from animal from xenograft mouse model using MCF-7 breast cancer cells treated with either OST-01 or a vehicle control by intratumor injection; FIG. 18D showing a photograph of tumors in situ and isolated from animal treated with either OST-01 or a vehicle control by intratumor injection; FIG. 18E showing a graph of tumor weight in animals from xenograft mouse model using BT474 triple negative breast cancer cells treated with either OST-01 or a vehicle control by oral gavage; FIG. 18F showing a graph of tumor weight over time in animals from xenograft mouse model using BT474 triple negative breast cancer cells treated with either OST-01 or a vehicle control by oral gavage; and FIG. 18G showing a graph of tumor weight in animals from xenograft mouse model using MDA-MB-231 triple negative breast cancer cells treated with either OST-01 or a vehicle control by oral gavage;

FIG. 19B showing a photograph of tumors isolated from three different animals from xenograft mouse model using HCT-116 colon cancer cells treated with either OST-01 or a vehicle control; and FIG. 19C showing a graph of tumor weight treated with either OST-01 or a vehicle control;

FIGS. 20A-20I show results obtained from a lung tumor xenograft mouse model with FIG. 20A showing a diagram of an intratumor injection study design of lung tumor xenograft mouse model using A549 lung cancer cells; FIG. 20B showing a photograph of tumors in situ and isolated from animal from xenograft mouse model using A549 lung cancer cells treated with a vehicle control; FIG. 20C showing a photograph of tumors in situ and isolated from animal treated with a vehicle control; FIG. 20D showing a photograph of tumors in situ and isolated from animal from xenograft mouse model using A549 lung cancer cells treated with OST-01; FIG. 20E showing a photograph of tumors in situ and isolated from animal from xenograft mouse model using A549 lung cancer cells treated with OST-01; FIG. 20F showing a photograph of tumors in situ and isolated from animal from xenograft mouse model using A549 lung cancer cells treated with a vehicle control; FIG. 20G showing a photograph of tumors in situ and isolated from animal treated with OST-01; FIG. 20H showing a photograph of tumors in situ and isolated from animal treated with a vehicle control; and FIG. 20I showing a photograph of tumors in situ and isolated from animal treated with OST-01;

FIGS. 21A-21F show representative confocal images of tumor sections obtained from a lung tumor xenograft mouse model using A549 lung cancer cells immuno-stained with antibodies raised against oncogenic and apoptosis biomarkers with FIG. 21A showing an image of tumor sections treated with either OST-01 or a vehicle control and stained for the oncogenic protein c-myc; FIG. 21B showing an image of tumor sections treated with either OST-01 or a vehicle control and stained for the phosphorylated active form of the oncogenic protein p-AKT; FIG. 21C showing an image of tumor sections treated with either OST-01 or a vehicle control and stained for the oncogenic protein PCNA; FIG. 21D showing an image of tumor sections treated with either OST-01 or a vehicle control and stained for the cleaved active form of the apoptotic protein caspase-3; FIG. 21E showing an image of tumor sections treated with either OST-01 or a vehicle control and stained for the phosphorylated active form of the apoptotic protein p-H2A.X; and FIG. 21F showing an image of tumor sections treated with either OST-01 or a vehicle control and stained for the apoptotic protein p53;

FIG. 22B showing a graph of tumor weight over time in animals from xenograft mouse model using A549 lung cancer cells treated with either OST-01 or a vehicle control by oral gavage;

FIG. 23B showing a graph of tumor weight over time in animals from xenograft mouse model using LN229 glioblastoma cancer cells treated with either OST-01 or a vehicle control by oral gavage;

FIG. 24B showing a bar graph of cells stained with Annexin V obtained from apoptosis flow cytometry assay from MV-4-11 cells treated with HPLC fractions of OST-01 containing anti-oncogenic activity;

FIG. 25B showing the results of THP-1 cells treated with HPLC fractions of OST-01 containing anti-oncogenic activity; and FIG. 25C showing the results of HL-60 cells treated with HPLC fractions of OST-01 containing anti-oncogenic activity;

FIG. 26B showing the results of THP-1 cells treated with an escalating dose of (2E)-21-Hydroxy-2-henicosenoic acid;

FIG. 27B showing the results of HL-60 cells treated with an escalating dose of 21-Hydroxyhenicosenoic acid; FIG. 28B showing the results of HL-60 cells treated with an escalating dose of 21-Hydroxyhenicosenoic acid.

DETAILED DESCRIPTION

Figure 1A:
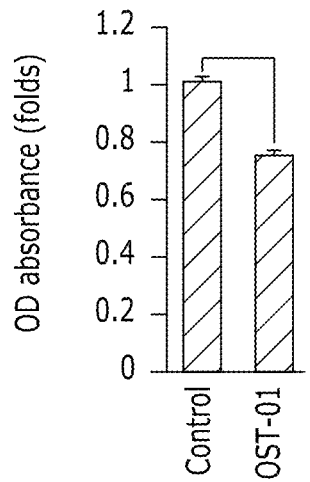
FIGS. 1A-1C show bar graphs of the amount of formazan produced from MTS proliferation assays in Acute Myeloid Leukemia (AML) cells treated with OST-01 with FIG. 1A showing the results of MV-4-11 cells treated with either OST-01 or a vehicle control.

The present specification discloses the identification of OST-01, a potent anti-oncogenic phytochemical demonstrating effectiveness in both non-solid and solid cancers. Without wishing to be limited by any theory, the anti-oncogenic properties of OST-01 appear, in part, reduce or inhibit protein synthesis, reduce, or inhibit cellular metabolism, and stimulate or enhance immune cell activity. With respect to the reduction or inhibition of protein synthesis, the anti-oncogenic properties of OST-01 would target all types of cancer cells as all are dependent on continued protein expression for survival. With respect to the reduction or inhibition of cellular metabolism, the anti-oncogenic properties of OST-01 would preferentially target cancer stem cells since only cancer cells dependent on energy production through the process of electron transport and oxidative phosphorylation would be impacted. With respect to the stimulation or enhancement of immune cell activity, the anti-oncogenic properties of OST-01 would target all types of cancer cells as all would be considered as a foreign threat.

Aspects of the present specification disclose, in part, a composition. A composition disclosed herein is generally administered as a pharmaceutical acceptable composition. As used herein, the term "pharmaceutically acceptable composition" is synonymous with "pharmaceutical composition" and means the combination of one or more anti-oncogenic phytochemicals disclosed herein that are combined with one or more solvents and/or one or more excipient and/or other components disclosed herein to form the product that is administered to an individual. A pharmaceutical composition disclosed herein is useful for medical and veterinary applications. A pharmaceutical composition may be administered to an individual alone, or in combination with other supplementary active pharmaceutical ingredients, agents, drugs, or hormones.

Aspects of the present specification disclose, in part, one or more anti-oncogenic phytochemicals. In some embodiments, one or more anti-oncogenic phytochemicals disclosed herein can be one or more compounds isolated from the plant family Asteraceae. In some embodiments, one or more anti-oncogenic phytochemicals disclosed herein can be one or more compounds isolated from the plant subfamily Asteroideae. In some embodiments, one or more anti-oncogenic phytochemicals disclosed herein can be one or more compounds isolated from the plant supertribe Asterodae. In some embodiments, one or more anti-oncogenic phytochemicals disclosed herein can be one or more compounds isolated from the plant tribe Astereae. In some embodiments, one or more anti-oncogenic phytochemicals disclosed herein can be one or more compounds isolated from the plant genus *Baccharis*. In some embodiments, one or more anti-oncogenic phytochemicals disclosed herein can be one or more compounds isolated from the plant species *Baccharis artemisioides*, *Baccharis coridifolia*, or *Baccharis dracunculifolia*.

In some embodiments, one or more anti-oncogenic phytochemicals disclosed herein can comprise one or more compounds belonging to chemical formula I:

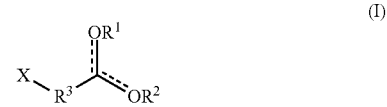

(I)

wherein $R^1$ is independently selected from H, $CH_3$ or $C_2H_5$ or is not present; $R^2$ is independently selected from H, $CH_3$ or $C_2H_5$ or is not present; provided that when $R^1$ is not present, $R^2$ is selected from H, $CH_3$ or $C_2H_5$ and when $R^2$ is not present $R^1$ is selected from H, $CH_3$ or $C_2H_5$; $R^3$ is a $C_{4-40}$ straight or branched chain, alkyl or alkylene and optionally substituted with one or more groups independently selected from $CH_3$, OH, SH, $NH_2$, OMe, OEt, N(H)Me and $NMe_2$; and X is independently selected from $CH_3$, OH, SH, $NH_2$, OMe, OEt, N(H)Me, and $NMe_2$. In some embodiments, chemical formula I provides a $R^3$ that is a $C_{8-36}$ straight or branched chain, alkyl or alkylene and optionally substituted with one or more groups independently selected from $CH_3$, OH, SH, $NH_2$, OMe, OEt, N(H)Me and $NMe_2$. In some embodiments, chemical formula I provides a $R^3$ that is a $C_{10-30}$ straight or branched chain, alkyl or alkylene and optionally substituted with one or more groups independently selected from $CH_3$, OH, SH, $NH_2$, OMe, OEt, N(H)Me and $NMe_2$. In some embodiments, chemical formula I provides a $R^3$ that is a $C_{12-28}$ straight or branched chain, alkyl or alkylene and optionally substituted with one or more groups independently selected from $CH_3$, OH, SH, $NH_2$, OMe, OEt, N(H)Me and $NMe_2$.

In some embodiments, chemical formula I provides a $R^3$ that is a $C_{4-40}$ straight or branched chain, alkyl or alkylene. In some embodiments, chemical formula I provides a $R^3$ that is a $C_{8-36}$ straight or branched chain, alkyl or alkylene. In some embodiments, chemical formula I provides a $R^3$ that is a $C_{10-30}$ straight or branched chain, alkyl or alkylene. In some embodiments, chemical formula I provides a $R^3$ that is a $C_{12-28}$ straight or branched chain, alkyl or alkylene.

In some embodiments, chemical formula I provides an $R^3$ that is a $C_{4-40}$ straight chain alkyl or alkylene and optionally substituted with one or more groups independently selected from $CH_3$, $C_2H_5$, OH, SH, $NH_2$, OMe, OEt, N(H)Me and $NMe_2$. In some embodiments, chemical formula I provides an $R^3$ that is a $C_{8-36}$ straight chain alkyl or alkylene and optionally substituted with one or more groups independently selected from $CH_3$, $C_2H_5$, OH, SH, $NH_2$, OMe, OEt, N(H)Me and $NMe_2$. In some embodiments, chemical formula I provides an $R^3$ that is a $C_{10-30}$ straight chain alkyl or alkylene and optionally substituted with one or more groups independently selected from $CH_3$, $C_2H_5$, OH, SH, $NH_2$, OMe, OEt, N(H)Me and $NMe_2$. In some embodiments, chemical formula I provides an $R^3$ that is a $C_{12-28}$ straight chain alkyl or alkylene and optionally substituted with one or more groups independently selected from $CH_3$, $C_2H_5$, OH, SH, $NH_2$, OMe, OEt, N(H)Me and $NMe_2$.

In some embodiments, one or more anti-oncogenic phytochemicals disclosed herein can comprise one or more compounds belonging to chemical formula II:

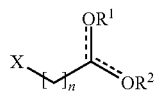

(II)

wherein $R^1$ is independently selected from H, $CH_3$ or $C_2H_5$ or is not present; $R^2$ is independently selected from H, $CH_3$ or $C_2H_5$ or is not present; provided that when $R^1$ is not present, $R^2$ is selected from H, $CH_3$ or $C_2H_5$ and when $R^2$ is not present $R^1$ is selected from H, $CH_3$ or $C_2H_5$; n is an integer between 4 and 40; and X is independently selected from $CH_3$, OH, SH, $NH_2$, OMe, OEt, N(H)Me, and $NMe_2$. In some embodiments, chemical formula I provides a n that is an integer between 8 and 36. In some embodiments, chemical formula I provides a n that is an integer between 10 and 30. In some embodiments, chemical formula I provides a n that is an integer between 12 and 28.

In some embodiments, one or more compounds belonging to chemical formula I or chemical formula II comprises (2E)-21-Hydroxy-2-henicosenoic acid or a derivative thereof, or 21-Hydroxyhenicosanoic acid or a derivative thereof. In some embodiments, one or more compounds belonging to chemical formula I or chemical formula II comprises (2E)-21-Hydroxy-2-henicosenoic acid or a derivative thereof. In some embodiments, one or more compounds belonging to chemical formula I or chemical formula II comprises (2E)-21-Hydroxy-2-henicosenoic acid. In some embodiments, one or more compounds belonging to chemical formula I or chemical formula II comprises 21-Hydroxyhenicosanoic acid or a derivative thereof. In some embodiments, one or more compounds belonging to chemical formula I or chemical formula II comprises 21-Hydroxyhenicosanoic acid.

In some embodiments, one or more compounds belonging to chemical formula I or chemical formula II comprises the following compound:

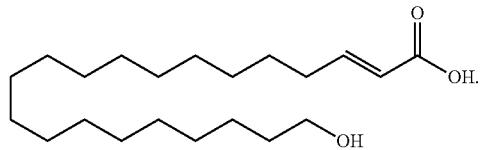 [SMILES: O=C(O)/C=C/CCCCCCCCCCCCCCCCCCO]

In some embodiments, one or more compounds belonging to chemical formula I or chemical formula II comprises the following compound:

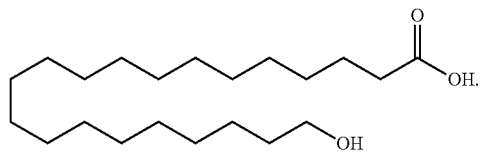 [SMILES: O=C(O)CCCCCCCCCCCCCCCCCCCCO]

In some embodiments, one or more anti-oncogenic phytochemicals disclosed herein can comprise a free $c_{3-40}$ unsaturated fatty acid. Non-limiting examples of a free $c_{3-40}$ fatty acid include propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid (hexadecenoic acid), margaric acid, stearic acid (octadecenoic acid), nonadecylic acid, arachidic acid (eicosanoic acid), heneicosylic acid, behenic acid (docosanoic acid), tricosylic acid, lignoceric acid (tetracosanic acid), pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontanoic acid, octatriacontanoic acid, nonatriacontanoic acid, and tetracontanoic acid.

In some embodiments, one or more anti-oncogenic phytochemicals disclosed herein can comprise a free ω-3 unsaturated fatty acid. Non-limiting examples of a free ω-3 unsaturated fatty acid include octenoic acid, decenoic acid, decadienoic acid, lauroleic acid, laurolinoleic acid, myristovaccenic acid, myristolinoleic acid, myristolinolenic acid, palmitolinolenic acid, palmitidonic acid, α-linolenic acid, stearidonic acid, dihomo-α-linolenic acid, eicosatetraenoic acid, eicosapentaenoic acid, clupanodonic acid (7,10,13,16,19-docosapentaenoic acid), docosahexaenoic acid, 9,12,15,18,21-tetracosapentaenoic acid, and 6,9,12,15,18,21-tetracosahexaenoic acid.

In some embodiments, one or more anti-oncogenic phytochemicals disclosed herein can comprise a free ω-5 unsaturated fatty acid. Non-limiting examples of a free ω-5 unsaturated fatty acid include myristoleic acid, palmitovaccenic acid, α-eleostearic acid, β-eleostearic acid, punicic acid, 7,10,13-octadecatrienoic acid, 9,12,15-eicosatrienoic acid, and β-eicosatetraenoic acid.

In some embodiments, one or more anti-oncogenic phytochemicals disclosed herein can comprise a free ω-6 unsaturated fatty acid. Non-limiting examples of a free ω-6 unsaturated fatty acid include 8-tetradecenoic acid, 12-octadecenoic acid, linoleic acid, linolelaidic acid, γ-linolenic acid, calendic acid, pinolenic acid, dihomo-linoleic acid, dihomo-γ-linolenic acid, arachidonic acid, adrenic acid, and osbond acid (4,7,10.13.16 docosapentaenoic acid).

In some embodiments, one or more anti-oncogenic phytochemicals disclosed herein can comprise a free ω-7 unsaturated fatty acid. Non-limiting examples of a free ω-7 unsaturated fatty acid include palmitoleic acid, vaccenic acid, rumenic acid, paullinic acid, and 7,10,13-eicosatrienoic acid.

In some embodiments, one or more anti-oncogenic phytochemicals disclosed herein can comprise a free ω-9 unsaturated fatty acid. Non-limiting examples of a free ω-9 unsaturated fatty acid include oleic acid, elaidic acid, gondoic acid (11-eicosenoic acid), erucic acid, nervonic acid, 8,11-eicosadienoic acid, and mead acid (eicosatrienoic acid).

In some embodiments, one or more anti-oncogenic phytochemicals disclosed herein can comprise a free ω-10 unsaturated fatty acid. Non-limiting examples of a free ω-10 unsaturated fatty acid include sapienic acid.

In some embodiments, one or more anti-oncogenic phytochemicals disclosed herein can comprise a free ω-11 unsaturated fatty acid. Non-limiting examples of a free ω-11 unsaturated fatty acid include gadoleic acid.

In some embodiments, one or more anti-oncogenic phytochemicals disclosed herein can comprise a free ω-12 unsaturated fatty acid. Non-limiting examples of a free ω-12 unsaturated fatty acid include 4-hexadecenoic acid, petroselinic acid, and 8-eicosenoic acid.

In some embodiments, one or more anti-oncogenic phytochemicals disclosed herein can comprise one or more trichothecenes. Trichothecenes are a class of structurally related sesquiterpenes comprising over 150 chemically related mycotoxins. Trichothecenes comprise a core macrocyclic structure that is amphipathic and includes a single six-membered ring containing a single oxygen atom, flanked by two carbon rings. This core ring structure contains an epoxide, or tricyclic ether, at the 12.13 carbon positions, as well as a double bond at the 9, 10 carbon positions. The most important structural features causing the biological activities of trichothecenes are the 12,13-epoxy ring, the presence of hydroxyl or acetyl groups at appropriate positions on the trichothecene nucleus, and the structure and position of the sidechain. In particular, the 12,13-epoxy ring and the double bond at the 9, 10 carbon positions are primarily responsible for trichothecene ability to inhibit protein synthesis and incur general cytotoxic effects. All trichothecenes are related through this common structure, but each trichothecene also has a unique substitution pattern of oxygen containing functional groups at possible sites on carbons 3, 4, 7, 8, and 15. These functional groups govern the properties of an individual tricothecene and also serve as the basis for the most commonly used classification system for this family of toxins. This classification system breaks up the trichothecene family into four groups, namely Type A tricothecenes, Type B tricothecenes, Type C tricothecenes, and Type D tricothecenes. Non-limiting examples of specific tricothecenes include Isosatratoxin F, Roridin A, Roridin E, Roridin H, Roridin L-2, Satratoxin G, Satratoxin H, Verrucarin A, and Verrucarin J.

In some embodiments, one or more anti-oncogenic phytochemicals disclosed herein can comprise one or more flavonoids. Flavonoids have the general structure of a 15-carbon skeleton, which contains of two phenyl rings (A and B) and a heterocyclic ring (C, the ring containing the embedded oxygen). Flavonoids are ketone-containing polyhydroxy polyphenol compounds and can be classified into three groups, 1) flavonoids or bioflavonoids; 2) isoflavonoids, derived from 3-phenylchromen-4-one (3-phenyl-1,4-benzopyrone) structure; and 3) neoflavonoids, derived from 4-phenylcoumarine (4-phenyl-1,2-benzopyrone) structure. Subgroups of flavonoids include, without limitation, anthocyanidins, anthoxanthins, flavanones, flavanonols, flavans, and isoflavonoids.

In some embodiments, one or more anti-oncogenic phytochemicals disclosed herein can comprise one or more flavanoids. Like flavonoids, flavanoids have the general structure of a 15-carbon skeleton, which contains of two phenyl rings (A and B) and a heterocyclic ring (C, the ring containing the embedded oxygen). The difference is that flavanoids are non-ketone polyhydroxy polyphenol compounds.

In some embodiments, one or more anti-oncogenic phytochemicals disclosed herein can comprise chlorogenic acid or isomer. A polyphenol, chlorogenic acid is the ester formed between caffeic acid and the 3-hydroxyl of L-quinic acid (3-caffeoylquinic acid). Isomers of chlorogenic acid include the caffeoyl ester at other hydroxyl sites on the quinic acid ring, such as, e.g., cryptochlorogenic acid (4-O-caffeoylquinic acid), neochlorogenic acid (5-O-Caffeoylquinic acid), cynarine (1,5-dicaffeoylquinic acid), 3,4-dicaffeoylquinic acid, and 3,5-dicaffeoylquinic acid.

In some embodiments, a pharmaceutical composition disclosed herein comprises one or more anti-oncogenic phytochemicals in an amount of, e.g., about 0.05%, about 0.1%, about 1%, about 2.5%, about 5%, about 7.5%, about 10%, about 12.5%, about 15%, about 17.5%, about 20%, about 22.5%, about 25%, about 30%, about 35%, about 40%, about 45%, or about 50% by weight. In one embodiment, a pharmaceutical composition disclosed herein comprises one or more anti-oncogenic phytochemicals in an amount of, e.g., at least 0.05%, at least 0.1%, at least 1%, at least 2.5%, at least 5%, at least 7.5%, at least 10%, at least 12.5%, at least 15%, at least 17.5%, at least 20%, at least 22.5%, at least 25%, at least 30%, at least 35%, at least 40%, at least 45%, or at least 50% by weight. In one embodiment, a pharmaceutical composition disclosed herein comprises one or more anti-oncogenic phytochemicals in an amount of, e.g., at most 0.05%, at most 0.1%, at most 1%, at most 2.5%, at most 5%, at most 7.5%, at most 10%, at most 12.5%, at most 15%, at most 17.5%, at most 20%, at most 22.5%, at most 25%, at most 30%, at most 35%, at most 40%, at most 45%, or at most 50% by weight.

In some embodiments, a pharmaceutical composition disclosed herein comprises one or more anti-oncogenic phytochemicals in an amount of, e.g., about 0.05% to about 1%, about 0.05% to about 2.5%, about 0.05% to about 5%, about 0.05% to about 7.5%, about 0.05% to about 10%, about 0.05% to about 12.5%, about 0.05% to about 15%, about 0.05% to about 17.5%, about 0.05% to about 20%, about 0.05% to about 22.5%, about 0.05% to about 25%, about 0.05% to about 30%, about 0.05% to about 40%, about 0.05% to about 50%, about 0.1% to about 1%, about 0.1% to about 2.5%, about 0.1% to about 5%, about 0.1% to about 7.5%, about 0.1% to about 10%, about 0.1% to about 12.5%, about 0.1% to about 15%, about 0.1% to about 17.5%, about 0.1% to about 20%, about 0.1% to about 22.5%, about 0.1% to about 25%, about 0.1% to about 30%, about 0.1% to about 40%, about 0.1% to about 50%, about 1% to about 2.5%, about 1% to about 5%, about 1% to about 7.5%, about 1% to about 10%, about 1% to about 12.5%, about 1% to about 15%, about 1% to about 17.5%, about 1% to about 20%, about 1% to about 22.5%, about 1% to about 25%, about 1% to about 30%, about 1% to about 40%, about 1% to about 50%, about 5% to about 10%, about 5% to about 20%, about 5% to about 30%, about 5% to about 40%, about 5% to about 50%, about 10% to about 20%, about 10% to about 30%, about 10% to about 40%, about 10% to about 50%, about 20% to about 30%, about 20% to about 40%, about 20% to about 50%, about 30% to about 40%, about 30% to about 50%, or about 40% to about 50% by weight.

In some embodiments, a pharmaceutical composition disclosed herein comprises one or more anti-oncogenic phytochemicals in a concentration of, e.g., about 0.01 mg/mL, about 0.025 mg/mL, about 0.05 mg/mL, about 0.075 mg/mL, about 0.1 mg/mL, about 0.15 mg/mL, about 0.2 mg/mL, about 0.25 mg/mL, about 0.3 mg/mL, about 0.35 mg/mL, about 0.4 mg/mL, about 0.45 mg/mL, about 0.5 mg/mL, about 0.55 mg/mL, about 0.6 mg/mL, about 0.65 mg/mL, about 0.7 mg/mL, about 0.75 mg/mL, about 0.8 mg/mL, about 0.85 mg/mL, about 0.9 mg/mL, about 0.95 mg/mL, about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 60 mg/mL, about 65 mg/mL, about 70 mg/mL, about 75 mg/mL, about 100 mg/mL, about 125 mg/mL, about 150 mg/mL, about 175 mg/mL, about 200 mg/mL, about 225 mg/mL, about 250 mg/mL, about 275 mg/mL, about 300 mg/mL, about 325 mg/mL, about 350 mg/mL, about 375 mg/mL, about 400 mg/mL, about 425 mg/mL, about 450 mg/mL, about 475 mg/mL, or about 500 mg/mL. In one embodiment, a pharmaceutical composition disclosed herein comprises one or more anti-oncogenic phytochemicals in a concentration of, e.g., at least 0.01 mg/mL, at least 0.025 mg/mL, at least 0.05 mg/mL, at least 0.075 mg/mL, at least 0.1 mg/mL, at least 0.15 mg/mL, at least 0.2 mg/mL, at least 0.25 mg/mL, at least 0.3 mg/mL, at least 0.35 mg/mL, at least 0.4 mg/mL, at least 0.45 mg/mL, at least 0.5 mg/mL, at least 0.55 mg/mL, at least 0.6 mg/mL, at least 0.65 mg/mL, at least 0.7 mg/mL, at least 0.75 mg/mL, at least 0.8 mg/mL, at least 0.85 mg/mL, at least 0.9 mg/mL, at least 0.95 mg/mL, at least 1 mg/mL, at least 5 mg/mL, at least 10 mg/mL, at least 15 mg/mL, at least 20 mg/mL, at least 25 mg/mL, at least 30 mg/mL, at least 35 mg/mL, at least 40 mg/mL, at least 45 mg/mL, at least 50 mg/mL, at least 60 mg/mL, at least 65 mg/mL, at least 70 mg/mL, at least 75 mg/mL, at least 100 mg/mL, at least 125 mg/mL, at least 150 mg/mL, at least 175 mg/mL, at least 200 mg/mL, at least 225 mg/mL, at least 250 mg/mL, at least 275 mg/mL, at least 300 mg/mL, at least 325 mg/mL, at least 350 mg/mL, at least 375 mg/mL, at least 400 mg/mL, at least 425 mg/mL, at least 450 mg/mL, at least 475 mg/mL, or at least 500 mg/mL. In one embodiment, a pharmaceutical composition disclosed herein comprises one or more anti-oncogenic phytochemicals in a concentration of, e.g., at most 0.01 mg/mL, at most 0.025 mg/mL, at most 0.05 mg/mL, at most 0.075 mg/mL, at most 0.1 mg/mL, at most 0.15 mg/mL, at most 0.2 mg/mL, at most 0.25 mg/mL, at most 0.3 mg/mL, at most 0.35 mg/mL, at most 0.4 mg/mL, at most 0.45 mg/mL, at most 0.5 mg/mL, at most 0.55 mg/mL, at most 0.6 mg/mL, at most 0.65 mg/mL, at most 0.7 mg/mL, at most 0.75 mg/mL, at most 0.8 mg/mL, at most 0.85 mg/mL, at most 0.9 mg/mL, at most 0.95 mg/mL, at most 1 mg/mL, at most 5 mg/mL, at most 10 mg/mL, at most 15 mg/mL, at most 20 mg/mL, at most 25 mg/mL, at most 30 mg/mL, at most 35 mg/mL, at most 40 mg/mL, at most 45 mg/mL, at most 50 mg/mL, at most 60 mg/mL, at most 65 mg/mL, at most 70 mg/mL, at most 75 mg/mL, at most 100 mg/mL, at most 125 mg/mL, at most 150 mg/mL, at most 175 mg/mL, at most 200 mg/mL, at most 225 mg/mL, at most 250 mg/mL, at most 275 mg/mL, at most 300 mg/mL, at most 325 mg/mL, at most 350 mg/mL, at most 375 mg/mL, at most 400 mg/mL, at most 425 mg/mL, at most 450 mg/mL, at most 475 mg/mL, or at most 500 mg/mL.

In some embodiments, a pharmaceutical composition disclosed herein comprises one or more anti-oncogenic phytochemicals in a concentration of, e.g., about 0.01 mg/mL to about 0.05 mg/mL, about 0.01 mg/mL to about 0.1 mg/mL, about 0.01 mg/mL to about 0.5 mg/mL, about 0.01 mg/mL to about 1 mg/mL, about 0.01 mg/mL to about 5 mg/mL, about 0.01 mg/mL to about 10 mg/mL, about 0.01 mg/mL to about 20 mg/mL, about 0.01 mg/mL to about 25 mg/mL, about 0.01 mg/mL to about 50 mg/mL, about 0.01 mg/mL to about 75 mg/mL, about 0.01 mg/mL to about 100 mg/mL, about 0.01 mg/mL to about 125 mg/mL, about 0.01 mg/mL to about 150 mg/mL, about 0.01 mg/mL to about 200 mg/mL, about 0.05 mg/mL to about 0.1 mg/mL, about 0.05 mg/mL to about 0.5 mg/mL, about 0.05 mg/mL to about 1 mg/mL, about 0.05 mg/mL to about 5 mg/mL, about 0.05 mg/mL to about 10 mg/mL, about 0.05 mg/mL to about 20 mg/mL, about 0.05 mg/mL to about 25 mg/mL, about 0.05 mg/mL to about 50 mg/mL, about 0.05 mg/mL to about 75 mg/mL, about 0.05 mg/mL to about 100 mg/mL, about 0.05 mg/mL to about 125 mg/mL, about 0.05 mg/mL to about 150 mg/mL, about 0.05 mg/mL to about 200 mg/mL, about 0.1 mg/mL to about 0.5 mg/mL, about 0.1 mg/mL to about 1 mg/mL, about 0.1 mg/mL to about 5 mg/mL, about 0.1 mg/mL to about 10 mg/mL, about 0.1 mg/mL to about 20 mg/mL, about 0.1 mg/mL to about 25 mg/mL, about 0.1 mg/mL to about 50 mg/mL, about 0.1 mg/mL to about 75 mg/mL, about 0.1 mg/mL to about 100 mg/mL, about 0.1 mg/mL to about 125 mg/mL, about 0.1 mg/mL to about 150 mg/mL, about 0.1 mg/mL to about 200 mg/mL, about 0.5 mg/mL to about 1 mg/mL, about 0.5 mg/mL to about 5 mg/mL, about 0.5 mg/mL to about 10 mg/mL, about 0.5 mg/mL to about 20 mg/mL, about 0.5 mg/mL to about 25 mg/mL, about 0.5 mg/mL to about 50 mg/mL, about 0.5 mg/mL to about 75 mg/mL, about 0.5 mg/mL to about 100 mg/mL, about 0.5 mg/mL to about 125 mg/mL, about 0.5 mg/mL to about 150 mg/mL, about 0.5 mg/mL to about 200 mg/mL, about 1 mg/mL to about 5 mg/mL, about 1 mg/mL to about 10 mg/mL, about 1 mg/mL to about 20 mg/mL, about 1 mg/mL to about 25 mg/mL, about 1 mg/mL to about 50 mg/mL, about 1 mg/mL to about 75 mg/mL, about 1 mg/mL to about 100 mg/mL, about 1 mg/mL to about 125 mg/mL, about 1 mg/mL to about 150 mg/mL, about 1 mg/mL to about 200 mg/mL, about 5 mg/mL to about 10 mg/mL, about 5 mg/mL to about 20 mg/mL, about 5 mg/mL to about 25 mg/mL, about 5 mg/mL to about 50 mg/mL, about 5 mg/mL to about 75 mg/mL, about 5 mg/mL to about 100 mg/mL, about 5 mg/mL to about 125 mg/mL, about 5 mg/mL to about 150 mg/mL, about 5 mg/mL to about 200 mg/mL, about 10 mg/mL to about 20 mg/mL, about 10 mg/mL to about 25 mg/mL, about 10 mg/mL to about 50 mg/mL, about 10 mg/mL to about 75 mg/mL, about 10 mg/mL to about 100 mg/mL, about 10 mg/mL to about 125 mg/mL, about 10 mg/mL to about 150 mg/mL, about 10 mg/mL to about 200 mg/mL, about 25 mg/mL to about 50 mg/mL, about 25 mg/mL to about 75 mg/mL, about 25 mg/mL to about 100 mg/mL, about 25 mg/mL to about 125 mg/mL, about 25 mg/mL to about 150 mg/mL, about 25 mg/mL to about 200 mg/mL, about 50 mg/mL to about 100 mg/mL, about 50 mg/mL to about 150 mg/mL, about 50 mg/mL to about 200 mg/mL, about 75 mg/mL to about 100 mg/mL, about 75 mg/mL to about 150 mg/mL, about 75 mg/mL to about 200 mg/mL, about 100 mg/mL to about 150 mg/mL, about 100 mg/mL to about 200 mg/mL, about 125 mg/mL to about 150 mg/mL, about 125 mg/mL to about 200 mg/mL, about 150 mg/mL to about 200 mg/mL.

In some embodiments, a pharmaceutical composition disclosed herein comprises one or more anti-oncogenic phytochemicals in a concentration of, e.g., about 5 mg/mL to about 20 mg/mL, about 5 mg/mL to about 25 mg/mL, about 5 mg/mL to about 50 mg/mL, about 5 mg/mL to about 75 mg/mL, about 5 mg/mL to about 100 mg/mL, about 5 mg/mL to about 125 mg/mL, about 5 mg/mL to about 150 mg/mL, about 5 mg/mL to about 175 mg/mL, about 5 mg/mL to about 200 mg/mL, about 5 mg/mL to about 225 mg/mL, about 5 mg/mL to about 250 mg/mL, about 5 mg/mL to about 275 mg/mL, about 5 mg/mL to about 300 mg/mL, about 5 mg/mL to about 325 mg/mL, about 5 mg/mL to about 350 mg/mL, about 5 mg/mL to about 375 mg/mL, about 5 mg/mL to about 400 mg/mL, about 5 mg/mL to about 425 mg/mL, about 5 mg/mL to about 450 mg/mL, about 5 mg/mL to about 475 mg/mL, about 5 mg/mL to about 500 mg/mL, about 10 mg/mL to about 20 mg/mL, about 10 mg/mL to about 25 mg/mL, about 10 mg/mL to about 50 mg/mL, about 10 mg/mL to about 75 mg/mL, about 10 mg/mL to about 100 mg/mL, about 10 mg/mL to about 125 mg/mL, about 10 mg/mL to about 150 mg/mL, about 10 mg/mL to about 175 mg/mL, about 10 mg/mL to about 200 mg/mL, about 10 mg/mL to about 225 mg/mL, about 10 mg/mL to about 250 mg/mL, about 10 mg/mL to about 275 mg/mL, about 10 mg/mL to about 300 mg/mL, about 10 mg/mL to about 325 mg/mL, about 10 mg/mL to about 350 mg/mL, about 10 mg/mL to about 375 mg/mL, about 10 mg/mL to about 400 mg/mL, about 10 mg/mL to about 425 mg/mL, about 10 mg/mL to about 450 mg/mL, about 10 mg/mL to about 475 mg/mL, about 10 mg/mL to about 500 mg/mL, about 25 mg/mL to about 50 mg/mL, about 25 mg/mL to about 75 mg/mL, about 25 mg/mL to about 100 mg/mL, about 25 mg/mL to about 125 mg/mL, about 25 mg/mL to about 150 mg/mL, about 25 mg/mL to about 175 mg/mL, about 25 mg/mL to about 200 mg/mL, about 25 mg/mL to about 225 mg/mL, about 25 mg/mL to about 250 mg/mL, about 25 mg/mL to about 275 mg/mL, about 25 mg/mL to about 300 mg/mL, about 25 mg/mL to about 325 mg/mL, about 25 mg/mL to about 350 mg/mL, about 25 mg/mL to about 375 mg/mL, about 25 mg/mL to about 400 mg/mL, about 25 mg/mL to about 425 mg/mL, about 25 mg/mL to about 450 mg/mL, about 25 mg/mL to about 475 mg/mL, about 25 mg/mL to about 500 mg/mL, about 50 mg/mL to about 75 mg/mL, about 50 mg/mL to about 100 mg/mL, about 50 mg/mL to about 125 mg/mL, about 50 mg/mL to about 150 mg/mL, about 50 mg/mL to about 175 mg/mL, about 50 mg/mL to about 200 mg/mL, about 50 mg/mL to about 225 mg/mL, about 50 mg/mL to about 250 mg/mL, about 50 mg/mL to about 275 mg/mL, about 50 mg/mL to about 300 mg/mL, about 50 mg/mL to about 325 mg/mL, about 50 mg/mL to about 350 mg/mL, about 50 mg/mL to about 375 mg/mL, about 50 mg/mL to about 400 mg/mL, about 50 mg/mL to about 425 mg/mL, about 50 mg/mL to about 450 mg/mL, about 50 mg/mL to about 475 mg/mL, about 50 mg/mL to about 500 mg/mL, about 75 mg/mL to about 100 mg/mL, about 75 mg/mL to about 125 mg/mL, about 75 mg/mL to about 150 mg/mL, about 75 mg/mL to about 175 mg/mL, about 75 mg/mL to about 200 mg/mL, about 75 mg/mL to about 225 mg/mL, about 75 mg/mL to about 250 mg/mL, about 75 mg/mL to about 275 mg/mL, about 75 mg/mL to about 300 mg/mL, about 75 mg/mL to about 325 mg/mL, about 75 mg/mL to about 350 mg/mL, about 75 mg/mL to about 375 mg/mL, about 75 mg/mL to about 400 mg/mL, about 75 mg/mL to about 425 mg/mL, about 75 mg/mL to about 450 mg/mL, about 75 mg/mL to about 475 mg/mL, about 75 mg/mL to about 500 mg/mL, about 100 mg/mL to about 125 mg/mL, about 100 mg/mL to about 150 mg/mL, about 100 mg/mL to about 175 mg/mL, about 100 mg/mL to about 200 mg/mL, about 100 mg/mL to about 225 mg/mL, about 100 mg/mL to about 250 mg/mL, about 100 mg/mL to about 275 mg/mL, about 100 mg/mL to about 300 mg/mL, about 100 mg/mL to about 325 mg/mL, about 100 mg/mL to about 350 mg/mL, about 100 mg/mL to about 375 mg/mL, about 100 mg/mL to about 400 mg/mL, about 100 mg/mL to about 425 mg/mL, about 100 mg/mL to about 450 mg/mL, about 100 mg/mL to about 475 mg/mL, or about 100 mg/mL to about 500 mg/mL.

Aspects of the present specification disclose methods of preparing a pharmaceutical composition disclosed herein comprising one or more anti-oncogenic phytochemicals. In some embodiments, a method of preparing a pharmaceutical composition disclosed herein comprises the steps of preparing a macerate comprising a solvent and a plant material from one or more plant species belonging to the family Asteraceae; incubating the macerate for a period of time in order to solubilize the one or more anti-oncogenic phytochemicals; and purifying the macerate to produce the pharmaceutical composition comprising one or more anti-oncogenic phytochemicals. In some embodiments, before preparing a macerate, a disclosed method further comprises a step of processing the plant material from the one or more plant species. In some embodiments, before processing the plant material, a disclosed method further comprises a step of collecting one or more plants of the one or more plant species.

Macerate preparation comprising adding a plant material to a solvent. The amount of plant material and solvent added can be any amount so long as sufficient plant material is added to enable adequate amounts of one or more anti-oncogenic phytochemicals to be solubilized or otherwise extracted from the plant material. In some embodiments, preparing a macerate comprising adding a plant material to a solvent in a g/L ratio of between 10:100 to 40:100. In some embodiments, preparing a macerate comprising adding a plant material to a solvent in a g/L ratio of between 15:100 to 35:100. In some embodiments, preparing a macerate comprising adding a plant material to a solvent in a g/L ratio of between 20:100 to 30:100. In some embodiments, preparing a macerate comprising adding a plant material to a solvent in a g/L ratio of between 25:100.

A solvent used in preparation of a macerate can be any solvent that sufficiently solubilizes or otherwise extracts one or more anti-oncogenic phytochemicals from a plant material. In some embodiments, a solvent comprises a pharmaceutically acceptable solvent. In some embodiments, a solvent comprises a pharmaceutically acceptable monohydric alcohol. In some embodiments, a solvent comprises ethanol, 1-propanol, 2-propanol, isobutanol, tert-amyl alcohol, or any combination thereof.

A solvent can be added in an undiluted or diluted solution so long as the undiluted or diluted solution can sufficiently solubilize or otherwise extract one or more anti-oncogenic phytochemicals from a plant material. In some embodiments, a solvent used in preparation of a macerate is added without prior dilution, i.e., a solution of 100% solvent. In some embodiments, a solvent used in preparation of a macerate can be prior diluted. In some embodiments, a solvent is prior mixed with a diluent to produce a solution comprising 70% to 99% solvent. In some embodiments, a solvent is prior mixed with a diluent to produce a solution comprising 80% to 98% solvent. In some embodiments, a solvent is prior mixed with a diluent to produce a solution comprising 85% to 95% solvent. In some embodiments, a solvent is prior mixed with a diluent to produce a solution comprising 88% to 92% solvent.

In some embodiments, a solvent comprising 70% to 100% of a pharmaceutically acceptable monohydric alcohol. In some embodiments, a solvent comprising 80% to 100% of a pharmaceutically acceptable monohydric alcohol. In some embodiments, a solvent comprising 85% to 100% of a pharmaceutically acceptable monohydric alcohol. In some embodiments, a solvent comprising 85% to 95% of a pharmaceutically acceptable monohydric alcohol. In some embodiments, a solvent comprising 88% to 92% of a pharmaceutically acceptable monohydric alcohol. In these embodiments, a pharmaceutically acceptable monohydric alcohol comprises ethanol, 1-propanol, 2-propanol, isobutanol, tert-amyl alcohol, or any combination thereof.

A solvent can be added to a macerate at a temperature sufficient to solubilize or otherwise extract one or more anti-oncogenic phytochemicals from the plant material. In some embodiments, a solvent can be added to a macerate at room temperature, such as, e.g., 15° C. to 22° C. In some embodiments, a solvent can be added to a macerate at elevated temperature in order to facilitate solubilization/extraction of one or more anti-oncogenic phytochemicals from a plant material. In some embodiments, a solvent can be added to a macerate at a temperature between 60° C. to 130° C. In some embodiments, a solvent can be added to a macerate at a temperature between 70° C. to 120° C. In some embodiments, a solvent can be added to a macerate at a temperature between 80° C. to 110° C. In some embodiments, a solvent can be added to a macerate at a temperature between 90° C. to 100° C. In some embodiments, a solvent can be added to a macerate at a temperature between 94° C. to 98° C.

A plant material is any plant material comprising one or more anti-oncogenic phytochemicals disclosed herein. In some embodiments, plant material can be obtained from one or more plant species belonging to the plant family Asteraceae. In some embodiments, plant material can be obtained from one or more plant species belonging to the plant subfamily Asteroideae. In some embodiments, plant material can be obtained from one or more plant species belonging to the plant supertribe Asterodae. In some embodiments, plant material can be obtained from one or more plant species belonging to the plant tribe Astereae. In some embodiments, plant material can be obtained from one or more plant species belonging to the plant genus *Baccharis*. In some embodiments, plant material can be obtained from *Baccharis artemisioides, Baccharis coridifolia*, or *Baccharis dracunculifolia*.

A plant material disclosed herein is any part of a plant containing sufficient amounts of one or more anti-oncogenic phytochemicals that can be solubilized or otherwise extracted by a method disclosed herein. Non-limiting examples of a plant part include stems, leaves, flowers, seeds, and roots. In some embodiments, a plant material comprises, consists essentially of, or consists of leaves.

A plant material can be processed in order to facilitate solubilization/extraction of one or more anti-oncogenic phytochemicals from the plant material. In some embodiments, a plant material is processed by chopping, dicing, mincing, shredding, or otherwise cutting the plant material into pieces sufficiently small enough to facilitate solubilization/extraction of one or more anti-oncogenic phytochemicals from the plant material. In some embodiments, a plant material is processed into pieces ranging between 0.1 $cm^2$ to 3 $cm^2$ in size. In some embodiments, a plant material is processed into pieces ranging between 0.25 $cm^2$ to 2.5 $cm^2$ in size. In some embodiments, a plant material is processed into pieces ranging between 0.5 $cm^2$ to 2 $cm^2$ in size. In some embodiments, a plant material is processed into pieces ranging between 1 $cm^2$ to 2 $cm^2$ in size. In some embodiments, a plant material is weighted after the material has been processed.

Maceration is typically performed by adding a plant material and solvent in a closed container of sufficient size to hold the macerate and provide sufficient room to facilitate mixing of the components during incubation. In some embodiments, a closed container is an air-tight container. In some embodiments, a closed container is an air-tight and light-tight container.

A macerate comprising a plant material and solvent is incubated for a period of time sufficient to solubilize or otherwise extract one or more anti-oncogenic phytochemicals from the plant material. In some embodiments, a macerate comprising a plant material and solvent can be incubated for at least 7 days, at least 14 days, at least 21 days, at least 28 days, at least 35 days, or at least 42 days. In some embodiments, a macerate comprising a plant material and solvent can be incubated for at most 7 days, at most 14 days, at most 21 days, at most 28 days, at most 35 days, or at most 42 days. In some embodiments, a macerate comprising a plant material and solvent can be incubated for about 14 days to about 42 days. In some embodiments, a macerate comprising a plant material and solvent can be incubated for about 21 days to about 35 days. In some embodiments, a macerate comprising a plant material and solvent can be incubated for about 26 days to about 30 days.

A macerate comprising a plant material and solvent is incubated at a temperature sufficient to solubilize or otherwise extract one or more anti-oncogenic phytochemicals from the plant material. In some embodiments, a macerate comprising a plant material and solvent can be incubated at room temperature, such as, e.g., about 15° C. to about 22° C. In some embodiments, a macerate comprising a plant material and solvent can be incubated in the dark at room temperature, such as, e.g., about 15° C. to about 22° C. In some embodiments, a macerate comprising a plant material and solvent can be incubated at an elevated temperature, such as, e.g., about 35° C. to about 37° C. In some embodiments, a macerate comprising a plant material and solvent can be incubated in the dark at an elevated temperature, such as, e.g., about 35° C. to about 37° C.

After maceration, the macerate can be purified to remove the solid plant material. In some embodiments, purification comprises one or more filtrations. In some embodiments, purification comprises one or more filtrations including filtering the incubated macerate thought a press to remove bulk plant material and collecting the resulting press elute. In some embodiments, purification comprises one or more filtrations including filtering the incubated macerate thought a filter medium to remove fine particulate matter and collecting the resulting filtered elute. In some embodiments, purification comprises one or more filtrations including filtering the incubated macerate thought a press to remove bulk plant material and collecting the resulting press elute and then filtering the press elute thought a filter medium to remove fine particulate matter and collecting the resulting filtered elute.

In some embodiments, purification comprises one or more filtrations directly results in an extract comprising one or more anti-oncogenic phytochemicals. In some embodiments, an extract comprising one or more anti-oncogenic phytochemicals can be aliquoted into brown glass bottles and stored in the dark at room temperature, such as, e.g., about 15° C. to about 22° C. In some embodiments, an extract comprising one or more anti-oncogenic phytochemicals can be formulated into a pharmaceutical composition disclosed herein or medicament disclosed herein.

In some embodiments, purification comprises one or more filtrations directly results in a pharmaceutical composition comprising one or more anti-oncogenic phytochemicals. In some embodiments, a pharmaceutical composition comprising one or more anti-oncogenic phytochemicals can be aliquoted into brown glass bottles and stored in the dark at room temperature, such as, e.g., about 15° C. to about 22° C. In some embodiments, a pharmaceutical composition comprising one or more anti-oncogenic phytochemicals produced by a method of preparation disclosed herein can be used in preclinical and clinical studies.

In some embodiments, purification comprises one or more filtrations directly results in a medicament comprising one or more anti-oncogenic phytochemicals. In some embodiments, a medicament comprising one or more anti-oncogenic phytochemicals can be aliquoted into brown glass bottles and stored in the dark at room temperature, such as, e.g., about 15° C. to about 22° C. In some embodiments, a medicament comprising one or more anti-oncogenic phytochemicals produced by a method of preparation disclosed herein can be used in preclinical and clinical studies.

A method of preparation disclosed herein can further comprise a step of processing a plant material from one or more plant species. Such processing step facilitates removal of unwanted plant parts as well as debris and other foreign material. In some embodiments, one or more plants are processed by removing bulk debris I, such as, e.g., clumps of soil, other plants, and weeds, as well as other bulk contaminants and other foreign material as well as other bulk materials non-suitable for a method of preparation disclosed herein. In some embodiments, one or more plants are processed by washing in an appropriate wash solution to separate plant material from particulate debris, such as, e.g., soil, insects, pesticides, fine contaminants, as well as other materials non-suitable for a method of preparation disclosed herein and/or the resulting extracts disclosed herein, pharmaceutical compositions disclosed herein, and/or medicaments disclosed herein, and drying washed plants with an absorbent material. In some embodiments, one or more plants are processed to enrich for plant material comprising one or more anti-oncogenic phytochemicals disclosed herein, such as, e.g., sorting for desired plant parts that are the source of the plant material disclosed herein and/or removing unwanted plant parts. In some embodiments, one or more plants are processed by removing and setting aside the leaves of one or more plants and discarding the flowers, stems, and roots of the one or more plants.

In some embodiments, one or more plants are processed by removing bulk debris and washing to separate particulate debris. In some embodiments, one or more plants are processed by removing bulk debris and enriching for plant material comprising one or more anti-oncogenic phytochemicals disclosed herein. In some embodiments, one or more plants are processed by removing bulk debris and enriching for leaves comprising one or more anti-oncogenic phytochemicals disclosed herein. In some embodiments, one or more plants are processed by removing bulk debris, washing to separate particulate debris, and enriching for plant material comprising one or more anti-oncogenic phytochemicals disclosed herein. In some embodiments, one or more plants are processed by removing bulk debris, washing to separate particulate debris, and enriching for leaves comprising one or more anti-oncogenic phytochemicals disclosed herein.

In some embodiments, one or more plants are processed by enriching for plant material comprising one or more anti-oncogenic phytochemicals and optionally removing bulk and particulate debris. In some embodiments, one or more plants are processed by enriching for leaves comprising one or more anti-oncogenic phytochemicals disclosed herein and optionally removing bulk and particulate debris.

A method of preparation disclosed herein can further comprise a step of collecting one or more plants of the one or more plant species. In some embodiments, one or more plants disclosed herein can be grown in a controlled environment like a green house. In some embodiments, one or more plants disclosed herein can be grown in a filed or other agricultural land. Collection of one or more plants disclosed herein can be by manual harvest or through the use of harvesting machinery.

Aspects of the present specification disclose an extract comprising one or more anti-oncogenic phytochemicals produced by a method of preparation disclosed herein.

Aspects of the present specification disclose a pharmaceutical composition comprising one or more anti-oncogenic phytochemicals produced by a method of preparation disclosed herein.

Aspects of the present specification disclose a medicament comprising one or more anti-oncogenic phytochemicals produced by a method of preparation disclosed herein.

Aspects of the present specification disclose methods of treating a neoplasm in an individual in need thereof. In some embodiments, a method of treatment disclosed herein comprises administering an effective amount of an extract comprising one or more anti-oncogenic phytochemicals disclosed herein to the individual. In some embodiments, a method of treatment disclosed herein comprises administering an effective amount of a pharmaceutical composition comprising one or more anti-oncogenic phytochemicals disclosed herein to the individual. In some embodiments, a method of treatment disclosed herein comprises administering an effective amount of a medicament comprising one or more anti-oncogenic phytochemicals disclosed herein to the individual.

Aspects of the present specification disclose methods of treating a cancer in an individual in need thereof. In some embodiments, a method of treatment disclosed herein comprises administering an effective amount of an extract comprising one or more anti-oncogenic phytochemicals disclosed herein to the individual. In some embodiments, a method of treatment disclosed herein comprises administering an effective amount of a pharmaceutical composition comprising one or more anti-oncogenic phytochemicals disclosed herein to the individual. In some embodiments, a method of treatment disclosed herein comprises administering an effective amount of a medicament comprising one or more anti-oncogenic phytochemicals disclosed herein to the individual.

A method or use of treating a cancer is performed to an individual. An individual is typically a human being, but can be an animal, including, but not limited to, dogs, cats, birds, cattle, horses, sheep, goats, reptiles, and other animals, whether domesticated or not. Typically, any individual who is a candidate for treatment is a candidate with some form of cancer, whether the cancer is benign or malignant, a tumor, solid or otherwise, a cancer not located within a tumor or some other form of cancer. Pre-operative evaluation typically includes routine history and physical examination in addition to thorough informed consent disclosing all relevant risks and benefits of the procedure.

An extract disclosed herein, a pharmaceutical composition disclosed herein, and a medicament disclosed herein are typically administered in a therapeutically effective amount. As used herein, the term "effective amount" is synonymous with "therapeutically effective amount", "effective dose", or "therapeutically effective dose". In some embodiments, therapeutically effective amount is the minimum dose of one or more anti-oncogenic phytochemicals disclosed herein necessary to achieve the desired therapeutic effect in a cancer treatment, and includes a dose sufficient reduce or eliminate the availability of cellular energy required by cancer cells to maintain their viability, reduce or eliminate the availability of material resources required by cancer cells to maintain their viability, reduce or eliminate the bioavailability of glucose required by cancer cells to maintain their viability, reduce or eliminate the bioavailability of lipids, including fats and cholesterol, required by cancer cells to maintain their viability, reduce or inhibit glycolysis in cancer cells, reduce or inhibit glucose uptake by cancer cells, reduce or inhibit lipid uptake by cancer cells, reduce or inhibit cell division of cancer cells, reduce or inhibit cell growth of cancer cells, promote or enhance mitochondrial-directed apoptosis in cancer cells, promote or enhance death of cancer cells, or any combination thereof. The effectiveness of one or more anti-oncogenic phytochemicals disclosed herein can be determined by observing an improvement in an individual based upon one or more clinical symptoms, and/or physiological indicators associated with treating cancer in an individual. An improvement in an individual with cancer can also be indicated by a reduced need for a concurrent therapy.

The appropriate effective amount of one or more anti-oncogenic phytochemicals disclosed herein to be administered to treat a cancer of an individual can be determined by a person of ordinary skill in the art by taking into account factors, including, without limitation, the type of cancer, the particular physiological conditions or symptoms associated with the cancer, the cause of the cancer, the severity of the cancer, the degree of relief desired for the cancer, the duration of relief desired for the cancer, the particular one or more anti-oncogenic phytochemicals disclosed herein used, the pharmacokinetic characteristics of the particular one or more anti-oncogenic phytochemicals disclosed herein used including liberation, absorption, distribution, metabolism, and excretion, the pharmacodynamic characteristics of the particular one or more anti-oncogenic phytochemicals disclosed herein used including mechanism of action, dose-response relationship, desired activity, undesirable side effects, therapeutic window and duration of action, the frequency of administration, the particular route of administration used, the use and type of concurrent therapy, the use and type of other cancer drugs, the particular characteristics, history and risk factors of the individual, such as, e.g., age, weight, general health and the like, or any combination thereof. It is known by a person of ordinary skill in the art that an effective amount of one or more anti-oncogenic phytochemicals disclosed herein can be extrapolated from in-vitro assays and in-vivo administration studies using animal models prior to administration to humans. In addition, variations in the necessary effective amount are to be expected in view of the differing efficiencies of the various routes of administration. For instance, oral administration of one or more anti-oncogenic phytochemicals disclosed herein generally would be expected to require higher dosage levels than intravenous administration. Similarly, systemic administration of one or more anti-oncogenic phytochemicals disclosed herein would be expected to require higher dosage levels than a local administration. Variations in these dosage levels can be adjusted using standard empirical routines of optimization, which are well-known to a person of ordinary skill in the art. One skilled in the art will also recognize that the condition of the individual can be monitored throughout the course of a method or use disclosed herein and that the effective amount of one or more anti-oncogenic phytochemicals disclosed herein that is administered can be adjusted accordingly. Thus, the precise therapeutically effective dosage levels and patterns are preferably determined by the attending healthcare professional in consideration of the above-identified factors.

In some embodiments, a therapeutically effective amount of one or more anti-oncogenic phytochemicals disclosed herein generally is in the range of about 0.01 mg/kg to about 10 mg/kg. In aspects of these embodiments, an effective amount of one or more anti-oncogenic phytochemicals disclosed herein may be, e.g., at least 0.01 mg/kg, at least 0.05 mg/kg, at least 0.1 mg/kg, at least 0.5 mg/kg, at least 1.0 mg/kg, at least 2.0 mg/kg, at least 3.0 mg/kg, at least 4.0 mg/kg, at least 5.0 mg/kg, at least 6.0 mg/kg, at least 7.0 mg/kg, at least 8.0 mg/kg, at least 9.0 mg/kg, or at least 10 mg/kg. In other aspects of these embodiments, an effective amount of one or more anti-oncogenic phytochemicals disclosed herein may be, e.g., at most 0.01 mg/kg, at most 0.05 mg/kg, at most 0.1 mg/kg, at most 0.5 mg/kg, at most 1.0 mg/kg, at most 2.0 mg/kg, at most 3.0 mg/kg, at most 4.0 mg/kg, at most 5.0 mg/kg, at most 6.0 mg/kg, at most 7.0 mg/kg, at most 8.0 mg/kg, at most 9.0 mg/kg, or at most 10 mg/kg. In yet other aspects of these embodiments, an effective amount of one or more anti-oncogenic phytochemicals disclosed herein may be in the range of, e.g., about 0.01 mg/kg to about 0.05 mg/kg, about 0.01 mg/kg to about 0.1 mg/kg, about 0.01 mg/kg to about 0.5 mg/kg, about 0.01 mg/kg to about 1.0 mg/kg, about 0.01 mg/kg to about 2.0 mg/kg, about 0.01 mg/kg to about 3.0 mg/kg, about 0.01 mg/kg to about 4.0 mg/kg, about 0.01 mg/kg to about 5.0 mg/kg, about 0.01 mg/kg to about 6.0 mg/kg, about 0.01 mg/kg to about 7.0 mg/kg, about 0.01 mg/kg to about 8.0 mg/kg, about 0.01 mg/kg to about 9.0 mg/kg, about 0.01 mg/kg to about 10 mg/kg, about 0.1 mg/kg to about 0.5 mg/kg, about 0.1 mg/kg to about 1.0 mg/kg, about 0.1 mg/kg to about 2.0 mg/kg, about 0.1 mg/kg to about 3.0 mg/kg, about 0.1 mg/kg to about 4.0 mg/kg, about 0.1 mg/kg to about 5.0 mg/kg, about 0.1 mg/kg to about 6.0 mg/kg, about 0.1 mg/kg to about 7.0 mg/kg, about 0.1 mg/kg to about 8.0 mg/kg, about 0.1 mg/kg to about 9.0 mg/kg, about 0.1 mg/kg to about 10 mg/kg, about 0.5 mg/kg to about 1.0 mg/kg, about 0.5 mg/kg to about 2.0 mg/kg, about 0.5 mg/kg to about 3.0 mg/kg, about 0.5 mg/kg to about 4.0 mg/kg, about 0.5 mg/kg to about 5.0 mg/kg, about 0.5 mg/kg to about 6.0 mg/kg, about 0.5 mg/kg to about 7.0 mg/kg, about 0.5 mg/kg to about 8.0 mg/kg, about 0.5 mg/kg to about 9.0 mg/kg, about 0.5 mg/kg to about 10 mg/kg, about 1.0 mg/kg to about 2.0 mg/kg, about 1.0 mg/kg to about 3.0 mg/kg, about 1.0 mg/kg to about 4.0 mg/kg, about 1.0 mg/kg to about 5.0 mg/kg, about 1.0 mg/kg to about 6.0 mg/kg, about 1.0 mg/kg to about 7.0 mg/kg, about 1.0 mg/kg to about 8.0 mg/kg, about 1.0 mg/kg to about 9.0 mg/kg, or about 1.0 mg/kg to about 10 mg/kg.

In some embodiments, a therapeutically effective amount of one or more anti-oncogenic phytochemicals disclosed herein generally is in the range of about 0.01 mg/kg/day to about 10 mg/kg/day. In aspects of these embodiments, an effective amount of one or more anti-oncogenic phytochemicals disclosed herein may be, e.g., at least 0.01 mg/kg/day, at least 0.05 mg/kg/day, at least 0.1 mg/kg/day, at least 0.5 mg/kg/day, at least 1.0 mg/kg/day, at least 2.0 mg/kg/day, at least 3.0 mg/kg/day, at least 4.0 mg/kg/day, at least 5.0 mg/kg/day, at least 6.0 mg/kg/day, at least 7.0 mg/kg/day, at least 8.0 mg/kg/day, at least 9.0 mg/kg/day, or at least 10 mg/kg/day. In other aspects of these embodiments, an effective amount of one or more anti-oncogenic phytochemicals disclosed herein may be, e.g., at most 0.01 mg/kg/day, at most 0.05 mg/kg/day, at most 0.1 mg/kg/day, at most 0.5 mg/kg/day, at most 1.0 mg/kg/day, at most 2.0 mg/kg/day, at most 3.0 mg/kg/day, at most 4.0 mg/kg/day, at most 5.0 mg/kg/day, at most 6.0 mg/kg/day, at most 7.0 mg/kg/day, at most 8.0 mg/kg/day, at most 9.0 mg/kg/day, or at most 10 mg/kg/day. In yet other aspects of these embodiments, an effective amount of one or more anti-oncogenic phytochemicals disclosed herein may be in the range of, e.g., about 0.01 mg/kg/day to about 0.05 mg/kg/day, about 0.01 mg/kg/day to about 0.1 mg/kg/day, about 0.01 mg/kg/day to about 0.5 mg/kg/day, about 0.01 mg/kg/day to about 1.0 mg/kg/day, about 0.01 mg/kg/day to about 2.0 mg/kg/day, about 0.01 mg/kg/day to about 3.0 mg/kg/day, about 0.01 mg/kg/day to about 4.0 mg/kg/day, about 0.01 mg/kg/day to about 5.0 mg/kg/day, about 0.01 mg/kg/day to about 6.0 mg/kg/day, about 0.01 mg/kg/day to about 7.0 mg/kg/day, about 0.01 mg/kg/day to about 8.0 mg/kg/day, about 0.01 mg/kg/day to about 9.0 mg/kg/day, about 0.01 mg/kg/day to about 10 mg/kg/day, about 0.1 mg/kg/day to about 0.5 mg/kg/day, about 0.1 mg/kg/day to about 1.0 mg/kg/day, about 0.1 mg/kg/day to about 2.0 mg/kg/day, about 0.1 mg/kg/day to about 3.0 mg/kg/day, about 0.1 mg/kg/day to about 4.0 mg/kg/day, about 0.1 mg/kg/day to about 5.0 mg/kg/day, about 0.1 mg/kg/day to about 6.0 mg/kg/day, about 0.1 mg/kg/day to about 7.0 mg/kg/day, about 0.1 mg/kg/day to about 8.0 mg/kg/day, about 0.1 mg/kg/day to about 9.0 mg/kg/day, about 0.1 mg/kg/day to about 10 mg/kg/day, about 0.5 mg/kg/day to about 1.0 mg/kg/day, about 0.5 mg/kg/day to about 2.0 mg/kg/day, about 0.5 mg/kg/day to about 3.0 mg/kg/day, about 0.5 mg/kg/day to about 4.0 mg/kg/day, about 0.5 mg/kg/day to about 5.0 mg/kg/day, about 0.5 mg/kg/day to about 6.0 mg/kg/day, about 0.5 mg/kg/day to about 7.0 mg/kg/day, about 0.5 mg/kg/day to about 8.0 mg/kg/day, about 0.5 mg/kg/day to about 9.0 mg/kg/day, about 0.5 mg/kg/day to about 10 mg/kg/day, about 1.0 mg/kg/day to about 2.0 mg/kg/day, about 1.0 mg/kg/day to about 3.0 mg/kg/day, about 1.0 mg/kg/day to about 4.0 mg/kg/day, about 1.0 mg/kg/day to about 5.0 mg/kg/day, about 1.0 mg/kg/day to about 6.0 mg/kg/day, about 1.0 mg/kg/day to about 7.0 mg/kg/day, about 1.0 mg/kg/day to about 8.0 mg/kg/day, about 1.0 mg/kg/day to about 9.0 mg/kg/day, or about 1.0 mg/kg/day to about 10 mg/kg/day.

Dosing can be single dosage or cumulative (serial dosing), and can be readily determined by one skilled in the art. For instance, treatment of a cancer may comprise a one-time administration of an effective dose of a pharmaceutical composition or medicament disclosed herein. Alternatively, treatment of a chronic cancer may comprise multiple administrations of an effective dose of a pharmaceutical composition or medicament disclosed herein carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition or medicament disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition or medicament disclosed herein that is administered can be adjusted accordingly.

Aspects of the present specification disclose, in part, a neoplasm. Neoplasms can be divided into four main groups: benign neoplasms, in situ neoplasms, malignant neoplasms, and neoplasms of uncertain or unknown behavior. A neoplasm can be benign, potentially malignant, or malignant (i.e., cancer). A benign neoplasm include uterine fibroids, osteophytes, and melanocytic nevi (skin moles). Potentially malignant neoplasms are localized, do not invade, or destroy surrounding tissue but have the potential to transform into a malignant neoplasm. Potentially malignant neoplasms include carcinoma in situ. Malignant neoplasms are commonly called cancer. They invade and destroy the surrounding tissue, may metastasis and, if untreated or unresponsive to treatment, will generally prove fatal. Secondary neoplasm refers to any of a class of cancer that is either a metastatic offshoot of a primary tumor, or an apparently unrelated tumor that increases in frequency following certain cancer treatments such as chemotherapy or radiotherapy. Rarely there can be a metastatic neoplasm with no known site of the primary cancer and this is classed as a cancer of unknown primary origin.

Aspects of the present specification disclose, in part, a cancer. Cancer, or malignant neoplasm, is a large group of diseases involving uncontrolled growth and division of abnormal cells. A cancer can be a primary cancer, the initial or original malignant neoplastic disease, or a metastatic cancer, a malignant neoplasm deriving from a primary cancer that spread or invaded to other parts of the body cause new malignant neoplasms. A cancer can be a solid tumor comprising an abnormal mass of tissue that usually does not contain cysts or liquid areas, or a non-solid (blood) tumor, malignant neoplasms lacking mass.

Cancers are classified by the type of cell that the tumor cells resemble and is therefore presumed to be the origin of the tumor. These types include carcinomas, sarcomas, lymphomas and leukemias, germ cell tumors, and blastomas. A carcinoma is malignancy arising from epithelial cells, including the epithelial lining that covers the surface of internal organs and glands. This group includes many of the most common cancers and include nearly all those in the bladder, brain, breast, cervical, colon, endometrium, kidney, liver, lung, ovarian, pancreas prostate, rectum, skin, small intestine, stomach, thyroid, and uterus. A sarcoma is malignancy arising from mesenchymal cells and include neoplasms derived from connective tissue such as, e.g., bone, cartilage, fat, nervous, and vascular tissue. A lymphoma or leukemia is malignancy arising from hematopoietic (blood-forming) cells that leave the marrow and tend to mature in the lymph nodes (lymphoma) and blood (leukemia). A germ cell tumor is malignancy arising from pluripotent cells, most often presenting in the testicle or the ovary (seminoma and dysgerminoma, respectively). A blastoma is malignancy arising from immature "precursor" cells or embryonic tissue.

Non-limiting examples of a cancer, whether a primary cancer or a metastatic cancer, include a basil-cell skin cancer, a bladder cancer, a brain cancer, a breast cancer, a cervical cancer, a colon cancer, an endometrial cancer, a glioblastoma, a Hodgkin's lymphoma, a non-Hodgkin's lymphoma, a kidney cancer, a leukemia, a lip cancer, a liver cancer, a lymphoma, a melanoma, a mesothelioma, a myeloma, a non-small cell lung cancer, a non-melanoma skin cancer, an oral cancer, an ovarian cancer, a pancreatic cancer, a prostate cancer, a rectal cancer, a sarcoma, a small cell lung cancer, a squamous cell skin cancer, and a thyroid cancer.

In aspects of this embodiment, a cancer includes a bone or muscle cancer including, without limitation, a chondrosarcoma, an Ewing's sarcoma, a malignant fibrous histiocytoma, an osteosarcoma, a rhabdomyosarcoma, and a heart cancer.

In aspects of this embodiment, a cancer includes a brain or neuronal cancer including, without limitation, an astrocytoma, a brainstem glioma, a pilocytic astrocytoma, an ependymoma, a primitive neuroectodermal tumor, a cerebellar astrocytoma, a cerebral astrocytoma, a glioblastoma, a glioma, a medulloblastoma, a neuroblastoma, an oligodendroglioma, a pineal astrocytoma, a pituitary adenoma, and hypothalamic glioma.

In aspects of this embodiment, a cancer includes a breast cancer including, without limitation, a female breast cancer, an invasive cribriform carcinoma, an invasive lobular carcinoma, a medullary carcinoma, a male breast cancer, a phyllodes tumor, and a tubular carcinoma.

In aspects of this embodiment, a cancer includes an endocrine cancer including, without limitation, an adrenocortical carcinoma, an islet cell carcinoma (endocrine pancreas), a merkel cell carcinoma, a multiple endocrine neoplasia syndrome, a parathyroid cancer, a pheochromocytoma, and a thyroid cancer.

In aspects of this embodiment, a cancer includes an eye cancer including, without limitation, a retinoblastoma and an uveal melanoma.

In aspects of this embodiment, a cancer includes a gastrointestinal cancer including, without limitation, an anal cancer, an appendix cancer, a cholangiocarcinoma, a colon cancer, an extrahepatic bile duct cancer, a gallbladder cancer, a gastric (stomach) cancer, a gastrointestinal carcinoid tumor, a gastrointestinal stromal tumor (GIST), a hepatocellular cancer, an islet cell cancer, a pancreatic cancer, and a rectal cancer.

In aspects of this embodiment, a cancer includes a genitourinary or gynecologic cancer including, without limitation, a bladder cancer, a cervical cancer, an endometrial cancer, an extragonadal germ cell tumor, a gestational trophoblastic cancer, an ovarian cancer, an ovarian epithelial cancer (surface epithelial-stromal tumor), an ovarian germ cell cancer, a penile cancer, a renal cell carcinoma, a prostate cancer, a transitional cell cancer (renal pelvis to ureter or ureter and renal pelvis), a testicular cancer, an urethral cancer, an uterine sarcoma, a vaginal cancer, a vulvar cancer, and a Wilms tumor.

In aspects of this embodiment, a cancer includes a head and neck cancer including, without limitation, an esophageal cancer, a head cancer, a hypopharyngeal cancer, a neck cancer, a nasopharyngeal carcinoma, an oral cancer, an oropharyngeal cancer, a paranasal sinus and nasal cavity cancer, a pharyngeal cancer, a salivary gland cancer.

In aspects of this embodiment, a cancer includes a hematopoietic cancer including, without limitation, an acute biphenotypic leukemia, an acute eosinophilic leukemia, an acute lymphoblastic leukemia, an acute myeloid leukemia, an acute myeloid dendritic cell leukemia, an AIDS-related lymphoma, an anaplastic large cell lymphoma, an angioimmunoblastic T-cell lymphoma, a B-cell prolymphocytic leukemia, a Burkitt's lymphoma, a chronic lymphocytic leukemia, a chronic myelogenous leukemia, a cutaneous T-cell lymphoma, a diffuse large B-cell lymphoma, a follicular lymphoma, a hairy cell leukemia, a hepatosplenic T-cell lymphoma, a Hodgkin's lymphoma, an intravascular large B-cell lymphoma, a large granular lymphocytic leukemia, a lymphoplasmacytic lymphoma, a lymphomatoid granulomatosis, a mantle cell lymphoma, a marginal zone B-cell lymphoma, a mast cell leukemia, a mediastinal large B cell lymphoma, a multiple myeloma/plasma cell neoplasm, a myelodysplastic syndrome, a mucosa-associated lymphoid tissue lymphoma, a mycosis fungoides lymphoma, a nodal marginal zone B cell lymphoma, a non-Hodgkin lymphoma, a precursor B lymphoblastic leukemia, a primary central nervous system lymphoma, a primary cutaneous follicular lymphoma, a primary cutaneous immunocytoma, a primary effusion lymphoma, a plasmablastic lymphoma, a Sezary syndrome, a splenic marginal zone lymphoma, and a T-cell prolymphocytic leukemia.

In aspects of this embodiment, a cancer includes a skin cancer including, without limitation, a basal cell carcinoma, a dermatofibrosarcoma protuberans sarcoma, a melanoma, a Merkel cell carcinoma, a sebaceous carcinoma, a skin adnexal tumor, and a squamous cell carcinoma.

In aspects of this embodiment, a cancer includes a thoracic or respiratory cancer including, without limitation, a bronchial adenoma/carcinoid, a laryngeal cancer, a mesothelioma, a non-small cell lung cancer, a pleuropulmonary blastoma, a small cell lung cancer, a thymoma, and a thymic carcinoma.

In aspects of this embodiment, a cancer includes a HIV/AIDS related cancer including, without limitation, a AIDS-related cancer, and a Kaposi sarcoma.

In aspects of this embodiment, a cancer includes an epithelioid hemangioendothelioma (EHE), a desmoplastic small round cell tumor, and a liposarcoma.

Aspects of the present specification can also be described by the following embodiments:

1. A pharmaceutical composition comprising one or more anti-oncogenic phytochemicals produced by a method comprising: a) preparing a macerate comprising a solvent and a plant material from one or more plant species belonging to the family Asteraceae; b) incubating the macerate for a period of time in order to solubilize the one or more anti-oncogenic phytochemicals; and c) purifying the macerate to produce the pharmaceutical composition comprising one or more anti-oncogenic phytochemicals.

2. The pharmaceutical composition of embodiment 1, wherein prior to step (a) the method further comprises a step of processing the plant material from the one or more plant species.

3. The pharmaceutical composition of embodiment 2, wherein prior to step of processing the plant material, the method further comprises a step of collecting one or more plants of the one or more plant species.

4. A pharmaceutical composition comprising one or more anti-oncogenic phytochemicals produced by a method comprising: a) processing a plant material from one or more plant species belonging to the family Asteraceae; b) preparing a macerate comprising a solvent and the plant material; c) incubating the macerate for a period of time in order to solubilize the one or more anti-oncogenic phytochemicals; and d) purifying the macerate to produce the pharmaceutical composition comprising one or more anti-oncogenic phytochemicals.

5. The pharmaceutical composition of embodiment 4, wherein prior to step (a) the method further comprises a step of collecting one or more plants of the one or more plant species.
6. A pharmaceutical composition comprising one or more anti-oncogenic phytochemicals produced by a method comprising: a) collecting one or more plants of one or more plant species belonging to the family Asteraceae; b) processing plant material from the plant species; c) preparing a macerate comprising a solvent and the plant material; d) incubating the macerate for a period of time in order to solubilize the one or more anti-oncogenic phytochemicals; and e) purifying the macerate to produce the pharmaceutical composition comprising one or more anti-oncogenic phytochemicals.
7. The pharmaceutical composition of any one of embodiments 1-6, wherein the one or more plant species belong to the subfamily Asteroideae.
8. The pharmaceutical composition of any one of embodiments 1-7, wherein the one or more plant species belong to the supertribe Asterodae.
9. The pharmaceutical composition of any one of embodiments 1-8, wherein the one or more plant species belong to the tribe Astereae.
10. The pharmaceutical composition of any one of embodiments 1-9, wherein the one or more plant species belong to the genus *Baccharis*.
11. The pharmaceutical composition of any one of embodiments 1-10, wherein the one or more plant species is *Baccharis artemisioides, Baccharis coridifolia*, or *Baccharis dracunculifolia*.
12. The pharmaceutical composition of any one of embodiments 1-11, wherein preparing the macerate comprising adding the plant material to the solvent in a g/L ratio of between 10:100 to 40:100.
13. The pharmaceutical composition of any one of embodiments 1-12, wherein preparing the macerate comprising adding the plant material to the solvent in a g/L ratio of between 15:100 to 35:100.
14. The pharmaceutical composition of any one of embodiments 1-13, wherein preparing the macerate comprising adding the plant material to the solvent in a g/L ratio of between 20:100 to 30:100.
15. The pharmaceutical composition of any one of embodiments 1-14, wherein preparing the macerate comprises heating the solvent to a temperature between 70° C. to 120° C.
16. The pharmaceutical composition of any one of embodiments 1-15, wherein preparing the macerate comprises heating the solvent to a temperature between 80° C. to 110° C.
17. The pharmaceutical composition of any one of embodiments 1-16, wherein preparing the macerate comprises heating the solvent to a temperature between 90° C. to 100° C.
18. The pharmaceutical composition of any one of embodiments 1-17, wherein preparing the macerate comprises processing the plant material into pieces.
19. The pharmaceutical composition of any one of embodiments 1-18, wherein the solvent comprises a pharmaceutically acceptable about 70% to 100% of a monohydric alcohol.
20. The pharmaceutical composition of embodiment 19, wherein the pharmaceutically acceptable monohydric alcohol comprises ethanol, 1-propanol, 2-propanol, isobutanol, tert-amyl alcohol, or any combination thereof.
21. The pharmaceutical composition of any one of embodiments 1-20, wherein the plant material comprises leaves.
22. The pharmaceutical composition of any one of embodiments 1-21, wherein incubation of the macerate is in the dark.
23. The pharmaceutical composition of any one of embodiments 1-22, wherein the period of time for incubating the macerate is 14 days to 42 days.
24. The pharmaceutical composition of any one of embodiments 1-23, wherein the period of time for incubating the macerate is 21 days to 35 days.
25. The pharmaceutical composition of any one of embodiments 1-24, wherein the period of time for incubating the macerate is 26 days to 30 days.
26. The pharmaceutical composition of any one of embodiments 1-25, wherein purifying the macerate comprise one or more filtrations.
27. The pharmaceutical composition of any one of embodiments 1-26, wherein processing the plant material comprises enriching for plant material comprising one or more anti-oncogenic phytochemicals and optionally removing bulk and particulate debris.
28. The pharmaceutical composition of any one of embodiments 1-27, wherein the one or more anti-oncogenic phytochemicals comprise one or more compounds of chemical formula I:

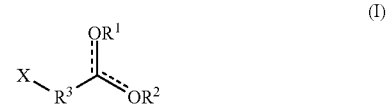

(I)

wherein $R^1$ is independently selected from H, $CH_3$ or $C_2H_5$ or is not present; $R^2$ is independently selected from H, $CH_3$ or $C_2H_5$ or is not present; provided that when $R^1$ is not present, $R^2$ is selected from H, $CH_3$ or $C_2H_5$ and when $R^2$ is not present $R^1$ is selected from H, $CH_3$ or $C_2H_5$; $R^3$ is a $C_{4-40}$ straight or branched chain, alkyl or alkylene and optionally substituted with one or more groups independently selected from $CH_3$, OH, SH, $NH_2$, OMe, OEt, N(H)Me and $NMe_2$; and X is independently selected from $CH_3$, OH, SH, $NH_2$, OMe, OEt, N(H)Me, and $NMe_2$.
29. The pharmaceutical composition of embodiment 28, wherein $R^3$ is a $C_{8-36}$ straight or branched chain, alkyl or alkylene and optionally substituted with one or more groups independently selected from $CH_3$, OH, SH, $NH_2$, OMe, OEt, N(H)Me and $NMe_2$.
30. The pharmaceutical composition of embodiments 28 or 29, wherein $R^3$ is a $C_{10-30}$ straight or branched chain, alkyl or alkylene and optionally substituted with one or more groups independently selected from $CH_3$, OH, SH, $NH_2$, OMe, OEt, N(H)Me and $NMe_2$.
31. The pharmaceutical composition of any one of embodiments 28-30, wherein $R^3$ that is a $C_{12-28}$ straight or branched chain, alkyl or alkylene and optionally substituted with one or more groups independently selected from $CH_3$, OH, SH, $NH_2$, OMe, OEt, N(H)Me and $NMe_2$.
32. The pharmaceutical composition of embodiment 28, wherein $R^3$ is a $C_{4-40}$ straight or branched chain, alkyl or alkylene.

33. The pharmaceutical composition of embodiments 28 or 32, wherein $R^3$ is a $C_{8-36}$ straight or branched chain, alkyl or alkylene.
34. The pharmaceutical composition of any one of embodiments 28, 32 or 33, wherein $R^3$ is a $C_{10-30}$ straight or branched chain, alkyl or alkylene.
35. The pharmaceutical composition of any one of embodiments 28 or 32-34, wherein $R^3$ is a $C_{12-28}$ straight or branched chain, alkyl or alkylene.
36. The pharmaceutical composition of embodiment 28, wherein $R^3$ is a $C_{4-40}$ straight chain alkyl or alkylene and optionally substituted with one or more groups independently selected from $CH_3$, $C_2H_5$, OH, SH, $NH_2$, OMe, OEt, N(H)Me and $NMe_2$.
37. The pharmaceutical composition of embodiments 28 or 36, wherein $R^3$ that is a $C_{8-36}$ straight chain alkyl or alkylene and optionally substituted with one or more groups independently selected from $CH_3$, $C_2H_5$, OH, SH, $NH_2$, OMe, OEt, N(H)Me and $NMe_2$.
38. The pharmaceutical composition of any one of embodiments 28, 36, or 37, wherein provides an $R^3$ is a $C_{10-30}$ straight chain alkyl or alkylene and optionally substituted with one or more groups independently selected from $CH_3$, $C_2H_5$, OH, SH, $NH_2$, OMe, OEt, N(H)Me and $NMe_2$.
39. The pharmaceutical composition any one of embodiments 28 or 36-38, wherein $R^3$ is a $C_{12-28}$ straight chain alkyl or alkylene and optionally substituted with one or more groups independently selected from $CH_3$, $C_2H_5$, OH, SH, $NH_2$, OMe, OEt, N(H)Me and $NMe_2$.
40. The pharmaceutical composition of any one of embodiments 1-28, wherein one or more anti-oncogenic phytochemicals comprise one or more compounds of chemical formula II:

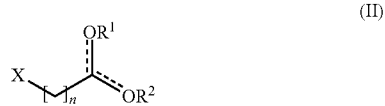

wherein $R^1$ is independently selected from H, $CH_3$ or $C_2H_5$ or is not present; $R^2$ is independently selected from H, $CH_3$ or $C_2H_5$ or is not present; provided that when $R^1$ is not present, $R^2$ is selected from H, $CH_3$ or $C_2H_5$ and when $R^2$ is not present $R^1$ is selected from H, $CH_3$ or $C_2H_5$; n is an integer between 4 and 40; and X is independently selected from $CH_3$, OH, SH, $NH_2$, OMe, OEt, N(H)Me, and $NMe_2$.
41. The pharmaceutical composition of embodiment 40, wherein n is an integer between 8 and 36.
42. The pharmaceutical composition of embodiments 40 or 41, wherein n is an integer between 10 and 30.
43. The pharmaceutical composition of any one of embodiments 40-42, wherein n is an integer between 12 and 28.
44. The pharmaceutical composition of any one of embodiments 1-43, wherein one or more compounds comprise (2E)-21-Hydroxy-2-henicosenoic acid or a derivative thereof, or 21-Hydroxyhenicosanoic acid or a derivative thereof.
45. The pharmaceutical composition of embodiment 44, wherein the one or more compounds comprise (2E)-21-Hydroxy-2-henicosenoic acid or a derivative thereof.
46. The pharmaceutical composition of embodiment 44 or 45, wherein the one or more compounds comprise (2E)-21-Hydroxy-2-henicosenoic acid.
47. The pharmaceutical composition of embodiment 44, wherein the one or more compounds comprise 21-Hydroxyhenicosanoic acid or a derivative thereof.
48. The pharmaceutical composition of embodiment 44 or 47, wherein the one or more compounds comprise 21-Hydroxyhenicosanoic acid.
49. The pharmaceutical composition of any one of embodiments 44-46, wherein the one or more compounds comprise the following compound:

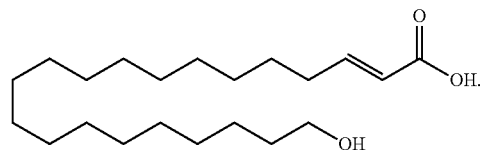 [SMILES: O=C(O)/C=C/CCCCCCCCCCCCCCCCCCO]

50. The pharmaceutical composition of any one of embodiments 44, 47, or 48, wherein the one or more compounds comprise the following compound:

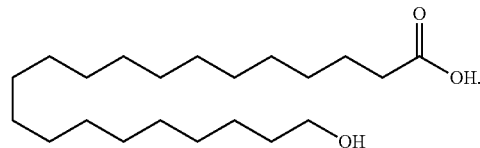 [SMILES: O=C(O)CCCCCCCCCCCCCCCCCCCCO]

51. The pharmaceutical composition of any one of embodiments 1-27, wherein the one or more anti-oncogenic phytochemicals comprise a free $c_{3-40}$ unsaturated fatty acid, a free ω-3 unsaturated fatty acid, a free ω-5 unsaturated fatty acid, a free ω-6 unsaturated fatty acid, a free ω-7 unsaturated fatty acid, a free ω-9 unsaturated fatty acid, a free ω-10 unsaturated fatty acid, a free ω-11 unsaturated fatty acid, a free ω-12 unsaturated fatty acid, or any combination thereof.
52. The pharmaceutical composition of embodiment 51, wherein the free $c_{3-40}$ fatty acid comprises propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid (hexadecenoic acid), margaric acid, stearic acid (octadecenoic acid), nonadecylic acid, arachidic acid (eicosanoic acid), heneicosylic acid, behenic acid (docosanoic acid), tricosylic acid, lignoceric acid (tetracosanic acid), pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontanoic acid, octatriacontanoic acid, nonatriacontanoic acid, and tetracontanoic acid.
53. The pharmaceutical composition of embodiment 51, wherein the free ω-3 unsaturated fatty acid comprises octenoic acid, decenoic acid, decadienoic acid, lauroleic acid, laurolinoleic acid, myristovaccenic acid, myristoinoleic acid, myristolinolenic acid, palmitolinolenic acid, palmitidonic acid, α-linolenic acid, stearidonic acid, dihomo-α-linolenic acid, eicosatraenoic acid, eicosatetraenoic acid, eicosapentaenoic acid, clupanodonic acid (7,10,13,16,19-docosapentaenoic acid), docosahexaenoic acid, 9,12,15,18,21-tetracosapentaenoic acid, and 6,9, 12,15,18,21-tetracosahexaenoic acid.

54. The pharmaceutical composition of embodiment 51, wherein the free ω-5 unsaturated fatty acid comprises myristoleic acid, palmitovaccenic acid, α-eleostearic acid, β-eleostearic acid, punicic acid, 7,10,13-octadecatrienoic acid, 9,12,15-eicosatrienoic acid, and β-eicosatetraenoic acid.

55. The pharmaceutical composition of embodiment 51, wherein the free ω-6 unsaturated fatty acid comprises 8-tetradecenoic acid, 12-octadecenoic acid, linoleic acid, linolelaidic acid, γ-linolenic acid, calendic acid, pinolenic acid, dihomo-linoleic acid, dihomo-γ-linolenic acid, arachidonic acid, adrenic acid, and osbond acid (4,7,10.13.16 docosapentaenoic acid).

56. The pharmaceutical composition of embodiment 51, wherein the free ω-7 unsaturated fatty acid comprises palmitoleic acid, vaccenic acid, rumenic acid, paullinic acid, and 7,10,13-eicosatrienoic acid.

57. The pharmaceutical composition of embodiment 51, wherein the free ω-9 unsaturated fatty acid comprises oleic acid, elaidic acid, gondoic acid (11-eicosenoic acid), erucic acid, nervonic acid, 8,11-eicosadienoic acid, and mead acid (eicosatrienoic acid).

58. The pharmaceutical composition of embodiment 51, wherein the free ω-10 unsaturated fatty acid comprises sapienic acid.

59. The pharmaceutical composition of embodiment 51, wherein the free ω-11 unsaturated fatty acid comprises gadoleic acid.

60. The pharmaceutical composition of embodiment 51, wherein the free ω-12 unsaturated fatty acid comprises 4-hexadecenoic acid, petroselinic acid, and 8-eicosenoic acid.

61. The pharmaceutical composition of any one of embodiments 1-26, wherein the one or more anti-oncogenic phytochemicals comprise one or more trichothecenes.

62. The pharmaceutical composition of embodiment 61, wherein the one or more trichothecenes comprise one or more Type A trichothecenes, one or more Type B trichothecenes, one or more Type C trichothecenes, one or more Type D trichothecenes, or any combination thereof.

63. The pharmaceutical composition of embodiment 61, wherein the one or more trichothecenes comprise Isosatratoxin F, Roridin A, Roridin E, Roridin H, Roridin L-2, Satratoxin G, Satratoxin H, Verrucarin A, Verrucarin J, or any combination thereof.

64. A method of preparing a pharmaceutical composition comprising one or more anti-oncogenic phytochemicals, the method comprising: a) preparing a macerate comprising a solvent and a plant material from one or more plant species belonging to the family Asteraceae; b) incubating the macerate for a period of time in order to solubilize the one or more anti-oncogenic phytochemicals; and c) purifying the macerate to produce the pharmaceutical composition comprising one or more anti-oncogenic phytochemicals.

65. The method of embodiment 64, wherein prior to step (a) the method further comprises a step of processing the plant material from the one or more plant species.

66. The method of embodiment 65, wherein prior to step of processing the plant material, the method further comprises a step of collecting one or more plants of the one or more plant species.

67. A method of preparing a pharmaceutical composition comprising one or more anti-oncogenic phytochemicals, the method comprising: a) processing a plant material from one or more plant species belonging to the family Asteraceae; b) preparing a macerate comprising a solvent and the plant material; c) incubating the macerate for a period of time in order to solubilize the one or more anti-oncogenic phytochemicals; and d) purifying the macerate to produce the pharmaceutical composition comprising one or more anti-oncogenic phytochemicals.

68. The method of embodiment 67, wherein prior to step (a) the method further comprises a step of collecting one or more plants of the one or more plant species.

69. A method of preparing a pharmaceutical composition comprising one or more anti-oncogenic phytochemicals, the method comprising: a) collecting one or more plants of one or more plant species belonging to the family Asteraceae; b) processing plant material from the plant species; c) preparing a macerate comprising a solvent and the plant material; d) incubating the macerate for a period of time in order to solubilize the one or more anti-oncogenic phytochemicals; and e) purifying the macerate to produce the pharmaceutical composition comprising one or more anti-oncogenic phytochemicals.

70. The method of any one of embodiments 64-69, wherein the one or more plant species belong to the subfamily Asteroideae.

71. The method of any one of embodiments 64-70, wherein the one or more plant species belong to the supertribe Asterodae.

72. The method of any one of embodiments 64-71, wherein the one or more plant species belong to the tribe Astereae.

73. The method of any one of embodiments 64-72, wherein the one or more plant species belong to the genus *Baccharis*.

74. The method of any one of embodiments 64-73, wherein the one or more plant species is *Baccharis artemisioides, Baccharis coridifolia*, or *Baccharis dracunculifolia*.

75. The method of any one of embodiments 64-74, wherein preparing the macerate comprising adding the plant material to the solvent in a g/L ratio of between 10:100 to 40:100.

76. The method of any one of embodiments 64-75, wherein preparing the macerate comprising adding the plant material to the solvent in a g/L ratio of between 15:100 to 35:100.

77. The method of any one of embodiments 64-76, wherein preparing the macerate comprising adding the plant material to the solvent in a g/L ratio of between 20:100 to 30:100.

78. The method of any one of embodiments 64-77, wherein preparing the macerate comprises heating the solvent to a temperature between 70° C. to 120° C.

79. The method of any one of embodiments 64-78, wherein preparing the macerate comprises heating the solvent to a temperature between 80° C. to 110° C.

80. The method of any one of embodiments 64-79, wherein preparing the macerate comprises heating the solvent to a temperature between 90° C. to 100° C.

81. The method of any one of embodiments 64-80, wherein preparing the macerate comprises cutting the plant material into pieces.

82. The method of any one of embodiments 64-81, wherein the solvent comprises about 70% to 100% of a pharmaceutically acceptable monohydric alcohol.
83. The method of embodiment 82, wherein the pharmaceutically acceptable monohydric alcohol comprises ethanol, 1-propanol, 2-propanol, isobutanol, tert-amyl alcohol, or any combination thereof.
84. The method of any one of embodiments 64-83, wherein the plant material comprises leaves.
85. The method of any one of embodiments 64-84, wherein incubation of the macerate is in the dark.
86. The method of any one of embodiments 64-85, wherein the period of time for incubating the macerate is 14 days to 42 days.
87. The method of any one of embodiments 64-86, wherein the period of time for incubating the macerate is 21 days to 35 days.
88. The method of any one of embodiments 64-87, wherein the period of time for incubating the macerate is 26 days to 30 days.
89. The method of any one of embodiments 64-88, wherein purifying the macerate comprise one or more filtrations.
90. The method of any one of embodiments 64-89, wherein processing the plant material comprises enriching for plant material comprising one or more anti-oncogenic phytochemicals and optionally removing bulk and particulate debris.
91. The method of any one of embodiments 64-90, wherein the one or more anti-oncogenic phytochemicals comprise one or more compounds of any one of embodiments 28-60.
92. The method of any one of embodiments 64-90, wherein the one or more anti-oncogenic phytochemicals comprise one or more trichothecenes.
93. The method of embodiment 92, wherein the one or more trichothecenes comprise one or more Type A trichothecenes, one or more Type B trichothecenes, one or more Type C trichothecenes, one or more Type D trichothecenes, or any combination thereof.
94. The method of embodiment 92, wherein the one or more trichothecenes comprise Isosatratoxin F, Roridin A, Roridin E, Roridin H, Roridin L-2, Satratoxin G, Satratoxin H, Verrucarin A, Verrucarin J, or any combination thereof.
95. A pharmaceutical composition comprising one or more anti-oncogenic phytochemicals produced by a method according to any one of embodiment 64-94.
96. A medicament comprising one or more anti-oncogenic phytochemicals produced by a method according to any one of embodiment 64-94.
97. A pharmaceutical composition comprising one or more anti-oncogenic phytochemicals.
98. The pharmaceutical composition of embodiment 97, wherein the one or more anti-oncogenic phytochemicals comprise one or more compounds of any one of embodiments 28-60.
99. The pharmaceutical composition of embodiment 97, wherein the one or more anti-oncogenic phytochemicals comprise one or more trichothecenes.
100. The pharmaceutical composition of embodiment 99, wherein the one or more trichothecenes comprise one or more Type A trichothecenes, one or more Type B trichothecenes, one or more Type C trichothecenes, one or more Type D trichothecenes, or any combination thereof.
101. The pharmaceutical composition of embodiment 99, wherein the one or more trichothecenes comprise Isosatratoxin F, Roridin A, Roridin E, Roridin H, Roridin L-2, Satratoxin G, Satratoxin H, Verrucarin A, Verrucarin J, or any combination thereof.
102. A medicament comprising one or more anti-oncogenic phytochemicals.
103. The medicament of embodiment 102, wherein the one or more anti-oncogenic phytochemicals comprise one or more compounds of any one of embodiments 28-60.
104. The medicament of embodiment 102, wherein the one or more anti-oncogenic phytochemicals comprise one or more trichothecenes.
105. The medicament of embodiment 104, wherein the one or more trichothecenes comprise one or more Type A trichothecenes, one or more Type B trichothecenes, one or more Type C trichothecenes, one or more Type D trichothecenes, or any combination thereof.
106. The medicament of embodiment 104, wherein the one or more trichothecenes comprise Isosatratoxin F, Roridin A, Roridin E, Roridin H, Roridin L-2, Satratoxin G, Satratoxin H, Verrucarin A, Verrucarin J, or any combination thereof.
107. Use of a pharmaceutical composition comprising one or more anti-oncogenic phytochemicals as defined in any one of embodiments 1-63, 95, or 97-101 in the manufacture of a medicament for the treatment of a cancer.
108. A method of treating a cancer in an individual, the method comprising administering a pharmaceutical composition comprising one or more anti-oncogenic phytochemicals as defined in any one of embodiments 1-63, 95, or 97-101 or a medicament as defined in any one of embodiments 96 or 102-106 to the individual.
109. A pharmaceutical composition comprising one or more anti-oncogenic phytochemicals as defined in any one of embodiments 1-63, 95 or 97-101 for the treatment of a cancer or a medicament as defined in any one of embodiments 96 or 102-106 for use in the treatment of a cancer.
110. Use of a pharmaceutical composition comprising one or more anti-oncogenic phytochemicals as defined in any one of embodiments 1-63, 95 or 97-101 or a medicament as defined in any one of embodiments 96 or 102-106 in the treatment of a cancer.
111. The method of embodiment 108, the pharmaceutical composition of embodiment 109, or the use of embodiment 110, wherein the cancer is a solid malignant neoplasm or a non-solid malignant neoplasm.
112. The method of embodiment 108, the pharmaceutical composition of embodiment 109, or the use of embodiment 110, wherein the cancer is a carcinoma, a sarcoma, a lymphoma, a leukemia or a blastoma.
113. The method of embodiment 108, the pharmaceutical composition of embodiment 109, or the use of embodiment 110, wherein the cancer is a primary cancer or a metastatic cancer of a bone tissue, a breast tissue, a brain tissue, a blood tissue, an endocrine tissue, an eye tissue, a gastrointestinal tissue, a genitourinary tissue, a gynecological tissue, a hematopoietic tissue, a muscle tissue, a neuronal tissue, a skin tissue, a thoracic tissue.
114. The method of embodiment 108, the pharmaceutical composition of embodiment 109, or the use of embodiment 110, wherein the cancer is a bile duct cancer, a bladder cancer, a bone cancer, a breast cancer, a brain cancer, a colon cancer, an eye cancer, an esophageal cancer, a gastric cancer, a kidney cancer, a leukemia, a liver cancer, a lung cancer, a lymphoma, a muscle cancer, a neuronal cancer, an oral cancer, an ovarian cancer, a pancreatic cancer, a rectal cancer, a skin cancer, a small intestine cancer, a testicular cancer, a thyroid cancer, a uterine cancer, a vaginal cancer.

115. The pharmaceutical compositions as defined in any one of embodiments 1-63, 95, 97-101, or 109-114, the method as defined in any one of embodiments 64-94, the medicament as defined in any one of embodiments 96 or 102-106, the use as defined in any one of embodiments 107 or 110-114 and the method as defined in any one of embodiments 108 or 110-114, wherein the one or more anti-oncogenic phytochemicals are in an amount of about 0.05%, about 0.1%, about 1%, about 2.5%, about 5%, about 7.5%, about 10%, about 12.5%, about 15%, about 17.5%, about 20%, about 22.5%, about 25%, about 30%, about 35%, about 40%, about 45%, or about 50% by weight or wherein the one or more anti-oncogenic phytochemicals are in an amount of at least 0.05%, at least 0.1%, at least 1%, at least 2.5%, at least 5%, at least 7.5%, at least 10%, at least 12.5%, at least 15%, at least 17.5%, at least 20%, at least 22.5%, at least 25%, at least 30%, at least 35%, at least 40%, at least 45%, or at least 50% by weight and/or wherein the one or more anti-oncogenic phytochemicals are in an amount of at most 0.05%, at most 0.1%, at most 1%, at most 2.5%, at most 5%, at most 7.5%, at most 10%, at most 12.5%, at most 15%, at most 17.5%, at most 20%, at most 22.5%, at most 25%, at most 30%, at most 35%, at most 40%, at most 45%, or at most 50% by weight or wherein the one or more anti-oncogenic phytochemicals are in an amount of about 0.05% to about 1%, about 0.05% to about 2.5%, about 0.05% to about 5%, about 0.05% to about 7.5%, about 0.05% to about 10%, about 0.05% to about 12.5%, about 0.05% to about 15%, about 0.05% to about 17.5%, about 0.05% to about 20%, about 0.05% to about 22.5%, about 0.05% to about 25%, about 0.05% to about 30%, about 0.05% to about 40%, about 0.05% to about 50%, about 0.1% to about 1%, about 0.1% to about 2.5%, about 0.1% to about 5%, about 0.1% to about 7.5%, about 0.1% to about 10%, about 0.1% to about 12.5%, about 0.1% to about 15%, about 0.1% to about 17.5%, about 0.1% to about 20%, about 0.1% to about 22.5%, about 0.1% to about 25%, about 0.1% to about 30%, about 0.1% to about 40%, about 0.1% to about 50%, about 1% to about 2.5%, about 1% to about 5%, about 1% to about 7.5%, about 1% to about 10%, about 1% to about 12.5%, about 1% to about 15%, about 1% to about 17.5%, about 1% to about 20%, about 1% to about 22.5%, about 1% to about 25%, about 1% to about 30%, about 1% to about 40%, about 1% to about 50%, about 5% to about 10%, about 5% to about 20%, about 5% to about 30%, about 5% to about 40%, about 5% to about 50%, about 10% to about 20%, about 10% to about 30%, about 10% to about 40%, about 10% to about 50%, about 20% to about 30%, about 20% to about 40%, about 20% to about 50%, about 30% to about 40%, about 30% to about 50%, or about 40% to about 50% by weight.

116. The pharmaceutical compositions as defined in any one of embodiments 1-63, 95, 97-101, or 109-114, the method as defined in any one of embodiments 64-94, the medicament as defined in any one of embodiments 96 or 102-106, the use as defined in any one of embodiments 107 or 110-114 and the method as defined in any one of embodiments 108 or 110-114, wherein the one or more anti-oncogenic phytochemicals are in an amount of about 0.01 mg/mL, about 0.025 mg/mL, about 0.05 mg/mL, about 0.075 mg/mL, about 0.1 mg/mL, about 0.15 mg/mL, about 0.2 mg/mL, about 0.25 mg/mL, about 0.3 mg/mL, about 0.35 mg/mL, about 0.4 mg/mL, about 0.45 mg/mL, about 0.5 mg/mL, about 0.55 mg/mL, about 0.6 mg/mL, about 0.65 mg/mL, about 0.7 mg/mL, about 0.75 mg/mL, about 0.8 mg/mL, about 0.85 mg/mL, about 0.9 mg/mL, about 0.95 mg/mL, about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 60 mg/mL, about 65 mg/mL, about 70 mg/mL, about 75 mg/mL, about 100 mg/mL, about 125 mg/mL, about 150 mg/mL, about 175 mg/mL, about 200 mg/mL, about 225 mg/mL, about 250 mg/mL, about 275 mg/mL, about 300 mg/mL, about 325 mg/mL, about 350 mg/mL, about 375 mg/mL, about 400 mg/mL, about 425 mg/mL, about 450 mg/mL, about 475 mg/mL, or about 500 mg/mL or wherein the one or more anti-oncogenic phytochemicals in a concentration of at least 0.01 mg/mL, at least 0.025 mg/mL, at least 0.05 mg/mL, at least 0.075 mg/mL, at least 0.1 mg/mL, at least 0.15 mg/mL, at least 0.2 mg/mL, at least 0.25 mg/mL, at least 0.3 mg/mL, at least 0.35 mg/mL, at least 0.4 mg/mL, at least 0.45 mg/mL, at least 0.5 mg/mL, at least 0.55 mg/mL, at least 0.6 mg/mL, at least 0.65 mg/mL, at least 0.7 mg/mL, at least 0.75 mg/mL, at least 0.8 mg/mL, at least 0.85 mg/mL, at least 0.9 mg/mL, at least 0.95 mg/mL, at least 1 mg/mL, at least 5 mg/mL, at least 10 mg/mL, at least 15 mg/mL, at least 20 mg/mL, at least 25 mg/mL, at least 30 mg/mL, at least 35 mg/mL, at least 40 mg/mL, at least 45 mg/mL, at least 50 mg/mL, at least 60 mg/mL, at least 65 mg/mL, at least 70 mg/mL, at least 75 mg/mL, at least 100 mg/mL, at least 125 mg/mL, at least 150 mg/mL, at least 175 mg/mL, at least 200 mg/mL, at least 225 mg/mL, at least 250 mg/mL, at least 275 mg/mL, at least 300 mg/mL, at least 325 mg/mL, at least 350 mg/mL, at least 375 mg/mL, at least 400 mg/mL, at least 425 mg/mL, at least 450 mg/mL, at least 475 mg/mL, or at least 500 mg/mL and/or wherein the one or more anti-oncogenic phytochemicals are in a concentration of at most 0.01 mg/mL, at most 0.025 mg/mL, at most 0.05 mg/mL, at most 0.075 mg/mL, at most 0.1 mg/mL, at most 0.15 mg/mL, at most 0.2 mg/mL, at most 0.25 mg/mL, at most 0.3 mg/mL, at most 0.35 mg/mL, at most 0.4 mg/mL, at most 0.45 mg/mL, at most 0.5 mg/mL, at most 0.55 mg/mL, at most 0.6 mg/mL, at most 0.65 mg/mL, at most 0.7 mg/mL, at most 0.75 mg/mL, at most 0.8 mg/mL, at most 0.85 mg/mL, at most 0.9 mg/mL, at most 0.95 mg/mL, at most 1 mg/mL, at most 5 mg/mL, at most 10 mg/mL, at most 15 mg/mL, at most 20 mg/mL, at most 25 mg/mL, at most 30 mg/mL, at most 35 mg/mL, at most 40 mg/mL, at most 45 mg/mL, at most 50 mg/mL, at most 60 mg/mL, at most 65 mg/mL, at most 70 mg/mL, at most 75 mg/mL, at most 100 mg/mL, at most 125 mg/mL, at most 150 mg/mL, at most 175 mg/mL, at most 200 mg/mL, at most 225 mg/mL, at most 250 mg/mL, at most 275 mg/mL, at most 300 mg/mL, at most 325 mg/mL, at most 350 mg/mL, at most 375 mg/mL, at most 400 mg/mL, at most 425 mg/mL, at most 450 mg/mL, at most 475 mg/mL, or at most 500 mg/mL, or wherein the one or more anti-oncogenic phytochemicals are in an amount of about 0.01 mg/mL to about 0.05 mg/mL, about 0.01 mg/mL to about 0.1 mg/mL, about 0.01 mg/mL to about 0.5 mg/mL, about 0.01 mg/mL to about 1 mg/mL, about 0.01 mg/mL to about 5 mg/mL, about 0.01 mg/mL to about 10 mg/mL, about 0.01 mg/mL to about 20 mg/mL, about 0.01 mg/mL to about 25 mg/mL, about 0.01 mg/mL to about 50 mg/mL, about 0.01 mg/mL to about 75 mg/mL, about 0.01 mg/mL to about 100 mg/mL, about 0.01 mg/mL to about 125 mg/mL, about 0.01 mg/mL to about 150 mg/mL, about 0.01 mg/mL to about 200 mg/mL, about 0.05 mg/mL to about 0.1 mg/mL, about 0.05 mg/mL to about 0.5 mg/mL, about 0.05 mg/mL to about 1 mg/mL, about 0.05 mg/mL to about 5 mg/mL, about 0.05 mg/mL to about 10 mg/mL, about 0.05 mg/mL to about 20 mg/mL, about 0.05 mg/mL to about 25 mg/mL, about 0.05 mg/mL to about 50 mg/mL, about 0.05 mg/mL to about 75 mg/mL, about 0.05 mg/mL to about 100 mg/mL, about 0.05 mg/mL to about 125 mg/mL, about 0.05 mg/mL to about 150 mg/mL, about 0.05 mg/mL to about 200 mg/mL, about 0.1 mg/mL to about 0.5 mg/mL, about 0.1 mg/mL to about 1 mg/mL, about 0.1 mg/mL to about 5 mg/mL, about 0.1 mg/mL to about 10 mg/mL, about 0.1 mg/mL to about 20 mg/mL, about 0.1 mg/mL to about 25 mg/mL, about 0.1 mg/mL to about 50 mg/mL, about 0.1 mg/mL to about 75 mg/mL, about 0.1 mg/mL to about 100 mg/mL, about 0.1 mg/mL to about 125 mg/mL, about 0.1 mg/mL to about 150 mg/mL, about 0.1 mg/mL to about 200 mg/mL, about 0.5 mg/mL to about 1 mg/mL, about 0.5 mg/mL to about 5 mg/mL, about 0.5 mg/mL to about 10 mg/mL, about 0.5 mg/mL to about 20 mg/mL, about 0.5 mg/mL to about 25 mg/mL, about 0.5 mg/mL to about 50 mg/mL, about 0.5 mg/mL to about 75 mg/mL, about 0.5 mg/mL to about 100 mg/mL, about 0.5 mg/mL to about 125 mg/mL, about 0.5 mg/mL to about 150 mg/mL, about 0.5 mg/mL to about 200 mg/mL, about 1 mg/mL to about 5 mg/mL, about 1 mg/mL to about 10 mg/mL, about 1 mg/mL to about 20 mg/mL, about 1 mg/mL to about 25 mg/mL, about 1 mg/mL to about 50 mg/mL, about 1 mg/mL to about 75 mg/mL, about 1 mg/mL to about 100 mg/mL, about 1 mg/mL to about 125 mg/mL, about 1 mg/mL to about 150 mg/mL, about 1 mg/mL to about 200 mg/mL, about 5 mg/mL to about 10 mg/mL, about 5 mg/mL to about 20 mg/mL, about 5 mg/mL to about 25 mg/mL, about 5 mg/mL to about 50 mg/mL, about 5 mg/mL to about 75 mg/mL, about 5 mg/mL to about 100 mg/mL, about 5 mg/mL to about 125 mg/mL, about 5 mg/mL to about 150 mg/mL, about 5 mg/mL to about 200 mg/mL, about 10 mg/mL to about 20 mg/mL, about 10 mg/mL to about 25 mg/mL, about 10 mg/mL to about 50 mg/mL, about 10 mg/mL to about 75 mg/mL, about 10 mg/mL to about 100 mg/mL, about 10 mg/mL to about 125 mg/mL, about 10 mg/mL to about 150 mg/mL, about 10 mg/mL to about 200 mg/mL, about 25 mg/mL to about 50 mg/mL, about 25 mg/mL to about 75 mg/mL, about 25 mg/mL to about 100 mg/mL, about 25 mg/mL to about 125 mg/mL, about 25 mg/mL to about 150 mg/mL, about 25 mg/mL to about 200 mg/mL, about 50 mg/mL to about 100 mg/mL, about 50 mg/mL to about 150 mg/mL, about 50 mg/mL to about 200 mg/mL, about 75 mg/mL to about 150 mg/mL, about 75 mg/mL to about 200 mg/mL, about 100 mg/mL to about 150 mg/mL, about 100 mg/mL to about 200 mg/mL, about 125 mg/mL to about 150 mg/mL, about 125 mg/mL to about 200 mg/mL, about 150 mg/mL to about 200 mg/mL, or wherein the one or more anti-oncogenic phytochemicals are in an amount of about 5 mg/mL to about 20 mg/mL, about 5 mg/mL to about 25 mg/mL, about 5 mg/mL to about 50 mg/mL, about 5 mg/mL to about 75 mg/mL, about 5 mg/mL to about 100 mg/mL, about 5 mg/mL to about 125 mg/mL, about 5 mg/mL to about 150 mg/mL, about 5 mg/mL to about 175 mg/mL, about 5 mg/mL to about 200 mg/mL, about 5 mg/mL to about 225 mg/mL, about 5 mg/mL to about 250 mg/mL, about 5 mg/mL to about 275 mg/mL, about 5 mg/mL to about 300 mg/mL, about 5 mg/mL to about 325 mg/mL, about 5 mg/mL to about 350 mg/mL, about 5 mg/mL to about 375 mg/mL, about 5 mg/mL to about 400 mg/mL, about 5 mg/mL to about 425 mg/mL, about 5 mg/mL to about 450 mg/mL, about 5 mg/mL to about 475 mg/mL, about 5 mg/mL to about 500 mg/mL, about 10 mg/mL to about 20 mg/mL, about 10 mg/mL to about 25 mg/mL, about 10 mg/mL to about 50 mg/mL, about 10 mg/mL to about 75 mg/mL, about 10 mg/mL to about 100 mg/mL, about 10 mg/mL to about 125 mg/mL, about 10 mg/mL to about 150 mg/mL, about 10 mg/mL to about 175 mg/mL, about 10 mg/mL to about 200 mg/mL, about 10 mg/mL to about 225 mg/mL, about 10 mg/mL to about 250 mg/mL, about 10 mg/mL to about 275 mg/mL, about 10 mg/mL to about 300 mg/mL, about 10 mg/mL to about 325 mg/mL, about 10 mg/mL to about 350 mg/mL, about 10 mg/mL to about 375 mg/mL, about 10 mg/mL to about 400 mg/mL, about 10 mg/mL to about 425 mg/mL, about 10 mg/mL to about 450 mg/mL, about 10 mg/mL to about 475 mg/mL, about 10 mg/mL to about 500 mg/mL, about 25 mg/mL to about 50 mg/mL, about 25 mg/mL to about 75 mg/mL, about 25 mg/mL to about 100 mg/mL, about 25 mg/mL to about 125 mg/mL, about 25 mg/mL to about 150 mg/mL, about 25 mg/mL to about 175 mg/mL, about 25 mg/mL to about 200 mg/mL, about 25 mg/mL to about 225 mg/mL, about 25 mg/mL to about 250 mg/mL, about 25 mg/mL to about 275 mg/mL, about 25 mg/mL to about 300 mg/mL, about 25 mg/mL to about 325 mg/mL, about 25 mg/mL to about 350 mg/mL, about 25 mg/mL to about 375 mg/mL, about 25 mg/mL to about 400 mg/mL, about 25 mg/mL to about 425 mg/mL, about 25 mg/mL to about 450 mg/mL, about 25 mg/mL to about 475 mg/mL, about 25 mg/mL to about 500 mg/mL, about 50 mg/mL to about 75 mg/mL, about 50 mg/mL to about 100 mg/mL, about 50 mg/mL to about 125 mg/mL, about 50 mg/mL to about 150 mg/mL, about 50 mg/mL to about 175 mg/mL, about 50 mg/mL to about 200 mg/mL, about 50 mg/mL to about 225 mg/mL, about 50 mg/mL to about 250 mg/mL, about 50 mg/mL to about 275 mg/mL, about 50 mg/mL to about 300 mg/mL, about 50 mg/mL to about 325 mg/mL, about 50 mg/mL to about 350 mg/mL, about 50 mg/mL to about 375 mg/mL, about 50 mg/mL to about 400 mg/mL, about 50 mg/mL to about 425 mg/mL, about 50 mg/mL to about 450 mg/mL, about 50 mg/mL to about 475 mg/mL, about 50 mg/mL to about 500 mg/mL, about 75 mg/mL to about 100 mg/mL, about 75 mg/mL to about 125 mg/mL, about 75 mg/mL to about 150 mg/mL, about 75 mg/mL to about 175 mg/mL, about 75 mg/mL to about 200 mg/mL, about 75 mg/mL to about 225 mg/mL, about 75 mg/mL to about 250 mg/mL, about 75 mg/mL to about 275 mg/mL, about 75 mg/mL to about 300 mg/mL, about 75 mg/mL to about 325 mg/mL, about 75 mg/mL to about 350 mg/mL, about 75 mg/mL to about 375 mg/mL, about 75 mg/mL to about 400 mg/mL, about 75 mg/mL to about 425 mg/mL, about 75 mg/mL to about 450 mg/mL, about 75 mg/mL to about 475 mg/mL, about 75 mg/mL to about 500 mg/mL, about 100 mg/mL to about 125 mg/mL, about 100 mg/mL to about 150 mg/mL, about 100 mg/mL to about 175 mg/mL, about 100 mg/mL to about 200 mg/mL, about 100 mg/mL to about 225 mg/mL, about 100 mg/mL to about 250 mg/mL, about 100 mg/mL to about 275 mg/mL, about 100 mg/mL to about 300 mg/mL, about 100 mg/mL to about 325 mg/mL, about 100 mg/mL to about 350 mg/mL, about 100 mg/mL to about 375 mg/mL, about 100 mg/mL to about 400 mg/mL, about 100 mg/mL to about 425 mg/mL, about 100 mg/mL to about 450 mg/mL, about 100 mg/mL to about 475 mg/mL, or about 100 mg/mL to about 500 mg/mL.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

Example 1

Preparation of OST-01

The following example illustrates a method of preparation for OST-01.

To prepare OST-01, plants from the species *Baccharis coridifolia* were harvested and the aerial leaves were removed. The harvested leaves were washed in distilled water, dried with paper towels, cut into small pieces using a ceramic knife, and weighted. The processed plant material was macerated by placing 250 g of plant material inside a wide-mouthed glass container and adding one L of 90% ethanol heated to 96° C. The container was then sealed using a screwcap lid and stored in the dark at 15° C. to 20° C. for 28 days or until the soluble matter is dissolved. After maceration, the contents were pressed using a small wine press and the marc was discarded. The pressed extract was then filtered and the resulting clarified eluent was aliquoted into brown glass bottles and stored in the dark at 15° C. to 20° C. This eluent was considered an extract comprising one or more one or more anti-oncogenic phytochemicals and was designated OST-01.

Example 2

OST-01 Suppresses Cellular Proliferation in Leukemic Cells

To investigate the effects of OST-01 on cell proliferation in leukemic cells, MTS proliferation assays and immunoblotting analyses using a biomarker for cell proliferation were conducted to determine whether OST-01 activity could suppress proliferation of leukemia cells.

Three different acute myeloid leukemia (AML) cell lines were selected for these studies: a MV-4-11 cell line (RRID: CVCL_0064), a KG-1a cell line (RRID:CVCL_1824), and a Kasumi-1 cell line (RRID:CVCL_0589). All three cell lines were obtained from the American Type Culture Collection (ATCC). MV-4-11 cells are macrophages exhibiting a lymphoblast morphology that were isolated from the blast cells of a 10-year-old human child subject diagnosed with biphenotypic B-myelomonocytic leukemia (an acute monoblastic/monocytic leukemia). KG-1a cells are a mixture of promyeloblast and macrophages exhibiting a rounded morphology that were isolated from a 59-year-old human adult subject diagnosed with acute myeloid leukemia. Kasumi-1 cells are myeloblast exhibiting a myeloblast morphology that were isolated from the blast cells of a human infant subject diagnosed with acute myeloblastic leukemia. Cell lines were authenticated by cell morphology monitoring, growth curve analysis, and *Mycoplasma* detection using a *Mycoplasma* Detection Kit (Roche, Germany). Cell lines were maintained in Iscove's Modified Dulbecco's Medium (IMDM) or Roswell Park Memorial Institute (RPMI) medium supplemented with 10% Fetal bovine serum (FBS) and 100 units of penicillin/streptomycin an incubated at 37° C. in 5% $CO_2$ incubator.

A MST assay is a colorimetric assay determining the number of viable cells in a proliferation or cytotoxicity assay. This assay employs tetrazolium compound (3-(4,5-dimethylthiazol-2-yl)-5-(3-carboxymethoxyphenyl)-2-(4-sulfophenyl)-2H-tetrazolium), designated MTS, in the presence of an electron coupling reagent, like phenazine methosulfate (PMS) or phenazine ethosulfate (PES). The MTS is bioreduced by cells into a colored formazan product that is soluble in tissue culture medium and has an absorbance maximum at 490 nm. This MTS to formazan conversion is accomplished by NADPH or NADH produced by dehydrogenase enzymes present in metabolically active cells. Thus, the quantity of formazan measured by absorbance at 490 nm is directly proportional to the metabolic activity of the cells and serves as a proxy for the number of living cells present in a culture, and indicator cellular viability including cellular growth and proliferation.

In one series of experiments, MV-4-11, KG-1a, and Kasumi-1 cells were grown to an appropriate density and approximately 20,000 cells/100 µL were seeded into wells of 96-well cell culture microplate. Either 1 µL/mL of OST-01 or 1 µL/mL control vehicle was then added to transferred cells for each of the three AML cell lines and incubated for 24 hours at 37° C. in 5% $CO_2$ incubator. Cell growth was then assessed using a MTS proliferation assay (CellTiter 96 AQueous One assay, Promega) following protocols provided by the manufacture. To determine the amount of soluble formazan produced by cellular reduction of MTS, the absorbance of each well is measured at 490 nm using a 96-well plate reader. Mean absorbance between the OST-01 treated and control group was statistically analyzed by using unpaired, two-tailed Student's t test, with values from at least two independent experiments with triplicate determination. Data are presented as mean±standard error (SE) and a $p<0.05$ was considered statistically significant.

Figure 1B:
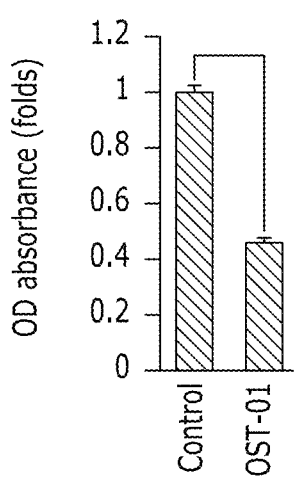
Figure 1C:
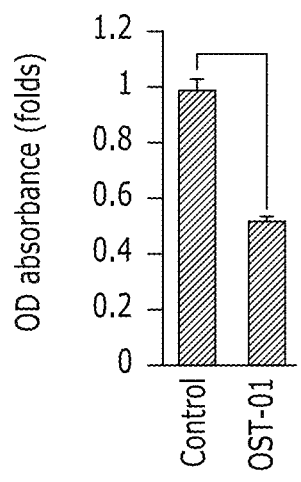

As shown in FIGS. 1A-1C, results from the MTS proliferation assay demonstrated that treatment with OST-01 exhibited a statistically significant decrease in OD absorbance at 490 nm as compared to the control in all AML cell lines tested. For example, MV-4-11 cells treated with OST-01 showed more than 20% decrease in OD absorbance relative to cells treated with the vehicle control (see FIG. 1A, $p<0.001$), KG-1a cells treated with OST-01 showed at an almost 60% decrease in OD absorbance relative to cells treated with the vehicle control (see FIG. 1B, p<0.001), and Kasumi-1 cells treated with OST-01 showed at least a 50% decrease in OD absorbance relative to cells treated with the vehicle control (see FIG. 1C, p<0.001). Taken together, the results from the MTS proliferation assay demonstrated that treatment with OST-01 significantly reduces cellular proliferation in three different AML cell lines, demonstrating the anti-oncogenic activity of OST-01 in non-solid cancer cells.

A WST-1 cell proliferation assay is a colorimetric assay which determines the number of viable cells in a proliferation or cytotoxicity assay. This assay employs tetrazolium compound (4-[3-(4-iodophenyl)-2-(4-nitrophenyl)-2H-5-tetrazolio]-1,3-benzene disulfonate), designated WST-1, which is bioreduced in the presence of NAD(P)H or NADH produced by dehydrogenase enzymes used in glycolysis by metabolically active cells. The bioreduction of WST-1 produces a dark red formazan dye that is soluble and has an absorbance maximum at 450 nm. Thus, the quantity of formazan dye measured by absorbance at 450 nm is directly proportional to the metabolic activity of the cells and serves as a proxy for the number of living cells present in a culture, and indicator cellular viability including cellular growth and proliferation.

In one series of experiments, cells from a MV-4-11 AML cancer cell line, a KG-1a AML cancer cell line, or a Kasumi-1 AML cancer cell line were grown to an appropriate density and approximately $1\times10^4$ cells were seeded into wells of 96-well cell culture microplate and incubated for 24 hours at 37° C. in the humidified incubator with 5% $CO_2$. After incubation, growth medium was removed from each well 96 and replaced with fresh growth medium containing a specified concentration of OST-01 or an ethanol control. The treated cells were then incubated for another 24 hours at 37° C. in 5% $CO_2$ incubator. Cell growth was then assessed using a Cell Proliferation Reagent WST-1 (Roche Diagnostics, Germany) following protocols provided by the manufacture. To determine the amount of soluble formazan produced by cellular reduction of WETS-1, the absorbance of each well is measured at 450 nm using a multimode microplate reader (Molecular Devices, USA). Cell proliferation of the ethanol control was taken as 100% and that of OST-01 treated groups were calculated as percentage of ethanol control.

As shown in Table 1, results from the WST-1 proliferation assay demonstrated that treatment with OST-01 exhibited a statistically significant decrease in cell proliferation as compared to the ethanol control in all AML cancer cell lines tested. For example, MV-4-11 cells treated with OST-01 exhibited at least a 98% inhibition of cell proliferation at a concentration of 1.0 µL/mL. Similarly, KG-1A cells treated with OST-01 exhibited at least a 99% inhibition of cell proliferation at a concentration of 1.0 µL/mL. Likewise, Kasumi-1 cells treated with OST-01 exhibited at least a 96% inhibition of cell proliferation at a concentration of 1.0 µL/mL. Taken together, the results from the WTS-1 proliferation assay demonstrated that treatment with OST-01 significantly reduces cellular proliferation in all AML cancer cell lines tested, further demonstrating the anti-oncogenic activity of OST-01 in leukemic cells.

TABLE 1

OST-01 Inhibition of Cell Proliferation in AML Cancer Cell Lines

| Treatment | Percent Cell Survival[1] | | |
|---|---|---|---|
| | MV-4-11 | KG-1A | Kasumi-1 |
| Untreated | 100% | 100% | 100% |
| 1.0 µL/mL OST-01 | 2% | 1% | 4% |

[1]The number of cell from the ethanol control was taken as 100% cell proliferation and that of OST-01 treated groups was calculated as percentage of ethanol control.

Immunoblotting analysis is a rapid and sensitive assay for the detection and characterization of proteins that works by exploiting the specificity inherent in antigen-antibody recognition. It involves the solubilization and electrophoretic separation of proteins by gel electrophoresis, followed by quantitative transfer and irreversible binding to a solid support substrate like nitrocellulose, PVDF, or nylon, and using polyclonal or monoclonal antibodies and a visualization assay to detect the presence of a protein of interest.

In one series of experiments, immunoblotting analysis was conducted on AML cell lines to determine the expression levels of the proliferating cell nuclear antigen (PCNA) protein. The PCNA protein is synthesized in early G1 and S phases of the cell cycle, functions in cell cycle progression, DNA replication and DNA repair. Thus, the presence of the PCNA protein serves as a biomarker for proliferation.

Separate cultures of MV-4-11, KG-1a, and Kasumi-1 cells were established in 10 cm culture dishes and grown to an approximate density of $10\times10^6$ cells. Either 1 µL/mL of OST-01 or 1 µL/mL control vehicle was then added to a culture for each of the three AML cell lines and incubated for 24 hours at 37° C. in 5% $CO_2$ incubator. After treatment, the cells were harvested and washed in ice-cold phosphate-buffered saline (PBS) and subsequently lysed in RIPA buffer containing 10 mM of a protease inhibitor cocktail (Thermo Scientific, CO). For immunoblotting, 50 µg of each cell lysate (in RIPA buffer) was separated on NuPAGE 4-12% gradient gels (Invitrogen, Carlsbad, CA), proteins transferred to a solid support substrate by Western blot. The solid support substrate was then incubated with either 1) an anti-PCNA mouse monoclonal antibody (PC-10, Santa Cruz, CA) and then an anti-mouse IgG HRP-linked secondary antibody (AB 7076, Cell Signaling, MA); or 2) an anti-Actin mouse monoclonal antibody (C4, Santa Cruz, CA) and then an anti-mouse IgG HRP-linked secondary antibody (AB 7076, Cell Signaling, MA). Actin is a protein constitutively expresses at constant levels in all cells and thus serves as a protein loading control. Immunocomplexes visualized using an enhanced chemiluminescence reagent (Thermo Scientific, CO).

Figure 2:
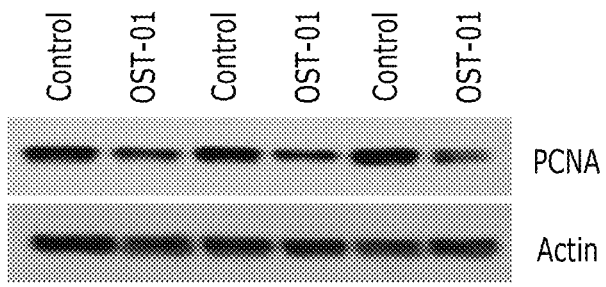
FIG. 2 shows a representative blot staining obtained from immunoblotting analyses examining the expression levels of the proliferation biomarker PCNA in cells from three different AML cell lines treated with either OST-01 or a vehicle control.
Figure 6A:
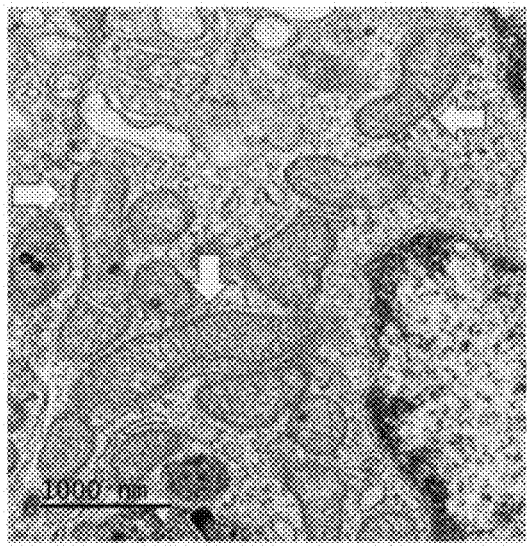
FIGS. 6A-6D show representative images obtained from transmission electron microscopy (TEM) in order to evaluate mitochondria morphology with FIG. 6A showing KG-1a cells treated with a vehicle control.
Figure 6B:
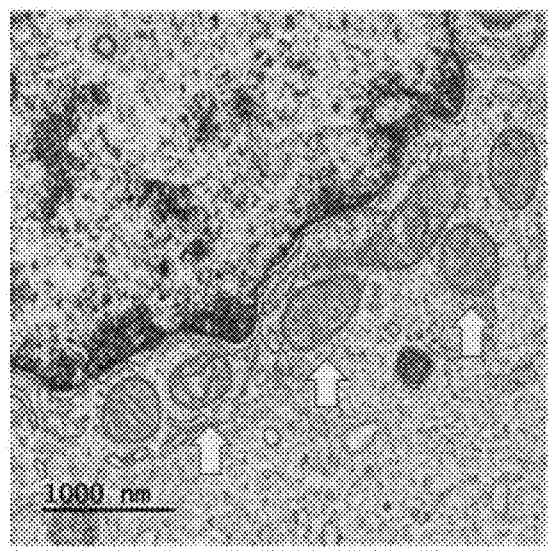
Figure 6C:
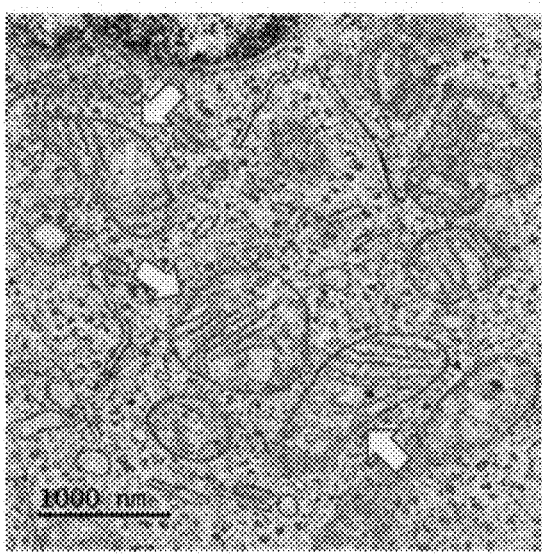
Figure 6D:
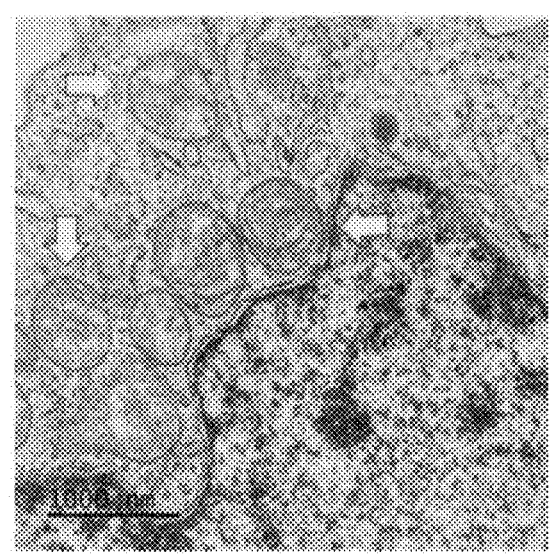
Figure 8A:
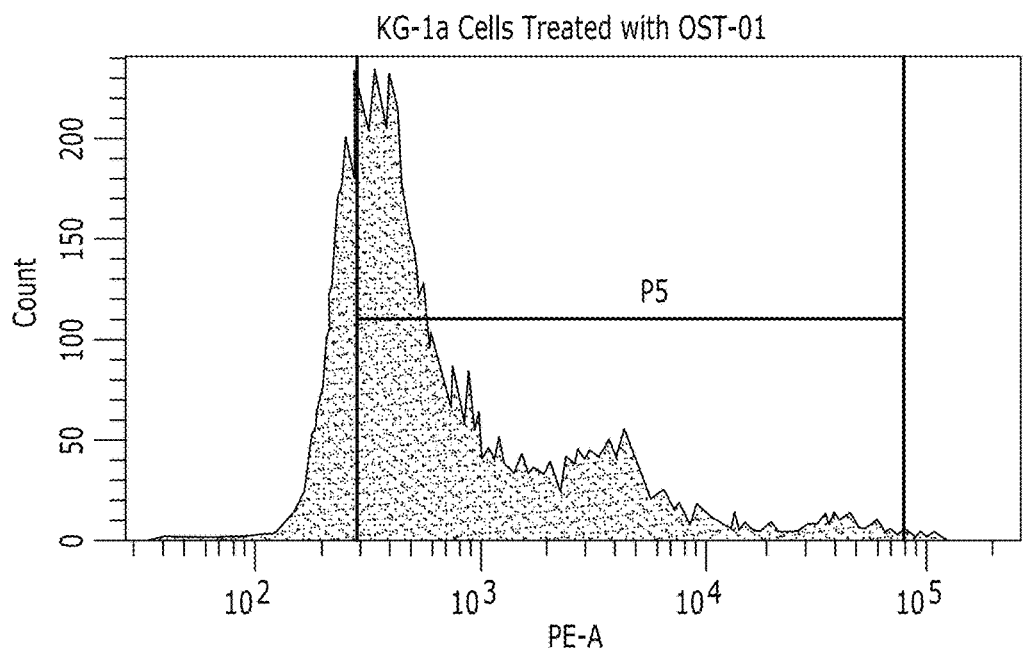
FIGS. 8A-8D show representative flow cytometry graphs obtained from superoxide activity assays with FIG. 8A showing KG-1a cells treated with OST-01.
Figure 8B:
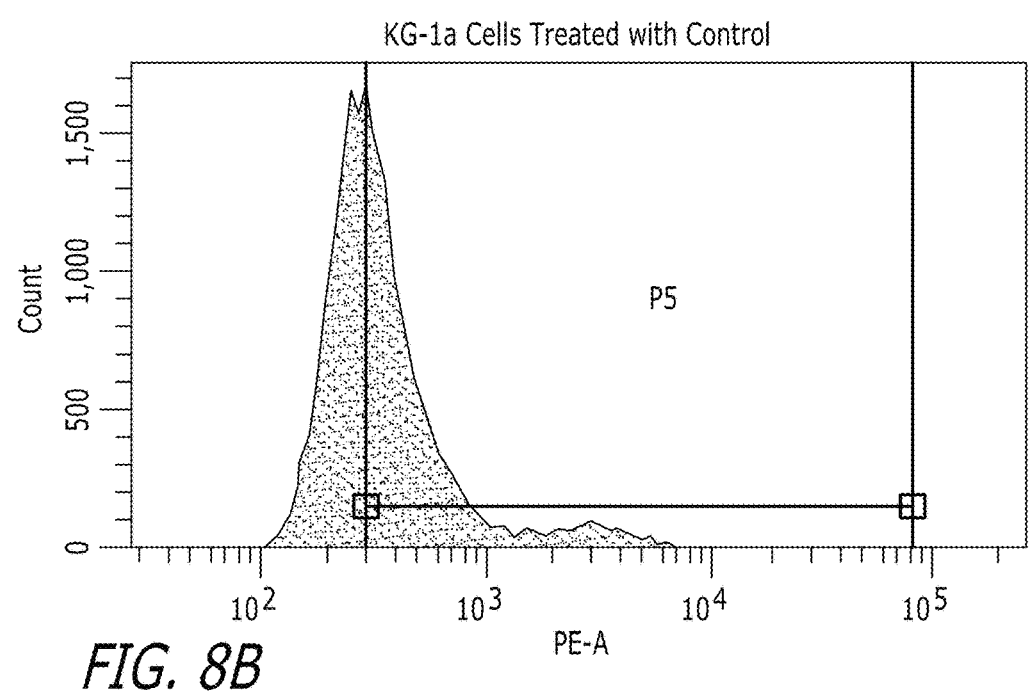
Figure 8C:
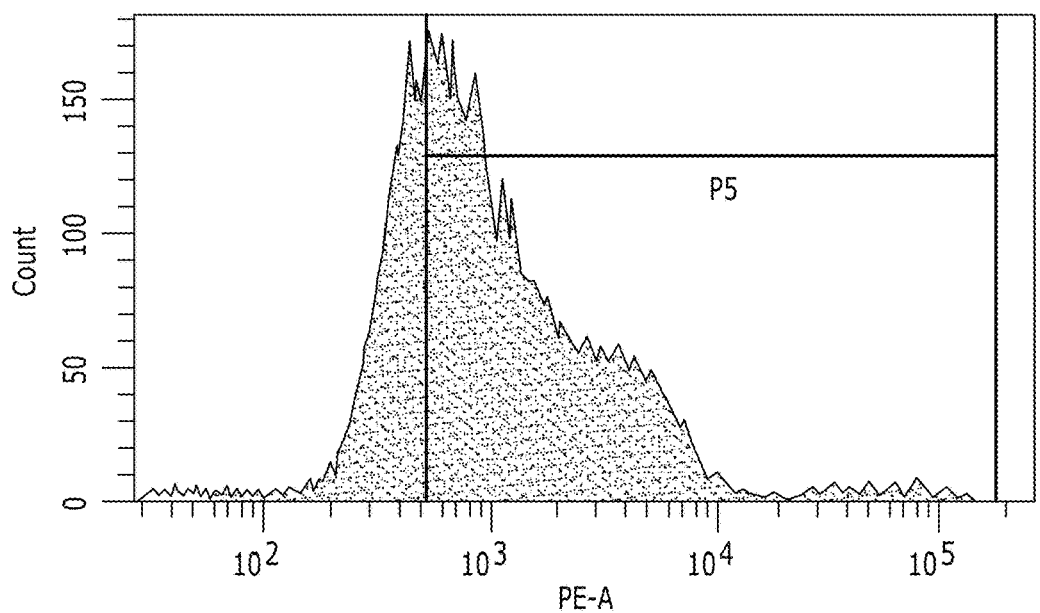
Figure 8D:
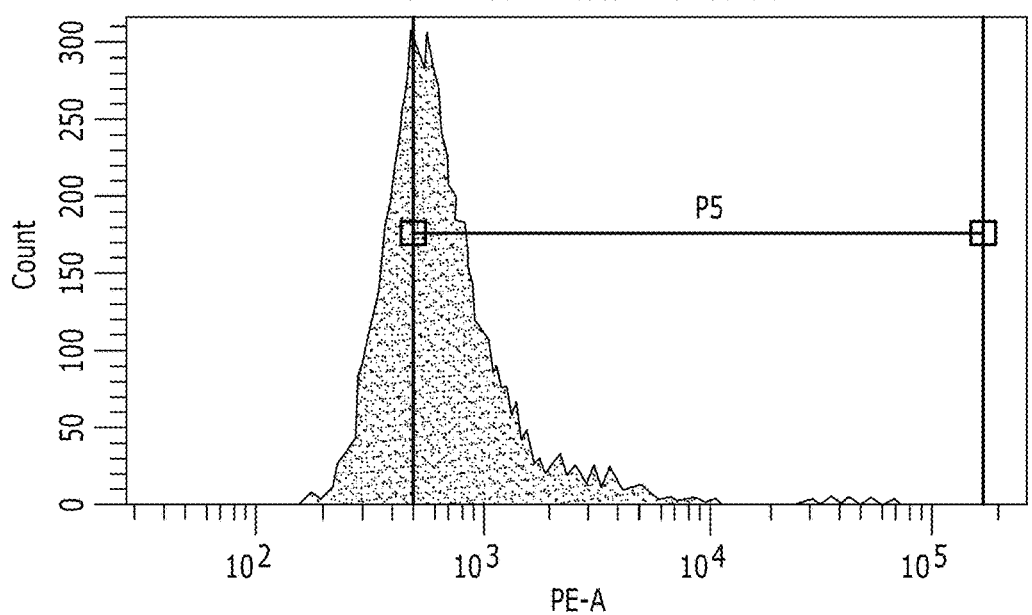
Figures 9A, 9B:
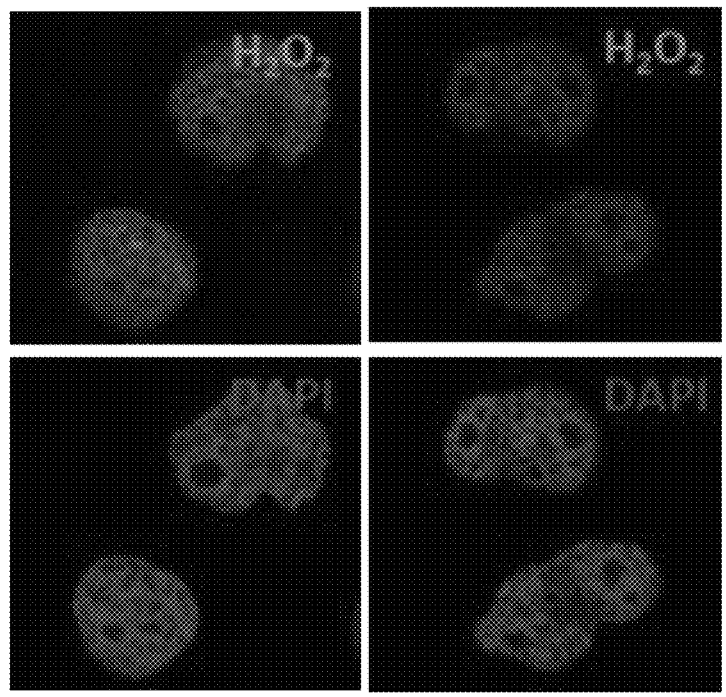
FIGS. 9A-9D show representative confocal images of red fluorescent indicator staining obtained from hydrogen peroxide assays with FIG. 9A showing KG-1a cells treated with OST-01.
Figures 9C, 9D:
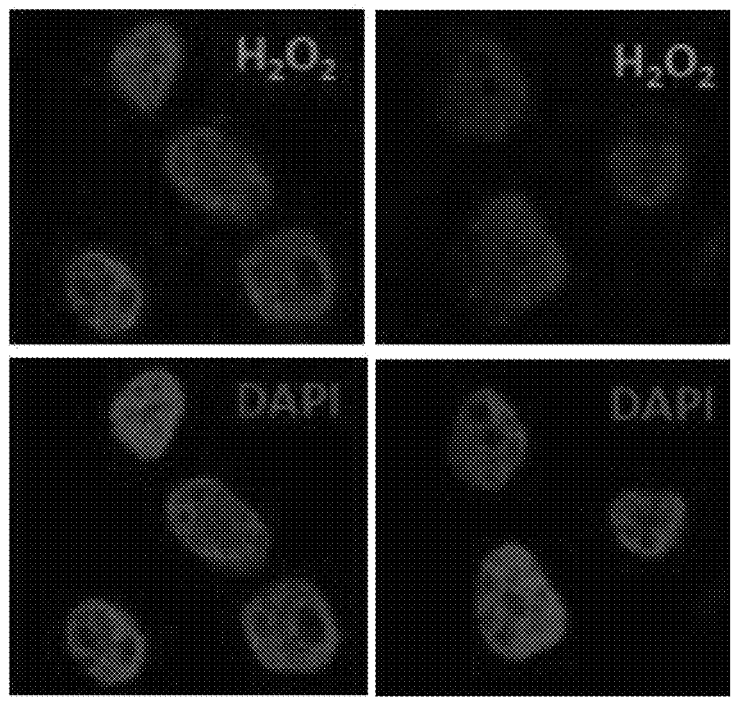

As shown in FIG. 2, results from the immunoblotting analysis demonstrated that treatment with OST-01 showed a dramatically decrease in the expression of PCNA as compared to the control in all AML cell lines tested. In each case, the expression of PCNA appears to have been reduced by 50% in OST-01 treated cells relative to the level observed in the control cells, even though actin levels were equivalent in both OST-01 treated and control cells. Taken together, the results from the immunoblotting analysis demonstrated that treatment with OST-01 significantly reduces a biomarker for cell proliferation in three different AML cell lines. These results are consistent with and confirm the findings from the MTS proliferation assay and further demonstrate that the anti-oncogenic activity of OST-01 includes inhibiting cell proliferation in non-solid cancer cells.

Example 3

OST-01 Induces Apoptosis in Leukemic Cells

To investigate the effects of OST-01 on apoptosis in leukemic cells, apoptosis flow cytometry assays, genomic DNA fragmentation assay, and immunoblotting analysis using biomarkers for apoptosis were conducted to determine whether OST-01 activity could induce apoptosis of leukemia cells.

The AML cell lines MV-4-11, KG-1a, and Kasumi-1 were selected for these studies and maintained as described in Example 2.

An apoptosis flow cytometry assay determines the number of cells associated with a fluorochrome-conjugated biomarker for apoptosis. One such apoptotic biomarker is Annexin V, a 35-36 kDa $Ca^{2+}$-dependent phospholipid-binding protein that has a high affinity for phosphatidylserine. In apoptotic cells, phosphatidylserine is translocated from the inner to the outer leaflet of the plasma membrane, thereby exposing phosphatidylserine to the external cellular environment. As such, assessing the level of Annexin V binding to cells with exposed phosphatidylserine serves as a sensitive biomarker for the number of cells undergoing apoptosis within a cell population. In addition, since externalization of phosphatidylserine occurs in the earlier stages of apoptosis, Annexin V binding identify apoptosis at an earlier stage than assays based on nuclear changes such as DNA fragmentation.

In one series of experiments, separate cultures of MV-4-11, KG-1a, and Kasumi-1 cells were established in 10 cm culture dishes and grown to an approximate density of $10 \times 10^6$ cells. Either 1 μL/mL of OST-01 or 1 μL/mL control vehicle was then added to a culture for each of the three AML cell lines and incubated for 24 hours at 37° C. in 5% $CO_2$ incubator. Cells were then assessed for apoptosis by an apoptosis flow cytometry assay employing with a fluorochrome-conjugated Annexin V and/or the fluorescent nucleic acid dye 4,6-diamidino-2-phenylindole (DAPI) (APC Annexin V, BD Bioscience, CA) following protocols provided by the manufacture. Briefly, after OST-01 treatment, cells were washed twice with an Annexin V buffered solution, resuspended in the same buffer at a concentration of $1 \times 10^6$ cells/mL, and 100 μL aliquoted transferred to 1 mL culture tubes. Aliquots were then incubated in the dark for 15 minutes with either 1) an Annexin-V-APC conjugate and DAPI, 1) an Annexin-V-APC conjugate; or 3) DAPI. An unstained aliquot was also set up as a negative control to define the basal level of apoptotic and dead cells. The percentage of cells that have been induced to undergo apoptosis is then determined by subtracting the percentage of apoptotic cells in the unstained aliquot from percentage of apoptotic cells in the stained aliquot. After staining, cells were washed in ice-cold PBS and resuspended in 300 μL of the Annexin V buffered solution, and analysis by flow cytometry using an LSR II flow cytometer (BD Bioscience, CA). Cells that were Annexin V negative and DAPI negative are considered healthy cells, Annexin V positive and DAPI negative cells are considered apoptotic, and cells that are positive to both Annexin V and DAPI are considered necrotic. Mean cell numbers between the OST-01 treated and control group was statistically analyzed by using unpaired, two-tailed Student's t test, with values from at least two independent experiments with triplicate determination. Data are presented as mean±standard error (SE) and a $p<0.05$ was considered statistically significant.

As shown in FIGS. 3A-3C, results from the apoptosis flow cytometry assay demonstrated that treatment with OST-01 exhibited in a statistically significant increase in Annexin V positive cells as compared to the control in all AML cell lines tested. For example, MV-4-11 cells treated with OST-01 showed at least a 9-fold increase in Annexin V positive cells relative to cells treated with the vehicle control (see FIG. 3A, $p<0.0001$), KG-1a cells treated with OST-01 showed over an 8-fold increase in Annexin V positive cells relative to cells treated with the vehicle control (see FIG. 3B, $p<0.0001$), and Kasumi-1 cells treated with OST-01 showed at least a 14-fold increase in Annexin V positive cells relative to cells treated with the vehicle control (see FIG. 3C, $p<0.0001$). Taken together, the results from the apoptosis flow cytometry assay demonstrated that treatment with OST-01 significantly increased the number of cells undergoing apoptosis in three different AML cell lines, further demonstrating that the anti-oncogenic activity of OST-01 extends to the induction of programed cell death and apoptosis in non-solid cancer cells.

A genomic DNA fragmentation assay determines the presence of DNA fragments, a known biomarker for apoptosis. Apoptosis is characterized by the activation of endogenous endonucleases, particularly the caspase-3 activated DNase (CAD). CAD cleaves genomic DNA at internucleosomal linker regions, resulting in DNA fragments that are multiples of 180-185 base-pairs in length. Thus, apoptotic DNA fragmentation is a key feature of apoptosis and a useful biomarker for identifying apoptotic cells. A DNA laddering assay is a genomic DNA fragmentation assay that separates DNA fragments by agarose gel electrophoresis and subsequent visualization these fragments using a DNA stain, such as, e.g., ethidium bromide, results in a characteristic "ladder" pattern of the separated DNA fragments. Thus, DNA laddering is a distinctive feature of DNA degraded by CAD. While most of the morphological features of apoptotic cells are short-lived, DNA laddering can be used as final state read-out method and has therefore become a reliable method to distinguish apoptosis from necrosis.

In one series of experiments, separate cultures of MV-4-11, KG-1a, and Kasumi-1 cells were established in 10 cm culture dishes and grown to an approximate density of $10 \times 10^6$ cells. Either 1 μL/mL of OST-01 or 1 μL/mL control vehicle was then added to a culture for each of the three AML cell lines and incubated for 24 hours at 37° C. in 5% $CO_2$ incubator. After treatment, cells were lysed by adding 500 μL of a lysis buffer containing 0.02% SDS, 1% Nonidet P-40, and 0.2 mg/mL proteinase K in PBS was incubating the cells on ice in for 60 minutes. Genomic DNA was extracted using a standard phenol/chloroform extraction method. The resulting DNA pellet was resuspended in 50 μL of TE buffer (supplemented with 10 mg/mL RNase A) and incubated at 37° C. for 2 hours to ensure complete elimination of RNA. A total of 10 μg of DNA was then separated on a 2% agarose gel, stained using an ethidium bromide solution, and visualized under UV light.

As shown in FIG. 4, results from the genomic DNA fragmentation assay demonstrated that treatment with OST-01 showed in a clearly significant increase in DNA fragmentation as compared to the control in all AML cell lines tested. In each case, a high degree of DNA fragmentation was observed in cells treated with OST-01 with no appreciable DNA fragmentation seen in the control cells. Taken together, the results from the DNA fragmentation assay demonstrated that treatment with OST-01 significantly increases DNA fragmentation in three different AML cell lines. These results are consistent with and confirm the results from the apoptosis flow cytometry assay and further demonstrate that the anti-oncogenic activity of OST-01 includes the induction of programed cell death and apoptosis in non-solid cancer cells.

As for cell proliferation experiment in Example 2, immunoblotting analysis is another useful assessment for the presence of apoptosis by determining the presence of biomarkers for this programed cell death process.

In one series of experiments, immunoblotting analysis was conducted on AML cell lines to determine the presence of the four apoptosis biomarkers, PARP, p53, phosphorylated H2A.X, and cleaved caspase-3. PARP is a 116 kDa nuclear poly(ADP-ribose) polymerase involved in DNA repair in response to environmental stress and helps cells to maintain their viability. PARP is one of the main cleavage targets of caspase-3, which facilitates cellular disassembly. Thus, the presence of cleaved PARP can serve as a marker of cells undergoing apoptosis. p53 is a tumor suppressor protein plays a major role in cellular response to DNA damage and other genomic aberrations. Activation of p53 can lead to either cell cycle arrest and DNA repair or apoptosis. Thus, the presence of p53 can serve as a marker of cells undergoing apoptosis. H2A.X is a variant histone required for checkpoint-mediated cell cycle arrest and DNA repair following double-stranded DNA breaks. DNA damage results in the rapid phosphorylation of H2A.X at serine 139 by PI3K-like kinases. Thus, H2A.X phosphorylation can serve as a marker of cells undergoing apoptosis. Caspase-3 is a critical executioner of apoptosis, as it is either partially or totally responsible for the proteolytic cleavage of many key proteins. Activation of caspase-3 requires proteolytic processing of its inactive zymogen into activated p17 and p12 fragments. Thus, the presence of cleaved Caspase-3 can serve as a marker of cells undergoing apoptosis.

Separate cultures of MV-4-11, KG-1a, and Kasumi-1 cells were established in 10 cm culture dishes and grown to an approximate density of $10 \times 10^6$ cells. Either 1 μL/mL of OST-01 or 1 μL/mL control vehicle was then added to a culture for each AML cell line and incubated for 24 hours at 37° C. in 5% $CO_2$ incubator. After treatment, the cells were washed and harvested in ice-cold PBS and subsequently lysed in RIPA buffer containing 10 mM of a protease inhibitor cocktail (Thermo Scientific, CO). For immunoblotting, 50 μg of each cell lysate (in RIPA buffer) was separated on NuPAGE 4-12% gradient gels (Invitrogen, Carlsbad, CA), proteins transferred to a solid support substrate by Western blot. The solid support substrate was then incubated with either 1) an anti-PARP rabbit polyclonal antibody (AB 9542, Cell Signaling, MA) and then an anti-rabbit IgG HRP-linked secondary antibody (AB 7074, Cell Signaling, MA); 2) an anti-p53 mouse monoclonal antibody (DO-10, Santa Cruz, CA) and then an anti-mouse IgG HRP-linked secondary antibody (AB 7076, Cell Signaling, MA); 3) an anti-γH2AX(phospho 139) mouse monoclonal antibody (AB 22551, Abcam, MA) and then an anti-mouse IgG HRP-linked secondary antibody (AB 7076, Cell Signaling, MA); 4) an anti-cleaved caspase 3 rabbit polyclonal antibody (AB 9579, Cell Signaling, MA) and then an anti-rabbit IgG HRP-linked secondary antibody (AB 7074, Cell Signaling, MA); or 5) or an anti-actin mouse monoclonal antibody (C4, Santa Cruz, CA) and then an anti-mouse IgG HRP-linked secondary antibody (AB 7076, Cell Signaling, MA). Actin is a protein constitutively expresses at constant levels in all cells and thus served as a protein loading control. Immunocomplexes visualized using an enhanced chemiluminescence reagent (Thermo Scientific, CO).

As shown in FIG. 5, results from the immunoblotting analysis demonstrated that treatment with OST-01 showed a dramatically increase in the presence of all biomarkers for apoptosis as compared to the control in all AML cell lines tested. As a preliminary matter, FIG. 5 shows that all samples exhibit equivalent levels of actin immunostaining indicated that equal amounts of total protein were loaded in each lane. However, when assessing for the presence of cleaved PARP and caspase-3, cells treated with OST-01 showed significant increase detection of these cleaved products relative to cells treated with the vehicle control (see FIG. 5). With respect to the presence of p53, both MV-4-11 and Kasumi-1 cells exhibited at least a 50% increase in the amount of p53 detected relative to cells treated with the vehicle control (see FIG. 5). p53 was not detected at all in KG-1a cells, both OST-01 treated and controls due to the deleted mutation of p53 in this cell line. With respect to the presence of phosphorylated H2A.X, both MV-4-11 and Kasumi-1 cells exhibited at least a 400% increase in the amount of phosphorylated H2A.X detected relative to cells treated with the vehicle control (see FIG. 5). Phosphorylated H2A.X was not detected at any appreciable levels in KG-1a cells, both OST-01 treated and controls.

Taken together, the results from the immunoblotting analysis demonstrated that treatment with OST-01 significantly increased the presence of biomarkers for apoptosis in three different AML cell lines. These results are consistent with and confirm the results obtained from experiments involving the apoptosis flow cytometry and DNA fragmentation assays, and further demonstrate the anti-oncogenic activity of OST-01 includes the induction of programed cell death and apoptosis in non-solid cancer cells.

Example 4

OST-01 Induces Mitochondrial Disfunction in Leukemic Cells

To investigate the effects of OST-01 on the health of leukemic cells, both the evaluation of morphological changes of mitochondria and its membrane potential was conducted to determine whether OST-01 activity affected mitochondrial morphology and function in leukemia cells.

The AML cell lines KG-1a and Kasumi-1 were selected for these studies and maintained as described in Example 2.

The most important function of mitochondria is to produce energy through the process of electron transport and oxidative phosphorylation, the driving force behind ATP production. Healthy mitochondria are double-membraned, spheroid-shaped, organelle having a diameter of 0.5 um to 1.0 um and structurally comprises an outer membrane and an inner membrane separated by the intermembrane space and an interior filled with by the matrix. The outer membrane is freely permeable to ions, nutrient molecules, energy molecules like the ADP and ATP. The inner membrane is strictly permeable only to oxygen and to ATP. It undergoes a complex folding pattern to form a layered structure called cristae, which increases the surface area inside the organelle. A number of chemical reactions take place within the cristae and is essential to the production of ATP. Mitochondria intrinsically sense their state of health, and when under stress, induce compensatory quality-control mechanisms, such as stress-induced mitochondrial hyperfusion (SIMH) or fission and degradation of damaged mitochondria (mitophagy). As such, changes in mitochondrial morphology and function are good indicators of cell health.

In one series of experiments, separate cultures of KG-1a and Kasumi-1 cells were established in 3 cm culture dishes and grown to an approximate density of $1\times10^6$ cells. Either 1 µL/mL of OST-01 or 1 µL/mL control vehicle was then added to a culture for each AML cell line and incubated for 24 hours at 37° C. in 5% $CO_2$ incubator. The morphology of mitochondria in these treated cells were then assessed by TEM. Treated cells were fixed with 2.5% glutaraldehyte, 0.1M Cacodylate buffer ($Na(CH_3)_2AsO_2 \cdot 3H_2O$), pH 7.2, at 4° C. Fixed cells were prepared for TEM using standard procedures including post-fixation with osmium tetroxide, serial dehydration with ethanol, and embedment in Eponate. Ultra-thin sections (70 nm thick) were acquired by ultramicrotomy, post-stained, and examined on a FEI Tecnai 12 transmission electron microscope equipped with a Gatan OneView CMOS camera. TEM images were taken at nominal 11,000× magnification.

As shown in FIGS. 6A-6D, results from the TEM analysis demonstrated that treatment with OST-01 showed a dramatically affected in mitochondria morphology as compared to the control in all AML cell lines tested. For example, KG-1a cells treated with OST-01 exhibited a significant decrease of mitochondria size relative to cells treated with the vehicle control (see arrowheads in FIGS. 6A & 6B). Moreover, the mitochondria in OST-01 treated KG-1a cells lose the cristate structure comparing to controlled cells. Similar decreased in mitochondrial size cristate structure loss were observed Kasumi-1 cells treated with OST-01 relative to cells treated with the vehicle control (see arrowheads in FIGS. 6C & 6D). Taken together, the results from the TEM analysis demonstrated that treatment with OST-01 significantly affects the morphology of mitochondria AML cell lines treated with OST-01. In addition, the loss of cristate structure suggests that OST-01 treatment disrupts the regulation of mitochondria dynamic (fusion vs fission) and mitochondria metabolism function. These results provide additional evidence that the anti-oncogenic activity of OST-01 extends to the disruption of mitochondrial function in non-solid cancer cells.

Mitochondrial membrane potential (MMP) is a key indicator of mitochondrial activity because it reflects the process of electron transport and oxidative phosphorylation. Hence, mitochondrial and cell health are interrelated and mitochondrial membrane potential is one of the features too look for when studying mechanisms related to cell health and when testing drugs. MMP decrease results in ATP depletion along with changes in the pH of mitochondrial intermembrane space and matrix. To take advantage of this pH change, fluorescent dyes have been developed that accumulate in healthy mitochondria depending on the pH. Once such dye, JC-1, a cationic carbocyanine dye that exhibits potential-dependent accumulation in mitochondria, existing as a monomer at low concentrations and yields green fluorescence but forms J-aggregates at higher concentrations and produces red fluorescence. This concentration-dependent formation of red fluorescent J-aggregates make JC-1a sensitive marker for mitochondrial membrane potential and allows to distinguish cells with low or high mitochondria potential.

In one series of experiments, cultures of Kasumi-1 cells were established in 3 cm culture dishes and grown to an approximate density of $1\times10^6$ cells. Either 1 µL/mL of OST-01 or 1 µL/mL control vehicle was then added to a culture and incubated for 24 hours at 37° C. in 5% $CO_2$ incubator. Cells were then visualized for mitochondrial membrane potential quantifying JC-1 stained cells using confocal microscopy (JC-1 and JC-9 Mitochondrial Potential Sensors, Invitrogen, CA) following protocols provided by the manufacture. Briefly, after OST-01 treatment, cells were harvested and washed in ice-cold PBS, and mounted on glass slides using by cytocentrifuging at 600 rpm for 10 minutes (CytoSpin4, Epredia, MI). Cells were then washed in ice-cold PBS, fixed in 4% paraformaldehyde for 15 minutes and permeabilized in 0.5% Triton X-100 for 15 minutes. Fixed cells were stained with JC-1 dye at 37° C. for 1 hour and analyzed by confocal microscope (LSM880, Zeiss) and detection emission levels at 529 nm and 590 nm.

As shown in FIGS. 7A-7F, results from the confocal analysis demonstrated that treatment with OST-01 showed a dramatically decreased in mitochondrial depolarization as compared to the vehicle control in AML cells. For example, Kasumi-1 cells treated with control exhibited a higher emission of red fluorescence inside their mitochondria (see FIG. 7A) as compared to the presence of green fluorescence emission (see FIG. 7B), resulting in increased ratio of red/green signal (see FIG. 7C). Such red signal predominance from the mitochondria of control cells reveals a higher accumulation of J-aggregate form of JC-1 and is indicative of proper membrane potential and cell health. Conversely, Kasumi-1 cells treated with OST-01 exhibited a lower emission of red fluorescence inside their mitochondria (see FIG. 7D) as compared to the presence of green fluorescence emission (see FIG. 7E) resulting in decreased ratio of red/green signal (see FIG. 7F). Such green signal predominance from the mitochondria of OST-01 treated cells reveals a higher accumulation of the monomeric form of JC-1 and is indicative of improper membrane potential and poor cell health. Taken together, the results from the mitochondrial membrane potential assay demonstrated that treatment with OST-01 significantly decreases mitochondria membrane potential in AML cells. These results are consistent with and confirm the findings from the mitochondrial morphology analysis and further demonstrate that the anti-oncogenic activity of OST-01 includes disruption of mitochondrial function in non-solid cancer cells.

Example 5

OST-01 Induces Oxidative Stress in Leukemic Cells

To investigate the effects of OST-01 on oxidative stress in leukemic cells a superoxide activity assay and a hydrogen peroxide assay were conducted to determine whether OST-01 activity could induce oxidative stress of leukemia cells.

The AML cell lines KG-1a and Kasumi-1 were selected for these studies and maintained as described in Example 2.

Mitochondrial superoxide is generated as a byproduct of oxidative phosphorylation. In an otherwise tightly coupled electron transport chain, approximately 1% to 3% of mitochondrial oxygen consumed is incompletely reduced. These "leaky" electrons can quickly interact with molecular oxygen to form superoxide anion, the predominant reactive oxygen species (ROS) in mitochondria. Increases in cellular superoxide production are associated with oxidative stress.

A superoxide activity assay is designed to directly monitor real time superoxide production in live cells using fluorescence microscopy and/or flow cytometry. One such assay is the MitoSOX™ Red Mitochondrial Superoxide Indicator (Thermo Scientific, CO) that uses a MitoSOX™ Red reagent to quantify superoxide activity in live cells. The reagent is cell-permeable, selectively targets mitochondria, is rapidly oxidized by superoxide but not by other reactive oxygen species (ROS) and reactive nitrogen species (RNS). The oxidized product of the MitoSOX™ Red reagent is highly fluorescent upon binding to nucleic acid can be visualized in fluorescence microscopy and/or flow cytometry.

In one series of experiments, separate cultures of KG-1a and Kasumi-1 cells were established in 3 cm culture dishes and grown to an approximate density of $1\times10^6$ cells. Either 1 µL/mL of OST-01 or 1 µL/mL control vehicle was then added to a culture and incubated for 24 hours at 37° C. in 5% $CO_2$ incubator. Cells were then assessed for oxidative stress by a superoxide activity assay employing with a fluorescent indicator MitoSOX™ (MitoSOX™ Red Mitochondrial Superoxide Indicator, Thermo Scientific, CO) following protocols provided by the manufacture. Briefly, after OST-01 treatment, cells were washed twice in ice-cold PBS and incubated in the dark with a MitoSOX™ Red reagent solution for 30 minutes at 37° C. in 5% $CO_2$ incubator. Cells were then counterstained with the fluorescent nucleic acid dye DAPI to identify nuclei. After staining, cells were washed in warm PBS and analysis by flow cytometry using an LSR II flow cytometer (BD Bioscience, CA).

As shown in FIGS. 8A-8D, results from the superoxide activity assay demonstrated that treatment with OST-01 showed a dramatically increase in superoxide activity compared to the control in all AML cell lines tested. For example, KG-1a cells treated with OST-01 exhibited significant increase in ROS induction as signified by the dramatic increase in oxidized product of the MitoSOX™ Red reagent (see FIG. 8A) relative to cells treated with the vehicle control (see FIG. 8B). Similarly, Kasumi-1 cells treated with OST-01 exhibited significant increase in ROS induction as signified by the dramatic increase in oxidized product of the MitoSOX™ Red reagent (see FIG. 8C) relative to cells treated with the vehicle control (see FIG. 8D). Taken together, the results from the superoxide activity assay demonstrated that treatment with OST-01 significantly increased ROS induction and, by inference, oxidative stress, in the AML cell lines tested. These findings provide further evidence of the effects that OST-01 has on mitochondrial function, and further demonstrate the anti-oncogenic activity of OST-01 in non-solid cancer cells.

Hydrogen peroxide is a reactive oxygen metabolic byproduct that serves as a key regulator for a number of oxidative stress-related states. A hydrogen peroxide assay is designed to directly monitor real time hydrogen peroxide production in live cells using fluorescence microscopy and/or flow cytometry. One such assay is the Hydrogen Peroxide Assay Kit which used an AbGreen indicator to quantify hydrogen peroxide in live cells. It is cell-permeable, and generates green fluorescence when it reacts with hydrogen peroxide.

In one series of experiments, separate cultures of KG-1a and Kasumi-1 cells were established in 3 cm culture dishes and grown to an approximate density of $1\times10^6$ cells. Either 1 µL/mL of OST-01 or 1 µL/mL control vehicle was to a culture for each AML cell line and incubated for 24 hours at 37° C. in 5% $CO_2$ incubator. Cells were then assessed for oxidative stress by a hydrogen peroxide assay employing with a red fluorescent indicator (Hydrogen Peroxide Assay Kit (Cell-based), Abcam, MA) following protocols provided by the manufacture. Briefly, after OST-01 treatment, cells were washed twice in ice-cold PBS and incubated in the dark with an red fluorescent indicator solution for 30 minutes at 37° C. in 5% $CO_2$ incubator. Cells were then counterstained with the fluorescent nucleic acid dye DAPI to identify nuclei. After staining, cells were washed with ice-cold PBS and analysis for fluorescence using a confocal microscope (Carl Zeiss, Jena, Germany).

As shown in FIGS. 9A-9D, results from the hydrogen peroxide assay demonstrated that treatment with OST-01 showed a dramatically increase in the presence of hydrogen peroxide as compared to the control in all AML cell lines tested. For example, KG-1a cells treated with OST-01 exhibited at least a two-fold higher intensity of red fluorescence (see FIG. 9A) relative to cells treated with the vehicle control (see FIG. 9B), even though DAPI levels were equivalent in both OST-01 treated and control cells. Similarly, Kasumi-1 cells treated with OST-01 exhibited at least a three-fold higher intensity of red fluorescence (see FIG. 9C) relative to cells treated with the vehicle control (see FIG. 9D), even though DAPI levels were equivalent in both OST-01 treated and control cells. Taken together, the results from the hydrogen peroxide assay demonstrated that treatment with OST-01 significantly increased hydrogen peroxide and, by inference, oxidative stress, in AML cell lines tested. These results are consistent with and confirm the findings from the ROS induction analysis and further demonstrate that the anti-oncogenic activity of OST-01 includes induction of oxidative stress in non-solid cancer cells.

Example 6

OST-01 Suppresses Cellular Metabolic Pathway Activity in Leukemic Cells

To investigate the effects of OST-01 on cellular metabolism in leukemic cells a fatty acid metabolism activity assay and an oxidative phosphorylation and glycolysis detection assay were conducted to determine whether OST-01 activity could disrupt cellular metabolism of leukemia cells.

The AML cell line KG-1a was selected for these studies and maintained as described in Example 2.

A fatty acid metabolism activity assay is an assay determining the efficiency of long chain fatty acid oxidation pathway in cells. Cancer cells may alter lipid metabolism or shift the balance between anabolic and catabolic processes to adapt to the nutritional conditions of the tumor microenvironment. These processes may be analyzed directly via metabolic measurements. Long chain fatty acids are a primary substrate fueling mitochondrial metabolism and reduction in long chain fatty acid oxidation has a profound impact on cell fate, function, and fitness.

In one series of experiments, cultures of KG-1a cells were established in 3 cm culture dishes and grown to an approximate density of $1\times10^6$ cells. Either 1 µL/mL of OST-01 or 1 µL/mL control vehicle was then added to a culture and incubated for 24 hours at 37° C. in 5% $CO_2$ incubator. After treatment, cells were washed in HBSS and incubated with 200 µL of 1 mCi/mL [$^3$H]-palmitic acid (Perkin Elmer, CA) bound to fatty-acid free albumin (palmitate:albumin ratio of 2:1) which serves as the substrate and 1 mM L-cartinine for 2 hours at 37° C. After incubation, the supernatant was collected and added to a tube containing 200 µL of cold 10% trichloroacetic acid, centrifuged for 10 minutes at 3,000 g at 4° C. Supernatant aliquots of 350 µL were then removed, neutralized with 55 µL of 6 N NaOH, and applied to an ion exchange column loaded with Dowex 1X2 chloride form resin (Sigma Aldrich, MO). Radioactive product bound to the column was eluted with water, the flow-through was collected, and radiation was quantified using liquid scintillation counting. Mean radioactive counts between the OST-01 treated and control group was statistically analyzed by using unpaired, two-tailed Student's t test, with values from at least two independent experiments with triplicate determination. Data are presented as mean±standard error (SE) and a p<0.05 was considered statistically significant.

Figure 10:
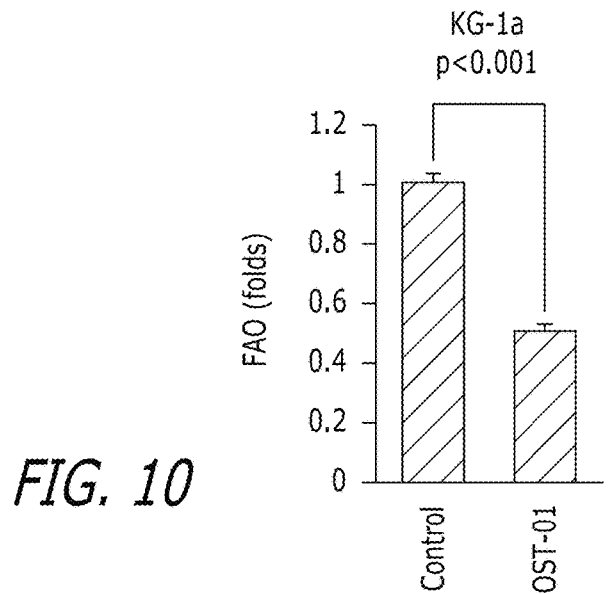
FIG. 10 shows a bar graph of the amount radioactive [$^3$H]-palmitate produced from fatty acid metabolism assays showing the results of KG-1a cells treated with either OST-01 or a vehicle control.

As shown in FIG. 10, results from the fatty acid metabolism activity assay demonstrated that treatment with OST-01 exhibited a statistically significant decrease in the amount of fatty acid metabolized as compared to the control in all AML cell lines tested. For example, KG-1a cells treated with OST-01 showed at least a 50% decrease in the amount radioactive [$^3$H]-palmitate product metabolized relative to cells treated with the vehicle control (see FIG. 10, p<0.001). Taken together, the results from the fatty acid metabolism activity assay demonstrated that treatment with OST-01 significantly reduces fatty acid metabolism in AML cells, demonstrating that the anti-oncogenic activity of OST-01 extends to disruption of fatty acid metabolism in non-solid cancer cells.

Cancer cells are highly dependent on metabolic pathways to generate the necessary energy for many oncogenic processes such as rapid proliferation, survival, invasion, and metastasis, and will reprogram their metabolism to support these processes. While normal cells generate ATP and biosynthetic precursors through a combination of oxidative and glycolytic metabolism, cancer cells dramatically reprogram their metabolism to support rapid, invasive, and metastatic growth. Cells with a glycolytic phenotype exhibit significantly higher rates of proton production (extracellular acidification rate, ECAR) than cells using oxidative phosphorylation (oxygen consumption rate, OCR). Treatment refractoriness or disease relapse of AML patients is broadly attributed to the persistence of the treatment-resistant quiescent leukemia stem cells (LSCs). Recently, it has been shown that LSCs differ from normal hematopoietic stem cells (HSCs) in the process of energy production, thus offering a potential strategy to specifically target LSCs. In fact, while normal HSCs utilize both glycolysis and oxidative phosphorylation (OXPHOS) for energy production, LSCs are highly dependent on OXPHOS. In one series of experiments, KG-1a cells were grown to an appropriate density and approximately 40,000 cells/200 µL were seeded into wells of 96-well cell culture microplate. Either 1 µL/mL of OST-01 (1×), 2 µL/mL of OST-01 (2×), or 1 µL/mL control vehicle was then added to transferred cells for each of the three AML cell lines and incubated for 24 hours at 37° C. in 5% CO$_2$ incubator. As a negative control, three wells were kept devoid of cells and given only Seahorse media (pH 7.4), which is comprised of basal XF media, 5.5 mM glucose, 1 mM sodium pyruvate, and 4 mM glutamine. Cell growth was then assessed using an oxidative phosphorylation and glycolysis detection assay (XF96 Extracellular Flux Analyzer (Seahorse Bioscience, MA) following protocols provided by the manufacture. Briefly, 12 hours prior to running a plate, a Seahorse sensor cartridge was incubated with Seahorse Calibrant at 37° C. in CO$_2$-free incubator. On the day of an assay, cells were washed and incubated with Seahorse media. The sensor cartridge was fitted onto the cell culture microplate, which was then placed into a 37° C., CO$_2$-free incubator for one hour. During the assay, which was run on the Seahorse XF96 Analyzer, the following inhibitors were injected sequentially, as is standard for the Cell Energy Test: 1 mM oligomycin, 0.5 mM FCCP. Mean values between the OST-01 treated and control group was statistically analyzed by using unpaired, two-tailed Student's t test, with values from at least two independent experiments with triplicate determination. Data are presented as mean±standard error (SE) and a p<0.05 was considered statistically significant.

Figures 11A, 11B:
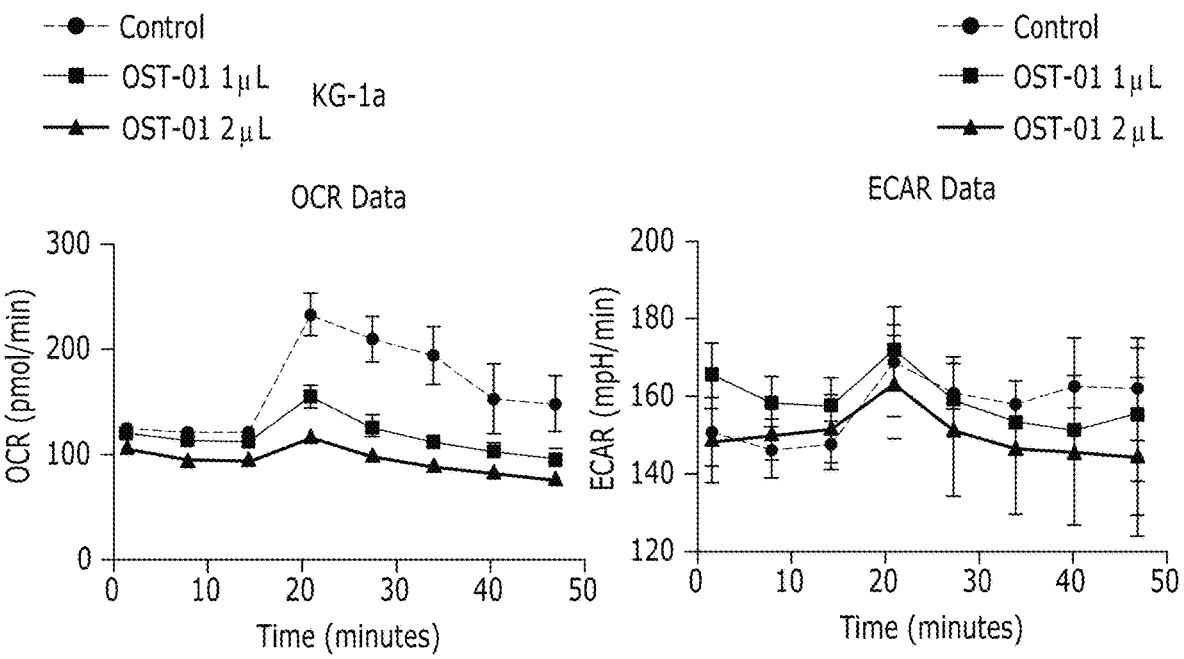
FIGS. 11A-11B show graphs of results obtained from oxidative phosphorylation and glycolysis detection assays with FIG. 11A showing oxygen consumption (OCR) rates of KG-1a cells treated with either 1 µL OST-01, 2 µL OST-01, or a vehicle control.

As shown in FIGS. 11A-11B, results from the oxidative phosphorylation and glycolysis detection assay demonstrated that treatment with OST-01 exhibited a statistically significant inhibition of oxidative phosphorylation but not glycolysis. For example, KG-1a cells treated with OST-01 exhibited significant oxygen consumption rates relative to cells treated with the vehicle control by at least one standard deviation (see FIG. 11A, p<0.016). In addition, OST-01 treatment demonstrated a dose-response inhibitory effect on oxidative phosphorylation with the 2× dose showing greater oxygen consumption rates relative to the 1× dose (see FIG. 11A, p<0.001). On the other hand, KG-1a cells treated with OST-01 showed no statistically relevant difference in extracellular acidification rates when compared to cells treated with the vehicle control (see FIG. 11B). Taken together, the results demonstrated that treatment with OST-01 significantly inhibits oxidative phosphorylation in AML cells, demonstrating that the anti-oncogenic activity of OST-01 extends to the disruption of ATP production in non-solid cancer cells.

Example 7

OST-01 Suppresses Ribosomal RNA (rRNA) Synthesis in Leukemic Cells

To investigate the effects of OST-01 on rRNA synthesis in leukemic cells, rRNA synthesis assays were conducted to determine whether OST-01 activity could reduce rRNA synthesis in leukemia cells.

Actively growing cells depend on the continuous production of large amounts of ribosomes, including rRNA. RNA polymerase I (Pol 1) accounts for up to 60% of the total RNA synthesized in the nucleus and transcribes the precursors of the three largest species of rRNA, 28S, 18S and 5.8S, but not 5S rRNA. As such, rRNA synthesis is a fundamental process utilized by all cells and targeting of this process for therapeutic intervention in cancer was long deemed not feasible. However, the dependence on increased rDNA transcription appears to selectively render cancer cells vulnerable to therapeutic intervention in the rRNA synthesis process. Elevated levels of rRNA represent a common feature of cancer cells, and numerous reports indicate that rRNA synthesis is important for cancer and leukemia cell proliferation. To determine the levels of rRNA synthesis, both the level of 5' external transcribed spacer (5' ETS) and the degree of [$^{32}$P] radioisotope labeling of RNA were assessed in AML blast cells isolated from patients and mononuclear cells (MNC), serving as a normal cell control.

Ribosomal subunits are assembled on a precursor rRNA that includes four spacers in addition to mature rRNA sequences. The 5' ETS is the most prominent spacer that recruits U3 snoRNA and a plethora of proteins during the early assembly of 90S small subunit preribosomes. As such, the 5' ETS is a biomarker for the presence of rRNA and hence can be used to assess the level of rRNA synthesis.

In one series of experiments, separate cultures of AML blast cells and MNCs isolated from three different patients were established in 10 cm culture dishes and grown to an approximate density of 10×10$^6$ cells. Total RNA was isolated from these cells using a phenol-chloroform RNA purification method following protocols provided by the manufacture (RNeasy Mini Kit, Qiagen, CA). First-strand cDNA was synthesized from the purified RNA using the SuperScript Ill First Strand Kit, and the presence of 5' ETS was determined by amplifying this cDNA with forward and reverse primers specific for 5' ETS using quantitative-PCR (q-PCR; TaqMan Gene Expression Assays, Thermo Fisher, MA). Forward and reverse primers specific for GAPDH was used as an internal control.

Figure 12A:
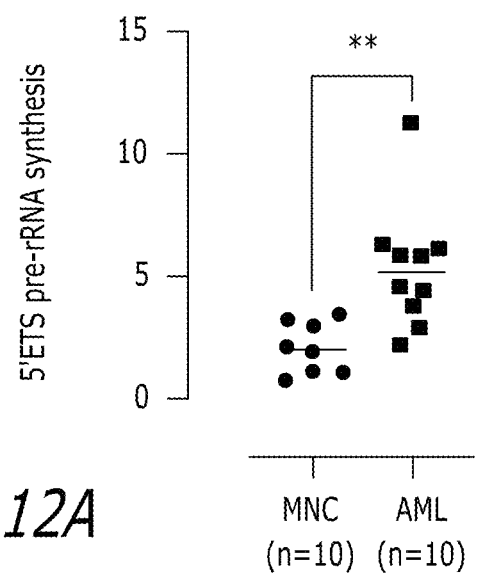
FIGS. 12A-12B show differential effects of OST-01 on ribosomal RNA (rRNA) synthesis in AML blast cells and MNCs.

As shown in FIG. 12A, 5' ETS levels were significantly higher in AML blast cells by at least a 2-fold as compared to 5' ETS levels MNCs (p=0.0035), indicating that rRNA synthesis levels was significantly upregulated in AML blast cells comparing to MNCs.

RNA radiolabeling assays takes advantage of the cellular processes of transcription to assessing the degree of incorporation of a necessary component that is labeled with a radioactive isotope. Such assays can easily produce uniformly radiolabeled RNA molecules that can be quantitated.

In one series of experiments, separate cultures of AML blast cells and MNCs isolated from three different patients were established in 10 cm culture dishes and grown to an approximate density of $10 \times 10^6$ cells. These cell cultures were then washed and incubated in phosphate-free media supplemented with 10% FBS for 2 hours followed by incubation with 0.5 mCi [$^{32}$P] orthophosphate for one hour. Total RNA was isolated from these incubated cells using a phenol-chloroform RNA purification method following protocols provided by the manufacture (TRIzol, Qiagen, CA). This purified RNA was quantified using standard procedures and 10 µg of this RNA was separated on a 1.2% MOPS formaldehyde gel. Gels were dried and visualized by autoradiography.

Figure 12B:
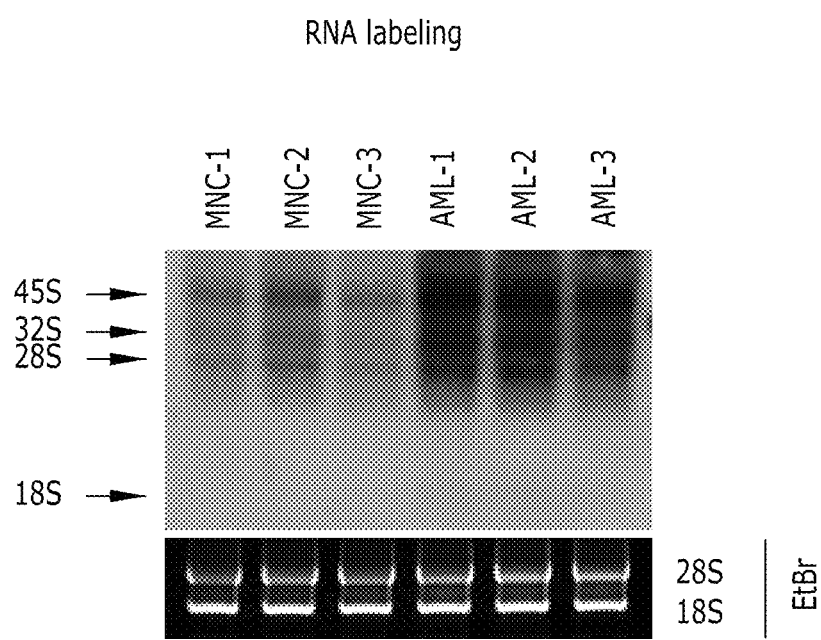

As shown in FIG. 12B, levels of [$^{32}$P]-labeled RNA were significantly higher in AML blast cells by at least 4-fold as compared to levels of [$^{32}$P]-labeled RNA isolated from MNCs, indicating that rRNA synthesis levels was significantly upregulated in AML blast cells compared to MNCs.

To determine whether OST-01 could affect rRNA synthesis in AML cells, levels of rRNA synthesis were determined in AML blast cells and MNCs treated with OST-01 or control vehicle. Separate cultures of AML blast cells and MNCs isolated from five different patients were established in 10 cm culture dishes and grown to an approximate density of $10 \times 10^6$ cells. Either 1 µL/mL of OST-01 or 1 µL/mL control vehicle was then added to a culture and incubated for 24 hours at 37° C. in 5% $CO_2$ incubator. After treatment, levels of rRNA synthesis were assessed using both the 5' ETS q-PCR and [$^{32}$P]-labeling assays disclosed herein. Mean 5' ETS amplification values between the OST-01 treated and control group was statistically analyzed by using unpaired, two-tailed Student's t test, with values from at least two independent experiments with triplicate determination. Data are presented as mean±standard error (SE) and a $p<0.05$ was considered statistically significant.

Figure 13A:
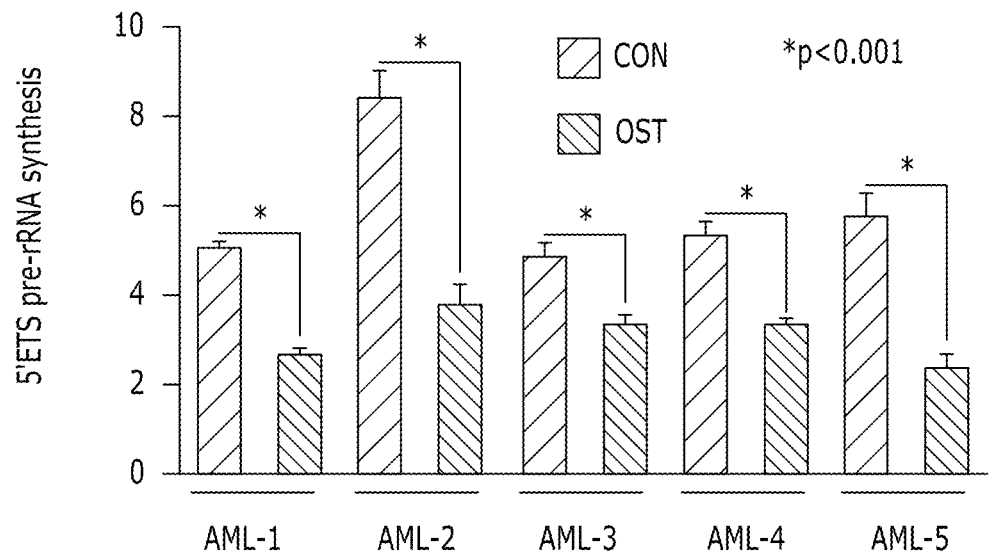
FIGS. 13A-13F show differential effects of OST-01 on AML blast cells relative to MNCs treated with either OST-01 or a vehicle control.
Figure 13B:
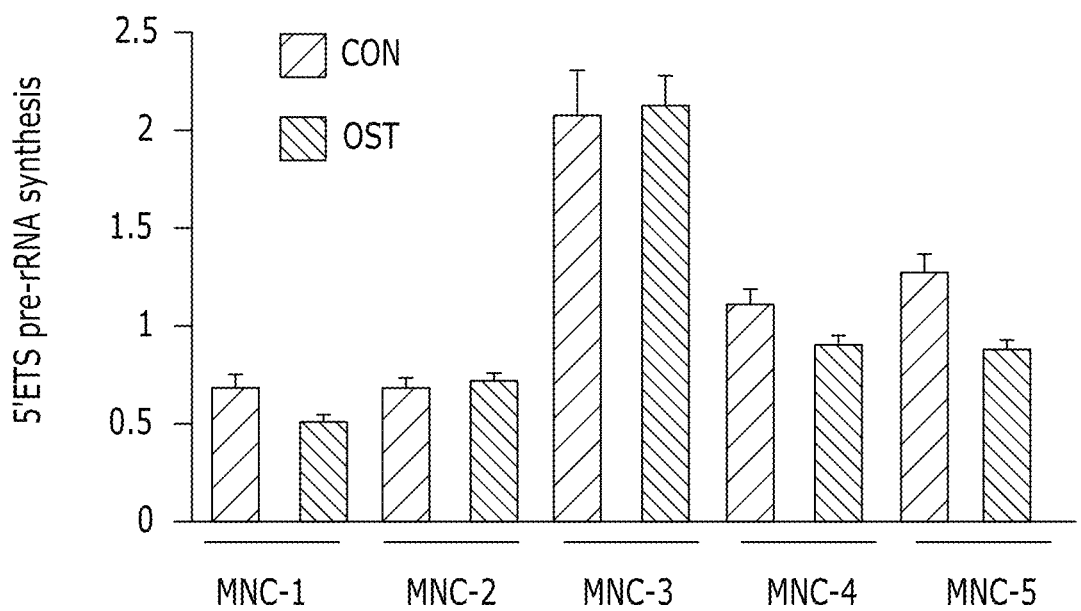

As shown in FIGS. 13A-13B, 5' ETS levels were significantly lower in AML blast cells treated with OST-01 as compared to 5' ETS levels in AML blast cells treated with vehicle control, indicating that rRNA synthesis levels was significantly inhibited in AML blast cells treated with OST-01 compared to untreated controls. For example, cultures of AML blast cells from patient 1 treated with OST-01 exhibited a significant decrease in 5' ETS levels by about a 2-fold as compared to 5' ETS levels isolated from cultures of AML blast cells from patient 1 treated with the vehicle control (p<0.001); cultures of AML blast cells from patient 2 treated with OST-01 exhibited a significant decrease in 5' ETS levels by at least a 2-fold as compared to 5' ETS levels isolated from cultures of AML blast cells from patient 2 treated with the vehicle control (p<0.001); cultures of AML blast cells from patient 3 treated with OST-01 exhibited a significant decrease in 5' ETS levels by about a 1-fold as compared to 5' ETS levels isolated from cultures of AML blast cells from patient 3 treated with the vehicle control (p<0.001); cultures of AML blast cells from patient 4 treated with OST-01 exhibited a significant decrease in 5' ETS levels by about a 1-fold as compared to 5' ETS levels isolated from cultures of AML blast cells from patient 4 treated with the vehicle control (p<0.001); and cultures of AML blast cells from patient 5 treated with OST-01 exhibited a significant decrease in 5' ETS levels by at least 2-fold as compared to 5' ETS levels isolated from cultures of AML blast cells from patient 5 treated with the vehicle control (p<0.001). In contrast, no different (MNC-1, MNC-2 and MNC-3) or only a modestly decrease (less than 20%; MNC-4 and MNC-5, p<0.01) was observed in 5' ETS levels from MNC cultures treated with OST-01 as compared to MNC cultures treated with vehicle control (see FIG. 13B). Taken together, the results from the rRNA synthesis assays demonstrated that treatment with OST-01 significantly decreases rRNA synthesis in AML blast cells. In addition, the results that OST-01 treatments are effective against AML blast cells but not MNCs revels the specificity of OST-01 activity on targeting leukemic cells without affect normal cells.

Figures 13C, 13D:
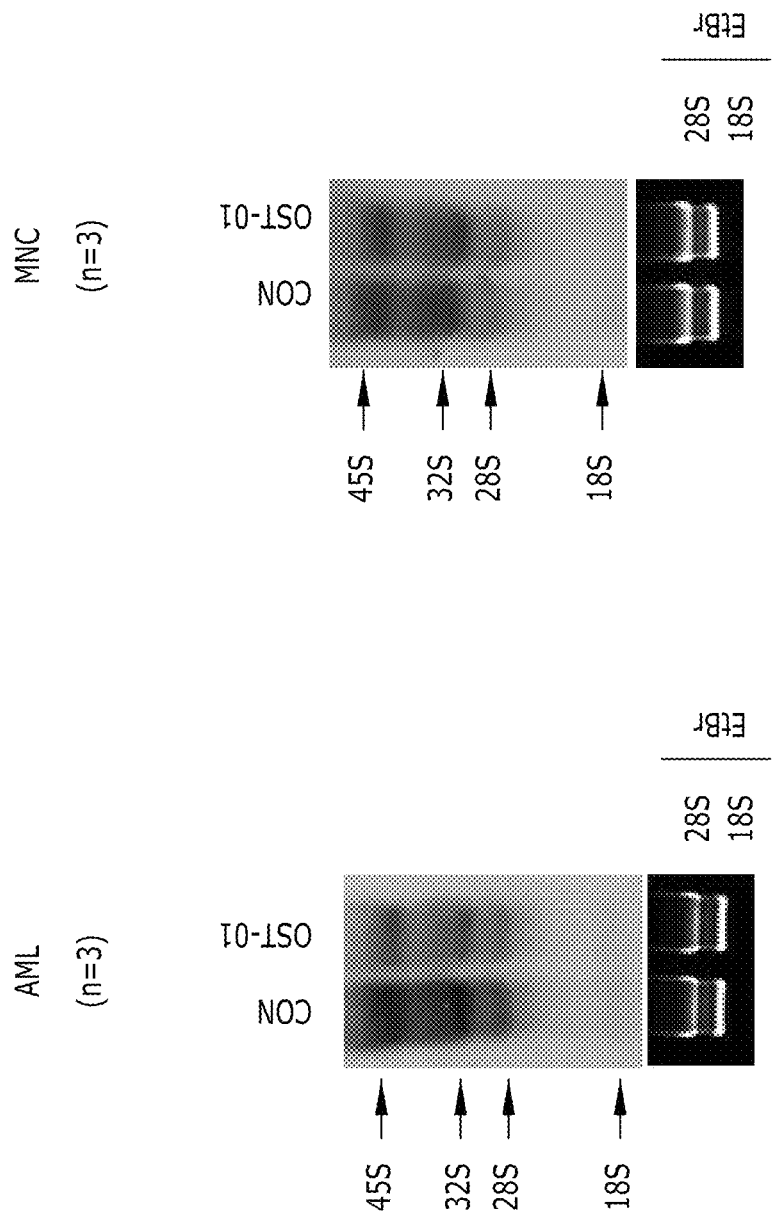

As shown in FIGS. 13C-13D, [$^{32}$P]-labeled RNA levels of total RNA were significantly lower in AML blast cells treated with OST-01 as compared to [$^{32}$P]-labeled RNA levels of total RNA in AML blast cells treated with vehicle control, indicating that rRNA synthesis levels was significantly inhibited in AML blast cells treated with OST-01 compared to untreated controls. For example, as shown in FIG. 13C, cultures of AML blast cells treated with OST-01 exhibited a significant decrease in levels of [$^{32}$P]-labeled RNA by about a 2-fold as compared to [$^{32}$P]-labeled RNA levels isolated from cultures of AML blast cells treated with the vehicle control. In contrast, no different was observed in [$^{32}$P]-labeled RNA levels from MNC cultures treated with OST-01 as compared to MNC cultures treated with vehicle control (see FIG. 13D). Taken together, the results from the rRNA synthesis assays demonstrated that treatment with OST-01 significantly decreases rRNA synthesis in AML blast cells. In addition, the results that OST-01 treatments are effective against AML blast cells but not MNCs revels the specificity of OST-01 activity on targeting leukemic cells without affect normal cells. These results are consistent with and confirm the findings from the 5' ETS q-PCR assay and further demonstrate that the anti-oncogenic activity of OST-01 includes inhibiting of rRNA synthesis and selective targeting of non-solid cancer cells.

In another series of experiments, OST-01 was tested for inhibitory activity on cell proliferation in isolated MNC and AML cells. WTS-1 cell proliferation assays were performed essentially as described in Example 2 except that separate cultures of MNCs isolated from five different patients and AML blast cells isolated from four different patients were analyzed.

Figures 13E, 13F:
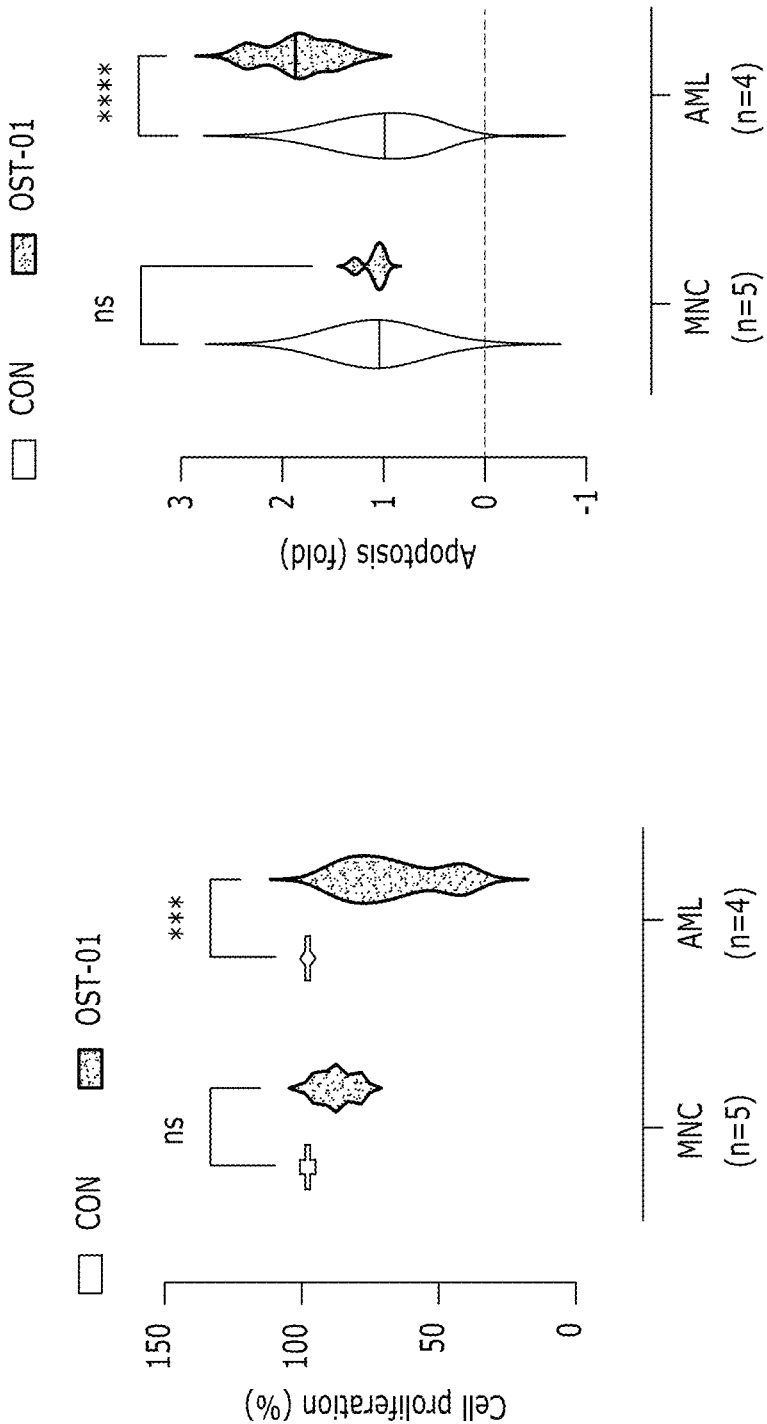

As shown in Table 2 and FIG. 13E, results from the WST-1 proliferation assay demonstrated that treatment with OST-01 significantly inhibited proliferation in primary AML blasts but not normal MNC. For example, while all MNC showed minimal cell proliferation effects when treated with OST-01 at all concentrations tested, AML blasts exhibited a dose-dependent inhibition of cell proliferation relative to treated MNC. As clearly seen in FIG. 13E, the inhibition of cell proliferation in AML blasts relative to MNC was statistically significant. Taken together, the results from the WTS-1 proliferation assay demonstrated that treatment with OST-01 significantly reduces cellular proliferation in all AML cancer cell lines tested, but had minimal effects on all MNCs tested, further demonstrating the anti-oncogenic activity of OST-01 in leukemic cells.

TABLE 2

OST-01 Inhibition of Cell Proliferation in MNC and AML Cell Lines

| Treatment | Percent Cell Survival[1] | | | | | | | | |
|---|---|---|---|---|---|---|---|---|---|
| | MNC-1 | MNC-2 | MNC-3 | MNC-4 | MNC-5 | AML-1 | AML-2 | AML-3 | AML-4 |
| Untreated | 100% | 100% | 100% | 100% | 100% | 100% | 100% | 100% | 100% |
| 0.25 µL/mL OST-01 | 91% | 101% | 102% | 103% | 96% | 100% | 97% | 96% | 100% |
| 0.5 µL/mL OST-01 | 91% | 105% | 102% | 101% | 96% | 100% | 96% | 94% | 91% |
| 1.0 µL/mL OST-01 | 87% | 97% | 94% | 98% | 98% | 99% | 72% | 76% | 88% |
| 2.0 µL/mL OST-01 | 87% | 91% | 81% | 96% | 97 | 76% | 42% | 64% | 86% |
| 4.0 µL/mL OST-01 | 78% | 90% | 71% | 90% | 96% | 64% | 36% | 50% | 82% |

[1]The number of cell from the ethanol control was taken as 100% cell proliferation and that of OST-01 treated groups was calculated as percentage of ethanol control.

To confirm the results of the cell proliferation assay experiments, apoptosis flow cytometry assays, genomic DNA fragmentation assays, and immunoblotting analysis of PARP cleavage and PCNA expression were conducted. Apoptosis flow cytometry assays, genomic DNA fragmentation assays, and immunoblotting analysis were performed essentially as described in Example 3 except that separate cultures of MNCs isolated from five different patients and AML blast cells isolated from four different patients were analyzed.

Figures 13G, 13H:
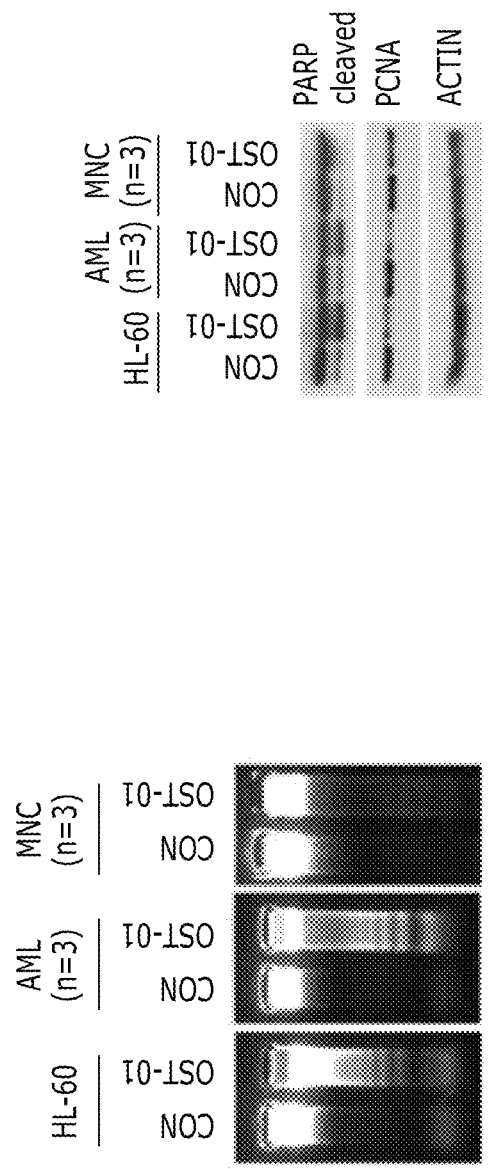
FIG. 13G showing a representative gel staining comparing genomic DNA fragmentation levels occurring in cells from a HL-60 AML cell line and AML blast cells treated with either OST-01 or a vehicle control with genomic DNA fragmentation levels occurring in MNCs treated with either OST-01 or a vehicle control.
FIG. 13H shows a representative blot staining obtained from immunoblotting analyses comparing apoptosis biomarkers in cells from a HL-60 AML cell line and AML blast cells treated with either OST-01 or a vehicle control with apoptosis biomarkers in MNCs treated with either OST-01 or a vehicle control.

As shown in FIGS. 13F, results from the apoptosis flow cytometry assay demonstrated that treatment with OST-01 exhibited in a statistically significant increase (p<0.0001) in Annexin V positive cells as compared to the control in all AML blast cells tested but no increase in Annexin V positive cells was observed in all MNCs tested when compared to the control. Additionally, as shown in FIG. 13G, results from the genomic DNA fragmentation assay demonstrated that treatment with OST-01 showed in a high degree of DNA fragmentation as compared to the control in all AML blast cells tested but no DNA fragmentation was observed in all MNC lines tested when compared to the control. Lastly, as shown in FIG. 13H, results from the immunoblotting analysis demonstrated that treatment with OST-01 showed a dramatically increase in the presence of cleaved PARP and a significant decrease in PCNA levels as compared to the control in all AML blast cells tested but no change in these biomarkers for apoptosis was observed in all MNC lines tested when compared to the control. Taken together, the results from the apoptosis flow cytometry assay, genomic DNA fragmentation assays, and immunoblotting analysis demonstrated that treatment with OST-01 significantly increased the number of cells undergoing apoptosis in all AML blast cells tested but had minimal effects on all MNCs tested, further demonstrating the anti-oncogenic activity of OST-01 in leukemic cells. These results are consistent with and confirm the results from the WST-1 cell proliferation assays and further demonstrate that the anti-oncogenic activity of OST-01 extends to the induction of programed cell death and apoptosis in non-solid cancer cells.

Taken together, the results demonstrated that treatment with OST-01 significantly inhibits rRNA synthesis in AML cells, demonstrating that the anti-oncogenic activity of OST-01 extends to the disruption of rRNA synthesis production in non-solid cancer cells. In addition, these results indicate that OST-01 activity appears to be specific in targeting leukemic cells without affect normal cells.

Example 8

OST-01 Changes of Gene Expression Profiles in Leukemic Cells

To investigate the effects of OST-01 on gene expression in leukemic cells, RNA sequencing was performed and analysis was conducted using Gene Set Enrichment Analysis (GSEA) to determine whether OST-01 activity could alter RNA expression profiles in leukemia cells.

In one series of experiments, cultures of HL-60 leukemic cells were established in 10 cm culture dishes and grown to an approximate density of $10 \times 10^6$ cells. Either 1 µL/mL of OST-01 or 1 µL/mL control vehicle was then added to a culture and incubated for 24 hours at 37° C. in 5% $CO_2$ incubator. After treatment, total RNA was isolated from these cells using a phenol-chloroform RNA purification method following protocols provided by the manufacture (RNeasy Mini Kit, Qiagen, CA) and the extracted RNA was treated with DNase to remove DNA. RNA purity and integrity was evaluated by capillary electrophoresis on the Bioanalyzer Systems (Agilent Technologies, Santa Clara, CA). Isolated RNA was used for either quantitative RT-PCR or RNA-seq.

GSEA was conducted by constructing RNA-seq data Sequencing libraries using the KAPA RNA HyperPrep Kit with RiboErase (HMR) (Roche, KK8560), loaded on to a cBot system for cluster generation, and sequenced on a Hiseq 2500 System (Illumina) with paired-end for mRNA-seq. Raw RNA-seq sequences were subjected to adapter trimming using Trimmomatic v0.38 and poly(A) tails were removed using FASTP v0.19.4. The trimmed reads were aligned to mouse transcriptome, GRCm39, or human transcriptome, GRCh38.p14, using Bowtie2 v2.5.0 with default settings. Expression level of each gene and their isoforms were counted using RSEM (RNA-Seq by Expectation-Maximization, v1.3.3) (Li B, et al. BMC Bioinformatics. 2011. PMID: 21816040). To determine differentially expressed genes (DEGs), EdgeR (v3.20.9) and DESeq2 (v1.38.3) were used with the cutoff of FDR <0.05 and Log 2 fold change ≥1. Robust DEGs were determined with their statistical significance evaluated by both EdgeR and DESeq2. GSEA v4.1.0 (Subramanian A et al, PNAS USA, 2005, PMID:16199517) was performed to identify the affected GO, hallmark and KEGG pathways from MSigDB. Based on Robust DEGs, high potential protein interaction networks were estimated using STRING database (v11.5), and then the networks were visualized by Cytoscape (v3.9.1). R statistical environment (R-4.2.1) was used at all stages of downstream data analysis. Normalized enrichment score representing genes with positive values in that gene set are up-regulated and gene with negative values in that gene set are down-regulated.

As shown in Table 3, results from the GSEA demonstrated that treatment with OST-01 showed induced significant upregulation of the P53, Hedgehog, and mTORC signaling pathways, hypoxia and epithelial mesenchymal transition, as well as angiogenesis and significant downregulation of the c-myc and FAO/OXPHOS signaling pathways and E2F target expression in cells analyzed from the HL-60 leukemic cell line.

TABLE 3

GSEA of HL-60 Leukemic Cells

| Hallmark Gene Set | Up-Regulated | Down-Regulated | Adjusted P Value |
|---|---|---|---|
| Cholesterol Homeostatsis | 2.42 | | 0.00 |
| Estrogen Response (Early) | 2.10 | | 0.00 |
| Hypoxia | 2.08 | | 0.00 |
| Hedgehog Signaling | 1.89 | | 0.00 |
| mTORC1 Signaling | 1.89 | | 0.00 |
| UV Response (Down) | 1.89 | | 0.00 |
| Epithelial Mesenchymal Transition | 1.86 | | 0.00 |
| Angiogenesis | 1.84 | | 0.00 |
| Apical Junction | 1.81 | | 0.00 |
| IP2 STAT5 Signaling | 1.78 | | 0.00 |
| Spermatogenesis | | −1.07 | 0.32 |
| G2M Checkpoint | | −1.08 | 0.35 |
| UV Response (Up) | | −1.20 | 0.16 |
| E2F Targets | | −1.20 | 0.18 |
| Heme Metabolism | | −1.42 | 0.03 |
| Oxidative Phosphorylation | | −1.49 | 0.02 |
| Reactive Oxygen Species Pathway | | −1.59 | 0.01 |
| DNA Repair | | −1.83 | 0.00 |
| MYC Targets (v2) | | −2.00 | 0.00 |
| MYC Targets (v1) | | −2.24 | 0.00 |

In one series of experiments, cultures of AML blast cells isolated from a patient were established in 10 cm culture dishes and grown to an approximate density of $10\times10^6$ cells. Total RNA isolation and quantitative RT-PCR and RNA-seq analyses were performed as described above.

As shown in Table 4, results from the GSEA demonstrated that treatment with OST-01 showed induced significant upregulation of the P53, TNFα, TGFβ, and interferon signaling pathways as well as apoptosis, inflammation and angiogenesis and significant downregulation of the mTORC, c-myc, and cell division, FAO/OXPHOS signaling pathways as well as glycolysis in cells analyzed from AML blast cells.

TABLE 4

GSEA of AML Blast Cells

| Hallmark Gene Set | Up-Regulated | Down-Regulated | Adjusted P Value |
|---|---|---|---|
| P53 Pathway | 2.30 | | 0.00 |
| TNFα Signaling via NFκB | 1.76 | | 0.00 |
| TGFβ Signaling | 1.69 | | 0.00 |
| Apoptosis | 1.47 | | 0.04 |
| Myogenesis | 1.47 | | 0.04 |
| Inflammatory Response | 1.45 | | 0.04 |
| IL6 JAK STAT3 Signaling | 1.31 | | 0.12 |
| INFγ Signaling | 1.24 | | 0.20 |
| Heme Metabolism | 1.23 | | 0.19 |
| kRAS Signaling (Up) | 1.22 | | 0.19 |
| Androgen Response | | −1.63 | 0.00 |
| Estrogen Response (Late) | | −1.71 | 0.00 |
| Unfolded Protein Response | | −1.73 | 0.00 |
| Cholesterol Homeostasis | | −1.77 | 0.00 |
| Glycolysis | | −1.79 | 0.00 |
| mTORC1 Signaling | | −1.80 | 0.00 |
| MYC Targets (v2) | | −2.15 | 0.00 |
| MYC Targets (v1) | | −2.35 | 0.00 |
| G2M Checkpoint | | −2.43 | 0.00 |
| E2F Targets | | −2.54 | 0.00 |

Example 9

OST-01 is Nontoxic in Animals

To investigate the safety for OST-01, an escalating dosing regimen of OST-01 was administered to mice to determine whether OST-01 administration resulting in any toxic or adverse health effects in the animals.

In one series of experiments, twelve 6-8-week-old female CD45.2 B6 were divided into four groups of three animals each. Animals were administered OST-01 by oral gavage, twice a day, for 7 days as follows: Group 1 animals received a 0.1 µL/g/day dose of OST-01; Group 1 animals received a 0.5 µL/g/day dose of OST-01; Group 3 animals received a 1 µL/g/day dose of OST-01; and Group 4 animals received a 2 µL/g/day dose of OST-01. Animals were housed throughout the experiments in micro-insulator cages in a pathogen-free condition and handled in laminar flow hoods. Animals were monitored for weight and behavior one day pre-treatment and each day of treatment. In addition, upon completion of the 7-day treatment period blood samples were taken from all animals in each group and a complete blood count analysis was performed on each sample.

No statistically relevant changes in weight were observed for all animals in each of the four Groups and none of the OST-01 treated animals displayed abnormal behavior during the course of the experiments. Analysis of blood samples demonstrated that all blood parameters values fell within the range considered normal indicating that OST-01 does not cause cytotoxicity for mice in doses up to and including 2 µL/g.

Example 10

OST-01 Suppresses Engraftment and Leukemia Burden in Leukemic Animal Model

To investigate the effects of OST-01 in leukemogenesis, AML transplanted mouse models were used to determine whether OST-01 administration was effective in treating this cancer.

Figure 14A:
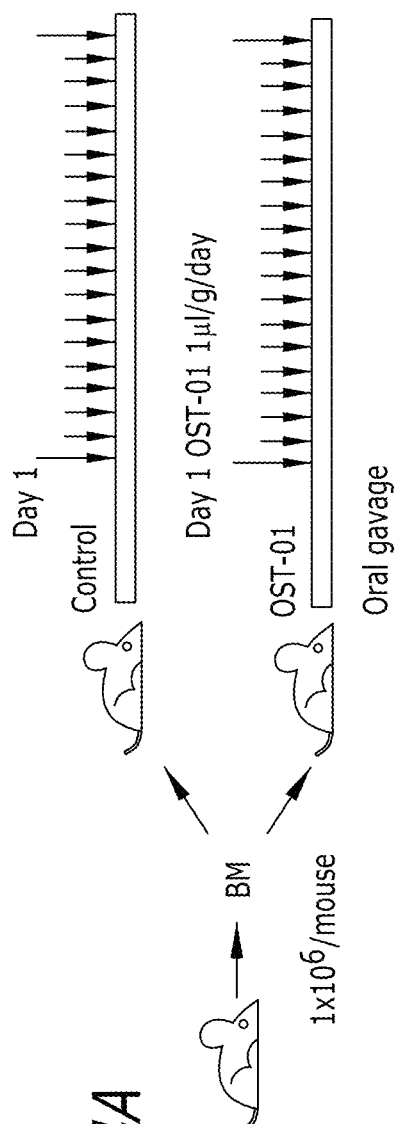
FIGS. 14A-14G show results obtained from a leukemic mouse model with FIG. 14A showing a diagram of the study design.

In one series of experiments, a leukemic mouse model was generated by intravenously transplanting by a right retro orbital injection $1\times10^6$ bone marrow mononuclear cells from acute myeloid leukemia (AML) mice ($MII^{TDMT}/Flt3^{ITD/ITD}$, CD45.2 B6) into 6-8-week-old CD45.1 B6 mice previously irradiated with 400 cGy using a X-ray irradiator. The transplanted mice were then randomly divided into two groups. Treatment commenced on Day 5 after cancer cell transplant with Group 1 animals being administered by oral gavage a single dose of 1 µL/g/day of OST-01 for 14 consecutive days and Group 2 animals being administered by oral gavage a single dose of 1 µL/g/day of vehicle control for 14 consecutive days (see FIG. 14A). Animals were housed throughout the experiments in micro-insulator cages in a pathogen-free condition and handled in laminar flow hoods. To examine effects of OST-01 on leukemogenesis, animals were monitored for survival during the entire course of the experiments. In addition, upon completion of the 14-day treatment period blood samples were taken from all animals in each group and a complete blood count analysis was performed on each sample. Animals were then euthanized and spleen size determined. Mean white blood cell counts from the two groups were compared using unpaired, two-tailed Student's t test, with values from at least two independent experiments with triplicate determination. Data are presented as mean±standard error (SE), as indicated. $p<0.05$ was considered statistically significant. The log-rank Kaplan-Meier survival test was used to compare the survival distributions of the two groups, from time of cancer cell transplant to death of the animals. p<0.05 was considered statistically significant.

Figure 14C:
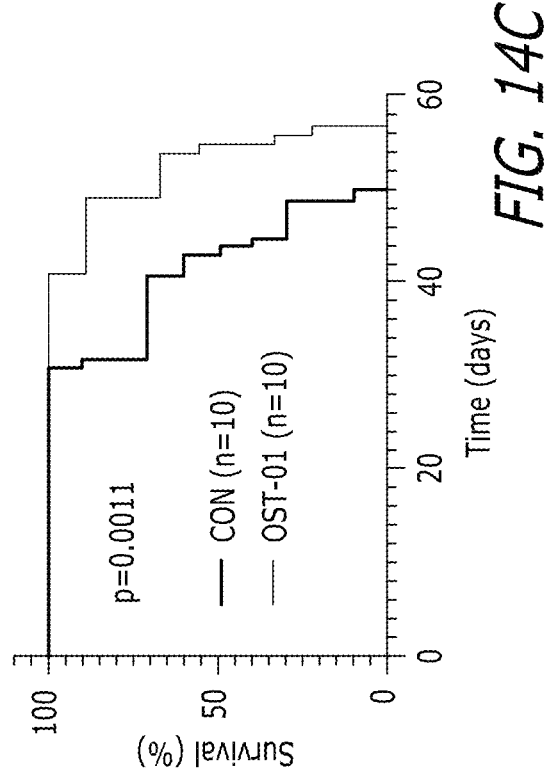
Figure 14B:
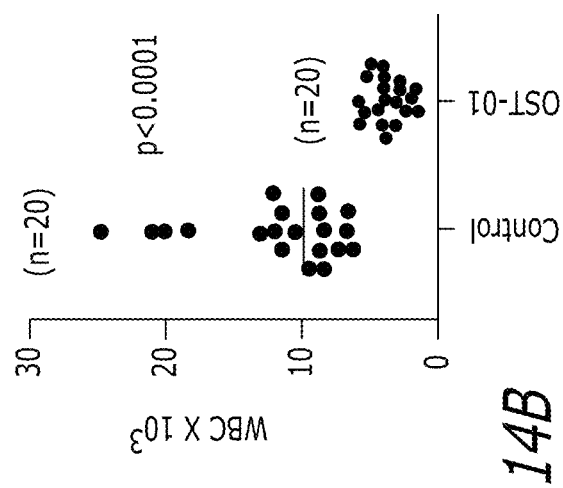
Figure 14D:
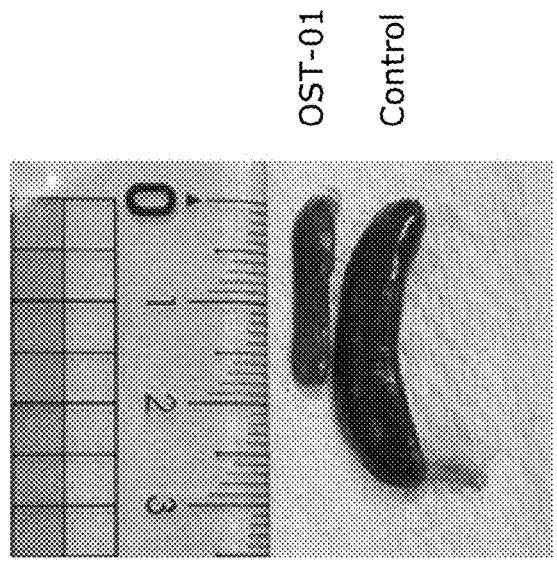
Figure 14E:
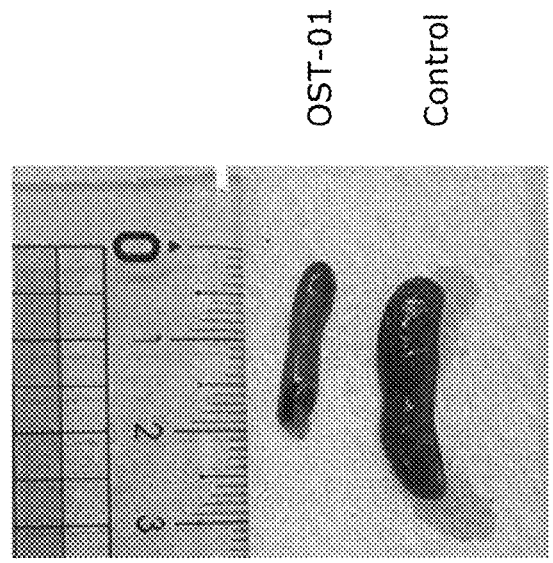

As shown in FIG. 14B, mice transplanted with leukemic cells when treated with OST-01 (n=20) exhibited an almost 50% reduction in white blood cell count when compared to animals treated with the vehicle control. This reduction statistically significant (p=0.00001) and indicates that OST-01 treatment significantly prevented engraftment of leukemic cells in these animals. In addition, as shown in FIG. 14C, mice transplanted with leukemic cells when treated with OST-01 (n=10) had a mean survival time of 55 days relative to a mean survival time of 43.5 days for animals treated with the vehicle control, and represents a statistically significant increase in mouse survival (p=0.0011). In addition, spleen size in animals treated with OST-01 were dramatically reduced being at least half the size of animals treated with the vehicle control (see FIGS. 14D & 14E). Taken together, OST-01 treatment significantly inhibited the onset of leukemia in these animals and demonstrated that OST-01 has remarkable anti-leukemogenic activity in vivo.

In another series of experiments, a leukemic mouse model was generated by intravenously transplanting by a right retro orbital injection $0.5 \times 10^6$ Luc-Molm-13 leukemic cells into 6-8-week-old NOD/SCID/γ chain$^{null}$ mice (NOD scid gamma mouse (NSG), Jackson Laboratory, MA). The transplanted mice were then randomly divided into two groups. Treatment commenced on Day 5 after cancer cell transplant with Group 1 animals (n=10) being administered by oral gavage a single dose of 1 μL/g/day of OST-01 for 32 consecutive days and Group 2 animals (n=10) being administered by oral gavage a single dose of 1 μL/g/day of vehicle control for 32 consecutive days. Animals were housed throughout the experiments in micro-insulator cages in a pathogen-free condition and handled in laminar flow hoods. To examine effects of OST-01 on leukemogenesis, animals were monitored for survival during the entire course of the experiments. In addition, leukemia growth was determined at 14, 19, 24, 29 and 32 days after the start of treatment using bioluminescence imaging (*p<0.01). N=10 mice per group. Mean white blood cell counts from the two groups were compared using unpaired, two-tailed Student's t test, with values from at least two independent experiments with triplicate determination. Data are presented as mean±standard error (SE), as indicated. p<0.05 was considered statistically significant. The log-rank Kaplan-Meier survival test was used to compare the survival distributions of the two groups, from time of cancer cell transplant to death of the animals. p<0.05 was considered statistically significant.

Figure 14G:
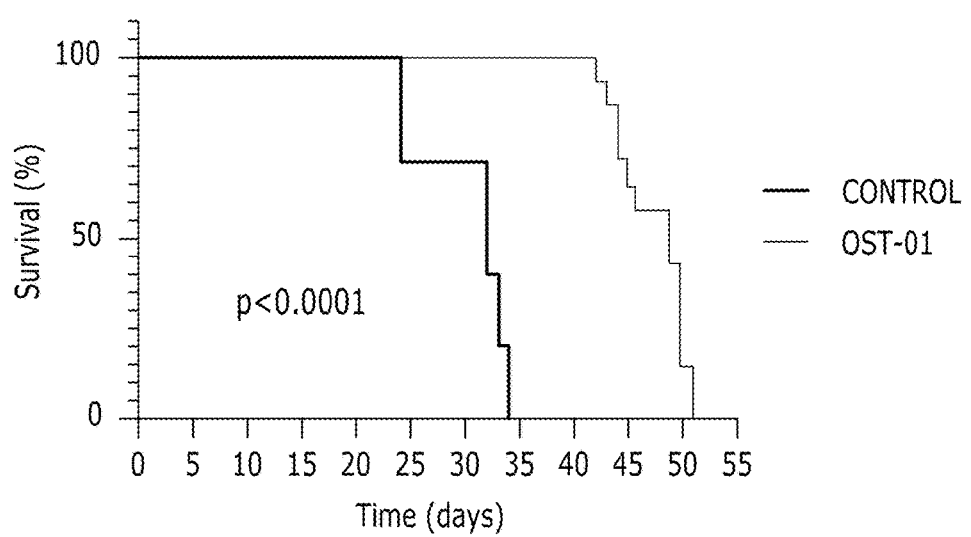
Figure 14F:
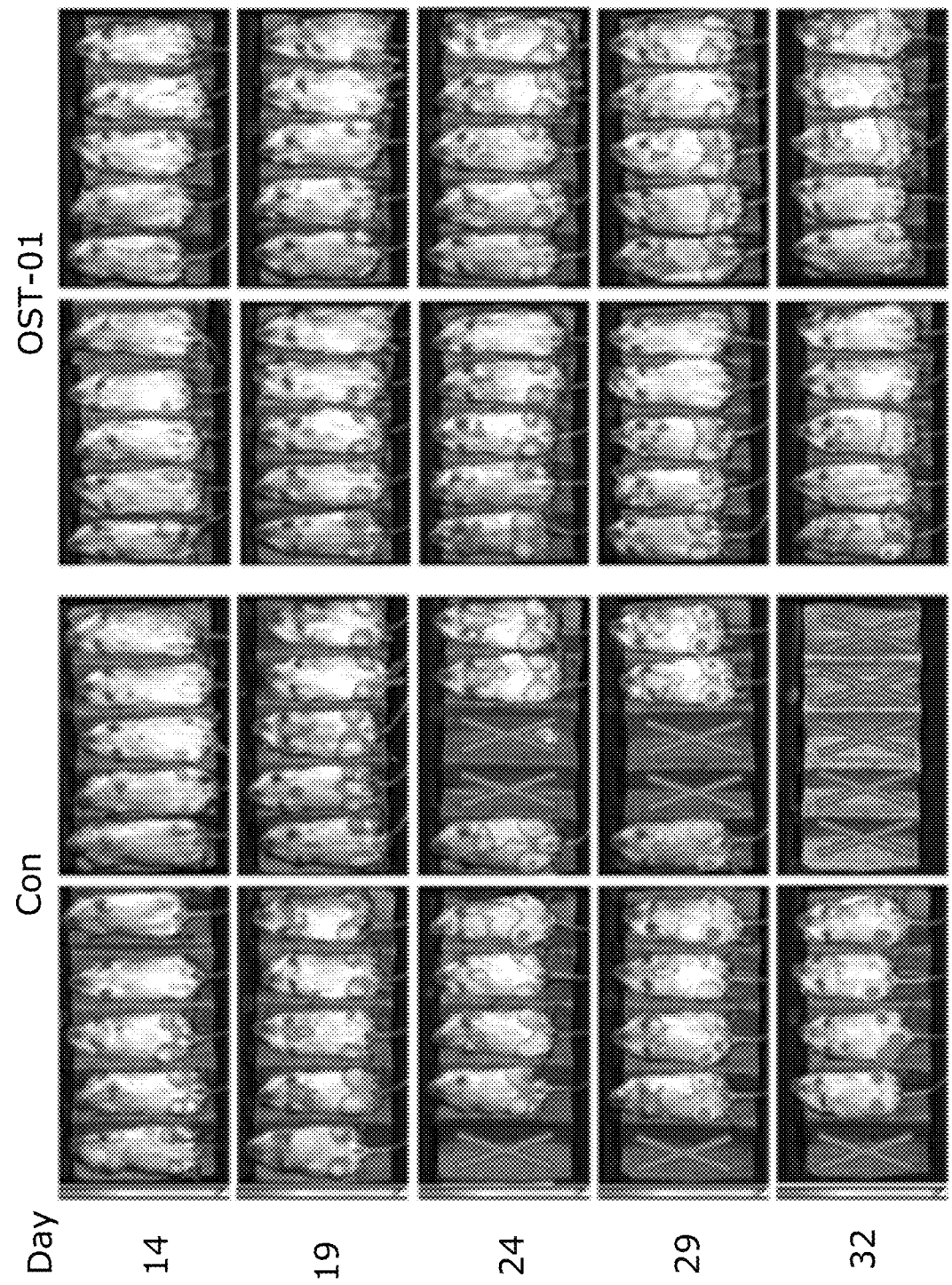

As shown in FIGS. 14F-14G, mice transplanted with Luc-Molm-13 leukemic cells when treated with OST-01 (n=10) exhibited significant reduction in tumor size when compared to animals treated with the vehicle control. For example, as shown in FIG. 14F, mice transplanted with Luc-Molm-13 leukemic cells exhibited a significant reduction in tumor size as shown by a dramatically reduced bioluminescence signal relative to the control group which showed a much stronger signal, indicating that OST treatment inhibited leukemic cell growth in vivo. This reduction in tumor size correlated with increased survival in OST-01 treated animals, For example, as shown in FIG. 14G, mice transplanted with Luc-Molm-13 leukemic cells when treated with OST-01 had a mean survival time of 46 days relative to a mean survival time of 28 days for animals treated with the vehicle control, and represents a statistically significant increase in mouse survival (p=0.0001). Taken together, OST-01 treatment significantly inhibited the onset of leukemia in these animals and demonstrated that OST-01 has remarkable anti-leukemogenic activity in vivo.

Example 11

OST-01 Suppresses Cell Proliferation of Solid Cancer Cells

To investigate the effects of OST-01 on cell proliferation in solid cancer cells, WTS-1 cell proliferation assays were conducted to determine whether OST-01 activity could suppress cell proliferation of cell from cell lines derived from solid cancers.

A WST-1 cell proliferation assay is a colorimetric assay which determines the number of viable cells in a proliferation or cytotoxicity assay. This assay employs tetrazolium compound (4-[3-(4-iodophenyl)-2-(4-nitrophenyl)-2H-5-tetrazolio]-1,3-benzene disulfonate), designated WST-1, which is bioreduced in the presence of NAD(P)H or NADH produced by dehydrogenase enzymes used in glycolysis by metabolically active cells. The bioreduction of WST-1 produces a dark red formazan dye that is soluble and has an absorbance maximum at 450 nm. Thus, the quantity of formazan dye measured by absorbance at 450 nm is directly proportional to the metabolic activity of the cells and serves as a proxy for the number of living cells present in a culture, and indicator cellular viability including cellular growth and proliferation.

In one series of experiments, cells from a H1650 lung cancer cell line, a A549 lung cancer cell line, or a H146 lung cancer cell line were grown to an appropriate density and approximately $1 \times 10^4$ cells were seeded into wells of 96-well cell culture microplate and incubated for 24 hours at 37° C. in the humidified incubator with 5% $CO_2$. After incubation, growth medium was removed from each well 96 and replaced with fresh growth medium containing a specified concentration of OST-01 or an ethanol control. The treated cells were then incubated for another 24 hours at 37° C. in 5% $CO_2$ incubator. Cell growth was then assessed using a Cell Proliferation Reagent WST-1 (Roche Diagnostics, Germany) following protocols provided by the manufacture. To determine the amount of soluble formazan produced by cellular reduction of WTS-1, the absorbance of each well is measured at 450 nm using a multimode microplate reader (Molecular Devices, USA). Cell proliferation of the ethanol control was taken as 100% and that of OST-01 treated groups were calculated as percentage of ethanol control.

As shown in Table 5, results from the WST-1 proliferation assay demonstrated that treatment with OST-01 showed a dose-dependent inhibition of cell proliferation as compared to the ethanol control in all lung cancer cell lines tested. For example, A549 cells treated with OST-01 exhibited a dose-dependent inhibition of cell proliferation relative to cells treated with the ethanol control, and reached at least a 75% inhibition of cell proliferation at the highest concentration tested (2.0 μL/mL OST-01). Similarly, H146 cells treated with OST-01 exhibited a dose-dependent inhibition of cell proliferation relative to cells treated with the ethanol control, and reached over 70% inhibition of cell proliferation at the highest concentration tested (2.0 μL/mL OST-01). Likewise, H1650 cells treated with OST-01 exhibited a dose-dependent inhibition of cell proliferation relative to cells treated with the ethanol control, and reached about 60% inhibition of cell proliferation at the highest concentration tested (2.0

µL/mL OST-01). Taken together, the results from the WTS-1 proliferation assay demonstrated that treatment with OST-01 significantly reduces cellular proliferation in all lung cancer cell lines tested, further demonstrating the anti-oncogenic activity of OST-01 in lung cancer cells.

TABLE 5

OST-01 Inhibition of Cell Proliferation in Lung Cancer Cell Lines

| Treatment | Percent Cell Survival[1] | | |
|---|---|---|---|
| | H1650 | A549 | H146 |
| Untreated | 100% | 100% | 100% |
| 0.01 µL/mL OST-01 | 56% | 48% | 37% |
| 0.05 µL/mL OST-01 | 54% | 48% | 37 |
| 0.1 µL/mL OST-01 | 51% | 45% | 32% |
| 0.25 µL/mL OST-01 | 47% | 43% | 32% |
| 0.5 µL/mL OST-01 | 47% | 35% | 31% |
| 1.0 µL/mL OST-01 | 46% | 29% | 28% |
| 2.0 µL/mL OST-01 | 41% | 25% | 27% |

[1] The number of cell from the ethanol control was taken as 100% cell proliferation and that of OST-01 treated groups was calculated as percentage of ethanol control.

In another series of experiments, OST-01 was tested for inhibitory activity on cell proliferation in cells from the five triple negative breast cancer cell lines MDA-MB-468, MDA-MB-231, 4T1, BT549, and BT474. WTS-1 cell proliferation assays were performed essentially as described above for the lung cancer cell lines.

As shown in Table 6, results from the cell proliferation assay demonstrated that treatment with OST-01 showed a dose-dependent inhibition of cell proliferation as compared to the ethanol control in all breast cancer cell lines tested. For example, MDA-MB-231. 4T1, and BT549 cells treated with OST-01 exhibited a dose-dependent inhibition of cell proliferation relative to cells treated with the ethanol control, and reached at least 91% inhibition of cell proliferation at the highest concentration tested (2.0 µL/mL OST-01). Similarly, MDA-MB-468 cells treated with OST-01 exhibited a dose-dependent inhibition of cell proliferation based on cell count relative to cells treated with the ethanol control, and reached at least 78% inhibition of cell proliferation at the highest concentration tested (2.0 µL/mL OST-01). Lastly, BT474 cells treated with OST-01 exhibited a dose-dependent inhibition of cell proliferation based on cell count relative to cells treated with the ethanol control, and reached at least 16% inhibition of cell proliferation at the highest concentration tested (2.0 µL/mL OST-01). Taken together, the results from the WTS-1 proliferation assay demonstrated that treatment with OST-01 significantly reduces cellular proliferation in all breast cancer cell lines tested, further demonstrating the anti-oncogenic activity of OST-01 in breast cancer cells.

TABLE 6

OST-01 Inhibition of Cell Proliferation In Breast Cancer Cell Lines

| Treatment | Percent Cell Survival[1] | | | | |
|---|---|---|---|---|---|
| | MDA-MB-468 | MDA-MB-231 | 4T1 | BT549 | BT474 |
| Untreated | 100% | 100% | 100% | 100% | 100% |
| 0.01 µL/mL OST-01 | 36% | 43% | 37% | 41% | 100% |
| 0.05 µL/mL OST-01 | 35% | 39% | 22% | 40% | 98% |
| 0.1 µL/mL OST-01 | 31% | 32% | 17% | 39% | 98% |
| 0.25 µL/mL OST-01 | 28% | 20% | 6% | 30% | 97% |
| 0.5 µL/mL OST-01 | 27% | 20% | 5% | 21% | 96% |
| 1.0 µL/mL OST-01 | 24% | 14% | 5% | 13% | 94% |
| 2.0 µL/mL OST-01 | 22% | 9% | 3% | 7% | 84% |

[1] The number of cell from the ethanol control was taken as 100% cell proliferation and that of OST-01 treated groups was calculated as percentage of ethanol control.

In another series of experiments, was tested for inhibitory activity on cell proliferation in cells from the colon cancer cell lines LoVo, HCT116, HT29, SW480 and SW620. WST-1 cell proliferation assays were performed essentially as described above for the lung cancer cell lines.

As shown in Table 7, results from the cell proliferation assay demonstrated that treatment with OST-01 showed a dose-dependent inhibition of cell proliferation as compared to the ethanol control in all colon cancer cell lines tested. For example, SW480 and cells treated with OST-01 exhibited a dose-dependent inhibition of cell proliferation relative to cells treated with the ethanol control, and reached about 90% inhibition of cell proliferation at the highest concentration tested (2.0 µL/mL OST-01). Similarly, LoVo and HCT116 cells treated with OST-01 exhibited a dose-dependent inhibition of cell proliferation relative to cells treated with the ethanol control, and reached at least 83% inhibition of cell proliferation at the highest concentration tested (2.0 µL/mL OST-01). Likewise, HT29 cells treated with OST-01 exhibited a dose-dependent inhibition of cell proliferation relative to cells treated with the ethanol control, and reached at least 77% inhibition of cell proliferation at the highest concentration tested (2.0 µL/mL OST-01). Lastly, SW620 cells treated with OST-01 exhibited a dose-dependent inhibition of cell proliferation based on cell count relative to cells treated with the ethanol control, and reached about 67% inhibition of cell proliferation at the highest concentration tested (2.0 µL/mL OST-01). Taken together, the results from the WTS-1 proliferation assay demonstrated that treatment with OST-01 significantly reduces cellular proliferation in all colon cancer cell lines tested, further demonstrating the anti-oncogenic activity of OST-01 in colon cancer cells.

TABLE 7

OST-01 Inhibition of Cell Proliferation in Colon Cancer Cell Lines

| Treatment | Percent Cell Survival[1] | | | | |
|---|---|---|---|---|---|
| | LoVo | HCT116 | HT29 | SW480 | SW620 |
| Untreated | 100% | 100% | 100% | 100% | 100% |
| 0.01 µL/mL OST-01 | 77% | 41% | 60% | 63% | 87% |
| 0.05 µL/mL OST-01 | 76% | 39% | 59% | 60% | 85% |
| 0.1 µL/mL OST-01 | 75% | 36% | 58% | 58% | 78% |
| 0.25 µL/mL OST-01 | 66% | 36% | 57% | 54% | 74% |
| 0.5 µL/mL OST-01 | 49% | 29% | 48% | 44% | 60% |
| 1.0 µL/mL OST-01 | 25% | 20% | 29% | 25% | 41% |
| 2.0 µL/mL OST-01 | 16% | 17% | 23% | 10% | 33% |

[1] The number of cell from the ethanol control was taken as 100% cell proliferation and that of OST-01 treated groups was calculated as percentage of ethanol control.

In another series of experiments, was tested for inhibitory activity on cell proliferation in cells from the ovarian cancer cell lines A2780R and SKOV3. WST-1 cell proliferation assays were performed essentially as described above for the lung cancer cell lines.

As shown in Table 8, results from the cell proliferation assay demonstrated that treatment with OST-01 showed a dose-dependent inhibition of cell proliferation as compared to the ethanol control in all ovarian cancer cell lines tested. For example, A2780R cells treated with OST-01 exhibited a dose-dependent inhibition of cell proliferation relative to cells treated with the ethanol control, and reached about 97% inhibition of cell proliferation at the highest concentration tested (2.0 µL/mL OST-01). Similarly, SKOV3 cells treated with OST-01 exhibited a dose-dependent inhibition of cell proliferation relative to cells treated with the ethanol control, and reached at least 77% inhibition of cell proliferation at the highest concentration tested (2.0 µL/mL OST-01). Taken together, the results from the WTS-1 proliferation assay demonstrated that treatment with OST-01 significantly reduces cellular proliferation in all ovarian cancer cell lines tested, further demonstrating the anti-oncogenic activity of OST-01 in ovarian cancer cells.

TABLE 8

OST-01 Inhibition of Cell Proliferation in Ovarian Cancer Cell Lines

| Treatment | Percent Cell Survival[1] | |
|---|---|---|
| | A2780R | SKOV3 |
| Untreated | 100% | 100% |
| 0.01 µL/mL OST-01 | 29% | 40% |
| 0.05 µL/mL OST-01 | 28% | 40% |
| 0.1 µL/mL OST-01 | 24% | 34% |
| 0.25 µL/mL OST-01 | 8% | 32% |
| 0.5 µL/mL OST-01 | 5% | 28% |
| 1.0 µL/mL OST-01 | 4% | 27% |
| 2.0 µL/mL OST-01 | 3% | 23% |

[1]The number of cell from the ethanol control was taken as 100% cell proliferation and that of OST-01 treated groups was calculated as percentage of ethanol control.

In another series of experiments, was tested for inhibitory activity on cell proliferation in cells from the pancreatic cancer cell lines KPC, MiaPaCa-2 and PANC-1. WST-1 cell proliferation assays were performed essentially as described above for the lung cancer cell lines.

As shown in Table 9, results from the cell proliferation assay demonstrated that treatment with OST-01 showed a dose-dependent inhibition of cell proliferation as compared to the ethanol control in all pancreatic cancer cell lines tested. For example, KPC cells treated with OST-01 exhibited a dose-dependent inhibition of cell proliferation relative to cells treated with the ethanol control, and reached about 85% inhibition of cell proliferation at the highest concentration tested (2.0 µL/mL OST-01). Similarly, MiaPaCa-2 cells treated with OST-01 exhibited a dose-dependent inhibition of cell proliferation relative to cells treated with the ethanol control, and reached at least 82% inhibition of cell proliferation at the highest concentration tested (2.0 µL/mL OST-01). Likewise, PANC-1 cells treated with OST-01 exhibited a dose-dependent inhibition of cell proliferation relative to cells treated with the ethanol control, and reached at least 75% inhibition of cell proliferation at the highest concentration tested (2.0 µL/mL OST-01). Taken together, the results from the WST-1 proliferation assay demonstrated that treatment with OST-01 significantly reduces cellular proliferation in all pancreatic cancer cell lines tested, further demonstrating the anti-oncogenic activity of OST-01 in pancreatic cancer cells.

TABLE 9

OST-01 Inhibition of Cell Proliferation in Pancreatic Cancer Cell Lines

| Treatment | Percent Cell Survival[1] | | |
|---|---|---|---|
| | KPC | MiaPaCa-2 | PANC-1 |
| Untreated | 100% | 100% | 100% |
| 0.01 µL/mL OST-01 | 77% | 33% | 49% |
| 0.05 µL/mL OST-01 | 50% | 26% | 35% |
| 0.1 µL/mL OST-01 | 22% | 23% | 28% |
| 0.25 µL/mL OST-01 | 20% | 23% | 25% |
| 0.5 µL/mL OST-01 | 19% | 22% | 26% |
| 1.0 µL/mL OST-01 | 18% | 21% | 27% |
| 2.0 µL/mL OST-01 | 15% | 18% | 25% |

[1]The number of cell from the ethanol control was taken as 100% cell proliferation and that of OST-01 treated groups was calculated as percentage of ethanol control.

Example 12

OST-01 Induces Apoptosis and Oxidative Stress in Solid Cancer Cells

To investigate the effects of OST-01 on cell proliferation in solid cancer cells, apoptosis flow cytometry assays and superoxide activity assays were conducted to determine whether OST-01 activity could increase apoptosis and oxidative stress of solid cancer cells.

Five different solid cancer cell lines were selected for these studies: a 293T kidney cancer cells (RRID: CVCL_0063), a MCF-7 breast cancer cells (RRID: CVCL_0031), a A549 lung cancer cells (RRID: CVCL_0023), a HCT-116 colon cancer cells (RRID: CVCL_0291), and a PC3 prostate cancer cells (RRID: CVCL_0035). All five cell lines were obtained from the ATCC. 293T cells are embryonic kidney cells of epithelial origin isolated from a human female fetus. MCF-7 cells are epithelial cells from mammary gland tissue that were isolated from a 69-year-old human adult female diagnosed with metastatic adenocarcinoma. A549 cells are epithelial cells from lung that were isolated from a 58-year-old human male diagnosed with carcinoma of the lung. HCT-116 cells are epithelial cells from colon that were isolated from a human adult male diagnosed with colorectal carcinoma. PC3 cells are epithelial cells from prostate that were isolated from a 62-year-old human male diagnosed with prostatic adenocarcinoma. Cell lines were authenticated by cell morphology monitoring, growth curve analysis, and *Mycoplasma* detection using a *Mycoplasma* Detection Kit (Roche Diagnostic, Germany). Cell lines were maintained in Dulbecco's Modified Eagle Medium (DMEM) or Roswell Park Memorial Institute (RPMI) medium supplemented with 10% Fetal bovine serum (FBS) and 100 units of penicillin/streptomycin an incubated at 37° C. in 5% $CO_2$ incubator.

Apoptosis flow cytometry assays were performed essentially as described in Example 3. In one series of experiments, separate cultures of 293T, MCF-7, A549, HCT-116, and PC3 cells were established in 10 cm culture dishes and grown to an approximate density of $10 \times 10^6$ cells. Either 1 µL/mL of OST-01 or 1 µL/mL control vehicle was then added to a culture for each of the three AML cell lines and incubated for 24 hours at 37° C. in 5% $CO_2$ incubator. Cells were then assessed for apoptosis by an apoptosis flow cytometry assay employing with a fluorochrome-conjugated Annexin V and/or the fluorescent nucleic acid dye 4,6-diamidino-2-phenylindole (DAPI) (APC Annexin V, BD Bioscience, CA) following protocols provided by the manufacture. Briefly, after OST-01 treatment, cells were washed twice with an Annexin V buffered solution, resuspended in the same buffer at a concentration of $1\times10^6$ cells/mL, and 100 µL aliquoted transferred to 1 mL culture tubes. Aliquots were then incubated in the dark for 15 minutes with either 1) an Annexin-V-APC conjugate and DAPI, 1) an Annexin-V-APC conjugate; or 3) DAPI. An unstained aliquot was also set up as a negative control to define the basal level of apoptotic and dead cells. The percentage of cells that have been induced to undergo apoptosis is then determined by subtracting the percentage of apoptotic cells in the unstained aliquot from percentage of apoptotic cells in the stained aliquot. After staining, cells were washed in ice-cold PBS and resuspended in 300 µL of the Annexin V buffered solution, and analysis by flow cytometry using an LSR II flow cytometer (BD Bioscience, CA). Cells that were Annexin V negative and DAPI negative are considered healthy, cells, Annexin V positive and DAPI negative cells are considered apoptotic, and cells that are positive to both Annexin V and DAPI considered necrotic. Mean cell numbers between the OST-01 treated and control group was statistically analyzed by using unpaired, two-tailed Student's t test, with values from at least two independent experiments with triplicate determination. Data are presented as mean±standard error (SE) and a $p<0.05$ was considered statistically significant.

Figure 15:
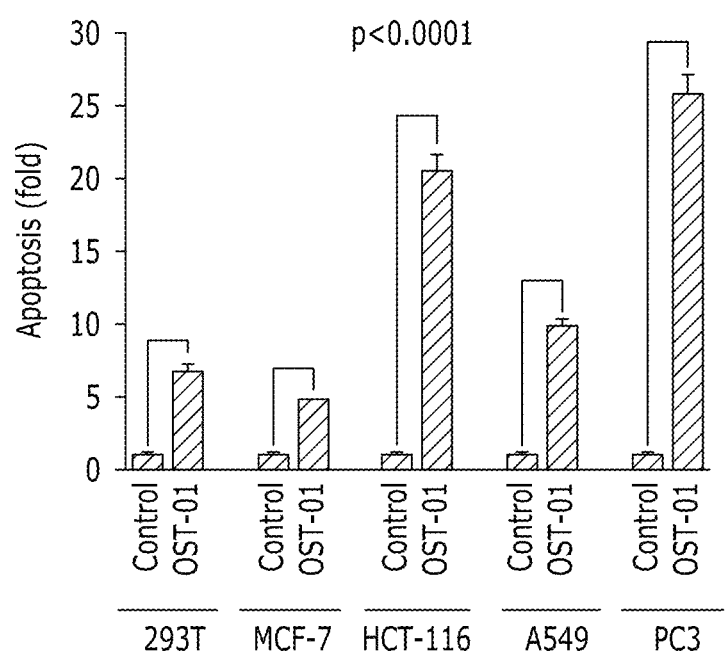
FIG. 15 shows bar graphs of cells stained with Annexin V obtained from apoptosis flow cytometry assays showing cells from five different solid cancer cell lines treated with either OST-01 or a vehicle control.

As shown in FIG. 15, results from the apoptosis flow cytometry assay demonstrated that treatment with OST-01 exhibited in a statistically significant increase in Annexin V positive cells as compared to the control in all solid cancer cell lines tested. For example, 293T cells treated with OST-01 showed at least a 6-fold increase in Annexin V positive cells relative to cells treated with the vehicle control (see FIG. 15, $p<0.0001$), MCF-7 cells treated with OST-01 showed over a 4-fold increase in Annexin V positive cells relative to cells treated with the vehicle control (see FIG. 15, $p<0.0001$), HCT-116 cells treated with OST-01 showed at least a 20-fold increase in Annexin V positive cells relative to cells treated with the vehicle control (see FIG. 15, $p<0.0001$), A549 cells treated with OST-01 showed at least a 10-fold increase in Annexin V positive cells relative to cells treated with the vehicle control (see FIG. 15, $p<0.0001$), and PC3 cells treated with OST-01 showed at least a 25-fold increase in Annexin V positive cells relative to cells treated with the vehicle control (see FIG. 15, $p<0.0001$). Taken together, the results from the apoptosis flow cytometry assay demonstrated that treatment with OST-01 significantly induces apoptosis in five different solid cancer cell lines. These results are consistent with the findings for leukemic cells of Example 3 and further extend these findings to solid cancer cells, demonstrating that the anti-oncogenic activity of OST-01 is effective against both solid and non-solid cancers.

Superoxide activity assays were performed essentially as described in Example 5. In one series of experiments, separate cultures of 293T, MCF-7, A549, HCT-116, and PC3 cells were established in 3 cm culture dishes and grown to an approximate density of $1\times10^6$ cells. Either 1 µL/mL of OST-01 or 1 µL/mL control vehicle was then added to a culture and incubated for 24 hours at 37° C. in 5% $CO_2$ incubator. Cells were then assessed for oxidative stress by a superoxide activity assay employing with a fluorescent indicator MitoSOX™ (MitoSOX™ Red Mitochondrial Superoxide Indicator, Thermo Scientific, CO) following protocols provided by the manufacture. Briefly, after OST-01 treatment, cells were washed twice in ice-cold PBS and incubated in the dark with a MitoSOX™ Red reagent solution for 15 minutes at 18° C. in 5% $CO_2$ incubator. Cells were then washed in warm PBS, resuspended in 300 µL of buffer, and counterstained with the fluorescent nucleic acid dye DAPI to identify nuclei. After staining, cells were washed in warm PBS and analysis by flow cytometry using an LSR II flow cytometer (BD Bioscience, CA). Mean cell numbers between the OST-01 treated and control group was statistically analyzed by using unpaired, two-tailed Student's t test, with values from at least two independent experiments with triplicate determination. Data are presented as mean±standard error (SE) and a $p<0.05$ was considered statistically significant.

As shown in FIG. 16, results from the superoxide activity assay demonstrated that treatment with OST-01 showed a dramatically increase in superoxide activity compared to the control in all solid cancer cell lines tested. For example, 293T cells treated with OST-01 showed at least a 40% increase in Annexin V positive cells relative to cells treated with the vehicle control (see FIG. 16, $p<0.0001$), MCF-7 cells treated with OST-01 showed a 30% increase in Annexin V positive cells relative to cells treated with the vehicle control (see FIG. 16, $p<0.0001$), HCT-116 cells treated with OST-01 showed about a 40% increase in Annexin V positive cells relative to cells treated with the vehicle control (see FIG. 16, $p<0.0001$), A549 cells treated with OST-01 showed at least a 40% increase in Annexin V positive cells relative to cells treated with the vehicle control (see FIG. 16, $p<0.0001$), and PC3 cells treated with OST-01 showed about a 50% increase in Annexin V positive cells relative to cells treated with the vehicle control (see FIG. 16, $p<0.0001$). Taken together, the results from the superoxide activity assay demonstrated that treatment with OST-01 significantly increased ROS induction and, by inference, oxidative stress, in all five solid cancer cell lines tested. These results are consistent with the findings for leukemic cells of Example 5 and further extend these findings to solid cancer cells, demonstrating that the anti-oncogenic activity of OST-01 is effective against both solid and non-solid cancers.

Example 13

OST-01 Suppresses Anoikis Resistance of Solid Cancer Cells

To test whether OST-01 can prevent or reduce anoikis resistance, anoikis resistance assays were performed. An anoikis resistance assay is a colorimetric assay measuring anchorage-independent growth and monitoring anoikis propelled cell death. Adhesion to the extracellular matrix (ECM) is essential for survival and propagation of many adherent cells. Apoptosis that results from the loss of cell adhesion to the ECM, or inappropriate adhesion, is defined as anoikis. A programmed cell death, anoikis is activated when cells are detached from the ECM. Therefore, preventing or reducing the loss of or inappropriate adhesion of cells to the ECM, and thus preventing or reducing anoikis is a crucial mechanism reducing or preventing cells from growing in inappropriate or distant locations.

In one series of experiments, cells from a H1650 lung cancer cell line, a A549 lung cancer cell line, or a H146 lung cancer cell line were grown to an appropriate density and approximately $1\times10^6$ cells were seeded onto poly(2-hydroxyethyl) methacrylate (HEMA)-coated culture plates. HEMA prevents cell adhesion to the substrate and thus creates anchorage-independent growth conditions. Cell-seeded plates were then treated by adding 0.5 µL/mL, 1.0 µL/mL, 2.0 µL/mL, 4.0 µL/mL, 6.0 µL/mL, or 8.0 µL/mL of OST-01 and incubated for 24 hours at 37° C. in the humidified incubator with 5% $CO_2$. Control plates were treated by adding 8 μL/mL ethanol and incubated for 24 hours. The treated cells were then centrifuged and uniformly divided in HEMA-uncoated wells of a 24-well plated and incubated for 8 hours at 37° C. in the humidified incubator with 5% $CO_2$ to allow cells to adhere to the surface of the wells. After incubation, cells were then assays for cell viability using a sulforhodamine B (SRB) staining assay. SRB is a bright pink aminoxanthene dye that binds proteins under mild acidic conditions and can be subsequent extraction under basic conditions. The amount of SRB extracted is a proxy for cell mass and thus measurement of the number of cells in a sample which allows assessment of cell viability, cytotoxicity, and cell proliferation. In the SRB staining assay, incubated cells are fixed onto the surface of the well, stained with SRB, washed and dried, and then the bound SRB is solubilized and the absorbance of the dye in solution is measured at OD 565 nm. Anoikis resistance of the ethanol control was taken as 100% and that of OST-01 treated groups were calculated as percentage of ethanol control.

As shown in Table 10, results from the anoikis resistance assay demonstrated that treatment with OST-01 showed a dose-dependent inhibition of anoikis resistance as compared to the ethanol control in all lung cancer cell lines tested. For example, H1650 cells treated with OST-01 exhibited a dose-dependent inhibition of anoikis resistance based on cell count relative to cells treated with the ethanol control, and reached at least a 30% inhibition of anoikis resistance at the highest concentration tested (8.0 μL/mL OST-01). Similarly, A549 cells treated with OST-01 exhibited a dose-dependent inhibition of anoikis resistance based on cell count relative to cells treated with the ethanol control, and reached about 45% inhibition of anoikis resistance at the highest concentration tested (8.0 μL/mL OST-01). Likewise, H146 cells treated with OST-01 exhibited a dose-dependent inhibition of anoikis resistance based on cell count relative to cells treated with the ethanol control, and reached over 65% inhibition of anoikis resistance at the highest concentration tested (8.0 μL/mL OST-01). Taken together, the results from the anoikis resistance assay demonstrated that treatment with OST-01 significantly inhibited anoikis resistance from all lung cancer cell lines tested, further demonstrating that the anti-oncogenic activity of OST-01 extends to the inhibition of solid cancer metastasis.

TABLE 10

OST-01 Inhibition of Anoikis Resistance in Lung Cancer Cell Lines

| Treatment | Percent Anoikis Resistance[1] | | |
|---|---|---|---|
|  | H1650 | A549 | H146 |
| Untreated | 100% | 100% | 100% |
| 0.5 μL/mL OST-01 | 98% | 100% | 97% |
| 1.0 μL/mL OST-01 | 94% | 91% | 95% |
| 2.0 μL/mL OST-01 | 93% | 71% | 74% |
| 4.0 μL/mL OST-01 | 80% | 62% | 63% |
| 6.0 μL/mL OST-01 | 72% | 58% | 45% |
| 8.0 μL/mL OST-01 | 69% | 57% | 34% |

[1]Anoikis resistance of the ethanol control was taken as 100% and that of OST-01 treated groups was calculated as percentage of ethanol control.

In another series of experiments, OST-01 was tested for inhibitory activity on anoikis resistance in cells from the five triple negative breast cancer cell lines MDA-MB-468, MDA-MB-231, 4T1, BT549, and B1474. Anoikis resistance assays were performed essentially as described above for the lung cancer cell lines, except that 0.01 μL/mL, 0.05 μL/mL, 0.1 μL/mL, 0.25 μL/mL, 0.5 μL/mL, 1.0 μL/mL, 2.0 μL/mL of OST-01 was added to cell-seeded plates.

As shown in Table 11, results from the anoikis resistance assay demonstrated that treatment with OST-01 showed a dose-dependent inhibition of anoikis resistance as compared to the ethanol control in all breast cancer cell lines tested. For example, MDA-MB-468 and MDA-MB-231 cells treated with OST-01 exhibited a dose-dependent inhibition of anoikis resistance based on cell count relative to cells treated with the ethanol control, and reached at least 81% inhibition of anoikis resistance at the highest concentration tested (2.0 μL/mL OST-01). Similarly, 4T1 and BT549 cells treated with OST-01 exhibited a dose-dependent inhibition of anoikis resistance based on cell count relative to cells treated with the ethanol control, and reached at least 77% inhibition of anoikis resistance at the highest concentration tested (2.0 μL/mL OST-01). Lastly, BT474 cells treated with OST-01 exhibited a dose-dependent inhibition of anoikis resistance based on cell count relative to cells treated with the ethanol control, and reached at least 16% inhibition of anoikis resistance at the highest concentration tested (2.0 μL/mL OST-01). Taken together, the results from the anoikis resistance assay demonstrated that treatment with OST-01 significantly inhibited anoikis resistance from all breast cancer cell lines tested, further demonstrating that the anti-oncogenic activity of OST-01 extends to the inhibition of solid cancer metastasis.

TABLE 11

OST-01 Inhibition of Anoikis Resistance in Breast Cancer Cell Lines

| Treatment | Percent Anolkis Resistance[1] | | | | |
|---|---|---|---|---|---|
|  | MDA-MB-468 | MDA-MB-231 | 4T1 | BT549 | BT474 |
| Untreated | 100% | 100% | 100% | 100% | 100% |
| 0.01 μL/mL OST-01 | 92% | 97% | 92% | 94% | 98% |
| 0.05 μL/mL OST-01 | 55% | 67% | 73% | 82% | 97% |
| 0.1 μL/mL OST-01 | 34% | 48% | 41% | 70% | 97% |
| 0.25 μL/mL OST-01 | 27% | 31% | 33% | 62% | 96% |
| 0.5 μL/mL OST-01 | 23% | 28% | 27% | 57% | 93% |
| 1.0 μL/mL OST-01 | 17% | 23% | 24% | 43% | 90% |
| 2.0 μL/mL OST-01 | 17% | 19% | 22% | 23% | 84% |

[1]Anoikis resistance of the ethanol control was taken as 100% and that of OST-01 treated groups was calculated as percentage of ethanol control.

In another series of experiments, was tested for inhibitory activity on anoikis resistance in cells from the colon cancer cell lines LoVo, HCT116, HT29, SW480 and SW620. Anoikis resistance assays were performed essentially as described above for the lung cancer cell lines.

As shown in Table 12, results from the anoikis resistance assay demonstrated that treatment with OST-01 showed a dose-dependent inhibition of anoikis resistance as compared to the ethanol control in all colon cancer cell lines tested. For example, LoVo and cells treated with OST-01 exhibited a dose-dependent inhibition of anoikis resistance based on cell count relative to cells treated with the ethanol control, and reached at least 47% inhibition of anoikis resistance at the highest concentration tested (8.0 μL/mL OST-01). Similarly, HCT116 cells treated with OST-01 exhibited a dose-dependent inhibition of anoikis resistance based on cell count relative to cells treated with the ethanol control, and reached about 40% inhibition of anoikis resistance at the highest concentration tested (8.0 μL/mL OST-01). Likewise, HT29 and SW480 cells treated with OST-01 exhibited a dose-dependent inhibition of anoikis resistance based on cell count relative to cells treated with the ethanol control, and reached at least 32% inhibition of anoikis resistance at the highest concentration tested (8.0 µL/mL OST-01). Lastly, SW620 cells treated with OST-01 exhibited a dose-dependent inhibition of anoikis resistance based on cell count relative to cells treated with the ethanol control, and reached about 20% inhibition of anoikis resistance at the highest concentration tested (8.0 µL/mL OST-01). Taken together, the results from the anoikis resistance assay demonstrated that treatment with OST-01 significantly inhibited anoikis resistance from all colon cancer cell lines tested, further demonstrating that the anti-oncogenic activity of OST-01 extends to the inhibition of solid cancer metastasis.

TABLE 12

OST-01 Inhibition of Anoikis Resistance in Colon Cancer Cell Lines

| Treatment | Percent Anolkis Resistance[1] | | | | |
|---|---|---|---|---|---|
| | LoVo | HCT116 | HT29 | SW480 | SW620 |
| Untreated | 100% | 100% | 100% | 100% | 100% |
| 0.5 µL/mL OST-01 | 91% | 98% | 99% | 97% | 9923% |
| 1.0 µL/mL OST-01 | 77% | 88% | 97% | 86% | 99% |
| 2.0 µL/mL OST-01 | 74% | 74% | 93% | 84% | 98% |
| 4.0 µL/mL OST-01 | 56% | 64% | 77% | 84% | 97% |
| 6.0 µL/mL OST-01 | 55% | 63% | 71% | 70% | 94% |
| 8.0 µL/mL OST-01 | 53% | 60% | 64% | 68% | 81% |

[1]Anoikis resistance of the ethanol control was taken as 100% and that of OST-01 treated groups was calculated as percentage of ethanol control.

Example 14

OST-01 Suppresses Cellular Infiltration Activity of Solid Cancer Cells

To investigate the effects of OST-01 on cancer cell invasion of solid cancer cells a cell invasion assay was conducted to determine whether OST-01 activity could disrupt the cellular infiltration activity of solid cancer cells.

The solid cancer cell lines MCF-7, A549, and HCT-116 were selected for these studies and maintained as described in Example 12.

Cell invasion is the ability of cells to migrate from one area and infiltrate into another through an extracellular matrix. Cell invasion is required for normal processes such as wound repair, vasculature formation and the inflammatory response as well as the abnormal invasion of tissues by tumor cells during metastasis. Cell invasion occurs in response to specific external signals, including chemical and mechanical stimuli. During invasion, extracellular matrix is enzymatically degraded by cellular proteases before cells migrate to the new location. A cell invasion assay utilizes a Boyden chamber coated with collagen I, where cells infiltrate the matrix and then migrate through a semipermeable membrane in response to stimulants or inhibitory compounds. The percent cell invasion can be analyzed directly by microscopy or using a plate reader.

In one series of experiments, MCF-7, A549, and HCT-116 cells were established in 3 cm culture dishes and grown to an approximate density of $1\times10^6$ cell or 80% confluency. Cell cultures are washed in warm PBS, serum-free media added, and either 1 µL/mL of OST-01 or 1 µL/mL control vehicle was then added to cells for each of the three solid cancer cell lines and incubated for 24 hours at 37° C. in 5% $CO_2$ incubator. Cell invasion was then assessed using a cell invasion assay (Cell Invasion Assay Kit (Collagen I), Abcam, MA) following protocols provided by the manufacture. Briefly, after treatment/starvation, cells were harvested by trypsinization, counted, and resuspended in serum-free culture media at a density of $2\times10^5$ cells/mL. A 2 mL aliquot of cell suspension was added to wells of the top chamber (previously coated with collagen I) of 24-well cell invasion (Boyden) chamber. Medium containing a Control Invasion Inducer was added to the bottom chamber. The cells were incubated for 16 hours at 37° C. in 5% $CO_2$ incubator to permit cells migrate through a semipermeable membrane in response to the Control Invasion Inducer. The membrane of the chambers was rinsed 3 times on both sides with medium. The upper surface of the membrane was scrubbed 3 times with a cotton swab and medium to remove noninvasive cells. Cells on the lower surface of the scrubbed membranes were fixed and stained with 100% methanol and 0.5% crystal violet, and random fields were counted under the light microscope.

As shown in FIGS. 17A-17F, results from the cell invasion assay demonstrated that treatment with OST-01 showed a dramatically decreased cell migration across the membrane as compared to the control in all solid cancer cell lines tested. For example, MCF-7 cells treated with OST-01 exhibited at least a 50% decrease in membrane migration based on cell count (see FIG. 17B) relative to cells treated with the vehicle control (see FIG. 17A). Similarly, HCT-116 cells treated with OST-01 exhibited at least an 80% decrease in membrane migration based on cell count (see FIG. 17D) relative to cells treated with the vehicle control (see FIG. 17C). Likewise, A549 cells treated with OST-01 exhibited at least an 60% decrease in membrane migration based on cell count (see FIG. 17F) relative to cells treated with the vehicle control (see FIG. 17E). Taken together, the results from the cell invasion assay demonstrated that treatment with OST-01 significantly decreased the migratory and invasion activities of cells from all three solid cancer cell lines tested, further demonstrating that the anti-oncogenic activity of OST-01 extends to the inhibition of solid cancer metastasis.

Example 15

OST-01 Changes of Gene Expression Profiles in Solid Cancer Cells

To investigate the effects of OST-on on gene expression in solid cancer cells, RNA sequencing was performed and analysis was conducted using Gene Set Enrichment Analysis (GSEA) to determine whether OST-01 activity could alter RNA expression profiles in cells from several different solid cancer cell lines.

In one series of experiments, cultures of cells from a BT474 triple negative breast cancer cell line were established in 10 cm culture dishes and grown to an approximate density of $10\times10^6$ cells. Total RNA isolation and GSEA were performed essentially as described in Example 8.

As shown in Table 13, results from the GSEA demonstrated that treatment with OST-showed induced significant upregulation of the TNFα, TGFβ, interferon, and P53 signaling pathways as well as inflammation and apoptosis and significant downregulation of the mTORC, c-myc, cell division, and FAO/OXPHOS signaling pathways in cells analyzed from a BT474 ripe negative breast cancer cell line.

TABLE 13

GSEA of BT474 Triple Negative Breast Cancer Cells

| Hallmark Gene Set | Up-Regulated | Down-Regulated | Adjusted P Value |
|---|---|---|---|
| TNFα Signaling via NFκB | 2.27 | | 0.00 |
| IL6 JAK STAT3 Signaling | 1.75 | | 0.00 |
| Inflammatory Response | 1.68 | | 0.00 |
| kRAS Signaling (Up) | 1.61 | | 0.00 |
| INFγ Response | 1.53 | | 0.01 |
| Allograft Rejection | 1.52 | | 0.01 |
| IL2 STAT5 Signaling | 1.44 | | 0.02 |
| INFα Response | 1.44 | | 0.02 |
| Hypoxia | 1.43 | | 0.02 |
| TGFβ Signaling | 1.42 | | 0.02 |
| UV Response (Down) | 1.39 | | 0.02 |
| Notch Signaling | 1.38 | | 0.02 |
| Apoptosis | 1.36 | | 0.03 |
| kRAS Signaling (Down) | 1.34 | | 0.04 |
| P53 Pathway | 1.34 | | 0.04 |
| Fatty Acid Metabolism | | −1.06 | 0.22 |
| Reactive Oxygen Species Pathway | | −1.20 | 0.07 |
| DNA Repair | | −1.22 | 0.07 |
| Peroxisome | | −1.27 | 0.05 |
| Protein Secretion | | −1.35 | 0.02 |
| Unfolded Protein Response | | −1.73 | 0.00 |
| G2M Checkpoint | | −1.75 | 0.00 |
| MYC Targets (v2) | | −1.91 | 0.00 |
| Oxidative Phosphorylation | | −1.94 | 0.00 |
| mTORC1 Signaling | | −2.04 | 0.00 |

In another series of experiments, cultures of cells from a MDA-MB-231 triple negative breast cancer cell line were established in 10 cm culture dishes and grown to an approximate density of $10 \times 10^6$ cells. Total RNA isolation and GSEA were performed essentially as described in Example 8.

As shown in Table 14, results from the GSEA demonstrated that treatment with OST-01 showed induced significant upregulation of the TNFα, TGFβ, interferon signaling pathways as well as inflammation and apoptosis and significant downregulation of the mTORC and c-myc signaling pathways as well as glycolysis in cells analyzed from a MDA-MB-231 triple negative breast cancer cell line.

TABLE 14

GSEA of MDA-MB-231 Triple Negative Breast Cancer Cells

| Hallmark Gene Set | Up-Regulated | Down-Regulated | Adjusted P Value |
|---|---|---|---|
| TNFα Signaling via NFκB | 2.15 | | 0.00 |
| IL6 JAK STAT3 Signaling | 1.56 | | 0.01 |
| INFα Response | 1.49 | | 0.02 |
| INFγ Response | 1.47 | | 0.02 |
| Inflammatory Response | 1.41 | | 0.05 |
| Apoptosis | 1.33 | | 0.11 |
| Allograft Rejection | 1.31 | | 0.12 |
| kRAS Signaling (Up) | 1.29 | | 0.13 |
| Heme Metabolism | 1.24 | | 0.21 |
| UV Response (Up) | 1.20 | | 0.27 |
| Unfolded Protein Response | | −1.40 | 0.05 |
| Epithelial Mesenchymal Transition | | −1.43 | 0.05 |
| Cholesterol Homeostasis | | −1.47 | 0.04 |
| Apical Surface | | −1.48 | 0.04 |
| MYC Targets (v2) | | −1.57 | 0.03 |
| Glycolysis | | −1.80 | 0.00 |
| G2M Checkpoint | | −1.88 | 0.00 |
| mTORC1 Signaling | | −1.98 | 0.00 |
| E2F Targets | | −2.37 | 0.00 |
| MYC Targets (v1) | | −2.46 | 0.00 |

In another series of experiments, cultures of cells from a 4T1 triple negative breast cancer cell line were established in 10 cm culture dishes and grown to an approximate density of $10 \times 10^6$ cells. Total RNA isolation and GSEA were performed essentially as described in Example 8.

As shown in Table 15, results from the GSEA demonstrated that treatment with OST-01 showed induced significant upregulation of the TNFα signaling pathway as well as the UV response, myogenesis and inflammation and significant downregulation of the mTORC, c-myc, cell division, and FAO/OXPHOS signaling pathways as well as glycolysis in cells analyzed from a 4T1 triple negative breast cancer cell line.

TABLE 15

GSEA of 4T1 Triple Negative Breast Cancer Cells

| Hallmark Gene Set | Up-Regulated | Down-Regulated | Adjusted P Value |
|---|---|---|---|
| TNFα Signaling via NFκB | 1.63 | | 0.00 |
| Inflammatory Response | 1.43 | | 0.05 |
| kRAS Signaling (Down) | 1.41 | | 0.05 |
| Pancreas β Cells | 1.29 | | 0.22 |
| Allograft Rejection | 1.26 | | 0.26 |
| Apical Surface | 1.21 | | 0.42 |
| IL6 JAK STAT3 Signaling | 1.20 | | 0.38 |
| TGFβ Signaling | 1.20 | | 0.37 |
| Myogenesis | 1.13 | | 0.67 |
| UV Response (Up) | 1.10 | | 0.69 |
| Adipogenesis | | −1.58 | 0.00 |
| E2F Targets | | −1.65 | 0.00 |
| Reactive Oxygen Species Pathway | | −1.71 | 0.00 |
| Fatty Acid Metabolism | | −1.73 | 0.00 |
| Oxidative Phosphorylation | | −1.74 | 0.00 |
| Glycolysis | | −1.82 | 0.00 |
| Unfolded Protein Response | | −1.95 | 0.00 |
| MYC Targets (v2) | | −2.02 | 0.00 |
| MYC Targets (v1) | | −2.25 | 0.00 |
| mTORC1 Signaling | | −2.28 | 0.00 |

In another series of experiments, cultures of cells from a A549 lung cancer cell line were established in 10 cm culture dishes and grown to an approximate density of $10 \times 10^6$ cells. Total RNA isolation and GSEA were performed essentially as described in Example 8.

As shown in Table 16, results from the GSEA demonstrated that treatment with OST-0 showed induced significant upregulation of the TNFα, TGFβ, c-myc, P53, signaling pathways as well as the inflammatory response and apoptosis and significant downregulation of the cell division pathway, angiogenesis, and glycolysis in cells analyzed from an A549 lung cancer cell line.

TABLE 16

GSEA of A549 Lung Cancer Cells

| Hallmark Gene Set | Up-Regulated | Down-Regulated | Adjusted P Value |
|---|---|---|---|
| TNFα Signaling via NFκB | 2.45 | | 0.00 |
| MYC Targets (v2) | 1.69 | | 0.00 |
| P53 Pathway | 1.65 | | 0.01 |
| DNA Repair | 1.533 | | 0.02 |
| Inflammatory Response | 1.46 | | 0.04 |
| Hypoxia | 1.44 | | 0.04 |
| kRAS Signaling (UP) | 1.44 | | 0.03 |
| Apoptosis | 1.31 | | 0.10 |
| UV Response (Up) | 1.20 | | 0.24 |
| TGFβ Signaling | 1.13 | | 0.37 |
| Apical Surface | | −1.67 | 0.00 |
| Hedgehog Signaling | | −1.77 | 0.00 |
| G2M Checkpoint | | −1.78 | 0.00 |
| Estrogen Response (Late) | | −1.80 | 0.00 |
| Apical Junction | | −1.80 | 0.00 |

TABLE 16-continued

GSEA of A549 Lung Cancer Cells

| Hallmark Gene Set | Up-Regulated | Down-Regulated | Adjusted P Value |
|---|---|---|---|
| Coagulation | | −1.82 | 0.00 |
| Epithelial Mesenchymal Transition | | −1.89 | 0.00 |
| Glycolysis | | −1.92 | 0.00 |
| E2F Targets | | −1.95 | 0.00 |
| Angiogenesis | | −1.95 | 0.00 |

In another series of experiments, cultures of cells from a MiaPaCa-2 pancreatic cancer cell line were established in 10 cm culture dishes and grown to an approximate density of $10 \times 10^6$ cells. Total RNA isolation and GSEA were performed essentially as described in Example 8.

As shown in Table 17, results from the GSEA demonstrated that treatment with OST-01 showed induced significant upregulation of the P53, TNFα, and interferon signaling pathways as well as inflammation and apoptosis and significant downregulation of mTORC, estrogen response, and WNT signaling pathways in cells analyzed from a MiaPaCa-2 pancreatic cancer cell line.

TABLE 17

GSEA of MiaPaCa-2 Pancreatic Cancer Cells

| Hallmark Gene Set | Up-Regulated | Down-Regulated | Adjusted P Value |
|---|---|---|---|
| Pancreatic β Cells | 1.81 | | 0.05 |
| P53 Pathway | 1.72 | | 0.05 |
| TNFα Signaling via NFκB | 1.60 | | 0.5 |
| Hypoxia | 1.60 | | 0.6 |
| Spermatogenesis | 1.58 | | 0.5 |
| Apoptosis | 1.56 | | 0.6 |
| INFγ Response | 1.50 | | 0.8 |
| IL2 STAT5 Signaling | 1.45 | | 0.9 |
| Inflammatory Response | 1.40 | | 0.9 |
| Heme Metabolism | 1.37 | | 0.9 |
| mTORC1 Signaling | | −0.96 | 0.75 |
| Angiogenesis | | −1.09 | 0.69 |
| Apical Junction | | −1.09 | 0.75 |
| Cholesterol Homeostasis | | −1.18 | 0.55 |
| Wntβ Catenin Signaling | | −1.20 | 0.55 |
| Estrogen Response (Late) | | −1.21 | 0.61 |
| Notch Signaling | | −1.24 | 0.59 |
| Epithelial Mesenchymal Transition | | −1.28 | 0.59 |
| Estrogen Response (Early) | | −1.34 | 0.51 |

In another series of experiments, cultures of cells from a PANC-1 pancreatic cancer cell line were established in 10 cm culture dishes and grown to an approximate density of $10 \times 10^6$ cells. Total RNA isolation and GSEA were performed essentially as described in Example 8.

As shown in Table 18, results from the GSEA demonstrated that treatment with OST-showed induced significant upregulation of the P53, TNFα, and interferon signaling pathways as well as inflammation and significant downregulation of mTORC signaling pathway as well as adipogenesis, myogenesis, bile acid metabolism, and glycolysis in cells analyzed from a PANC-1 pancreatic cancer cell line.

TABLE 18

GSEA of PANC-1 Pancreatic Cancer Cells

| Hallmark Gene Set | Up-Regulated | Down-Regulated | Adjusted P Value |
|---|---|---|---|
| Spermatogenesis | 1.55 | | 0.06 |
| UV Response (Up) | 1.48 | | 0.09 |

TABLE 18-continued

GSEA of PANC-1 Pancreatic Cancer Cells

| Hallmark Gene Set | Up-Regulated | Down-Regulated | Adjusted P Value |
|---|---|---|---|
| Inflammatory Response | 1.45 | | 0.11 |
| TNFα Signaling via NFκB | 1.39 | | 0.14 |
| Pancreatic β Cells | 1.39 | | 0.16 |
| IL6 JAK STAT3 Signaling | 1.36 | | 0.15 |
| P53 Pathway | 1.22 | | 0.25 |
| INFγ Response | 1.21 | | 0.22 |
| kRAS Signaling | 1.21 | | 0.23 |
| mTORC1 Signaling | | −1.26 | 0.23 |
| Apical Junction | | −1.28 | 0.23 |
| Adipogenesis | | −1.29 | 0.22 |
| Cholesterol Homeostasis | | −1.29 | 0.24 |
| Glycolysis | | −1.30 | 0.24 |
| Myogenesis | | −1.31 | 0.25 |
| Bile Acid Metabolism | | −1.36 | 0.24 |

Example 16

OST-01 Suppresses Breast Tumor Formation in Animal Model

To investigate the effects of OST-01 in solid tumor formation, a breast cancer mouse model was used to determine whether OST-01 administration was effective in treating this cancer.

The solid cancer cell line MCF-7 was selected for these studies and maintained as described in Example 12.

In one series of experiments, a breast tumor xenograft mouse model was generated by subcutaneously transplanting $0.5 \times 10^6$ MCF-7 cells into left and right side of upper thigh region of three female NOD/SCID/γ chain$^{null}$ mice (NOD scid gamma mouse (NSG), Jackson Laboratory, MA). Animals were housed throughout the experiments in micro-insulator cages in a pathogen-free condition and handled in laminar flow hoods. After cancer cell transplantation, animals were monitored for tumor growth for 14. Treatment commenced on Day 14 after cancer cell transplant with each animal being intraperitoneally administered 1) a single dose of 100 μL of OST-01 for 14 consecutive days directly to tumor located in right upper thigh region; and 2) a single dose of 100 μL of vehicle control for 14 consecutive days directly to tumor located in left upper thigh region (see FIG. 18A).

To examine effects of OST-01 on breast cancer tumor formation, the size of isolated tumors were determined. Animals were euthanized on Day 20, tumors dissected from the upper thigh regions, and surrounding fat was removed without causing any mechanical damage to tumor. The resulting isolated tumors were then measured and photographed.

As shown in FIGS. 18B-18D, tumors in xenograft animals treated with OST-01 were reduced by at least 50% in size relative to the tumors formed in animals treated with the vehicle control. For example, FIG. 18B shows that in animal 1, the tumor treated with OST-01 exhibited a size reduction of at least 50% relative to tumor treated with the vehicle control, FIG. 18C shows that in animal 2, the tumor treated with OST-01 exhibited a size reduction of at least 60% relative to tumor treated with the vehicle control, while FIG. 18D remarkably shows that in animal 3 no tumor was detected after treated with OST-01 albeit the tumor treated with the vehicle control was clearly present. Taken together, OST-01 treatment significantly suppressed breast tumor formation in these animals and demonstrates that OST-01 has anti-oncogenic activity in vivo.

In another series of experiments, a breast tumor xenograft mouse model was generated by subcutaneously transplanting $0.5 \times 10^6$ BT474 cells into left and right side of upper thigh region of three female NOD/SCID/γ chain$^{null}$ mice (NOD scid gamma mouse (NSG), Jackson Laboratory, MA). Animals were housed throughout the experiments in micro-insulator cages in a pathogen-free condition and handled in laminar flow hoods. After cancer cell transplantation, animals were monitored for tumor growth for 14. Treatment commenced on Day 14 after cancer cell transplant. Animals were then randomly divided into two groups of four animals each. Group 1 animals were administered by oral gavage a single dose of 20 μL/25 g of OST-01 twice a day for 5 consecutive weeks and Group 2 animals being administered by oral gavage a single dose of 20 μL/25 g of vehicle control twice a day for 5 consecutive weeks. Animals were housed throughout the experiments in micro-insulator cages in a pathogen-free condition and handled in laminar flow hoods. To examine effects of OST-01, animals were then euthanized and tumor size determined. Data are presented as mean±standard error (SE), as indicated. $p<0.05$ was considered statistically significant.

Figure 18G:
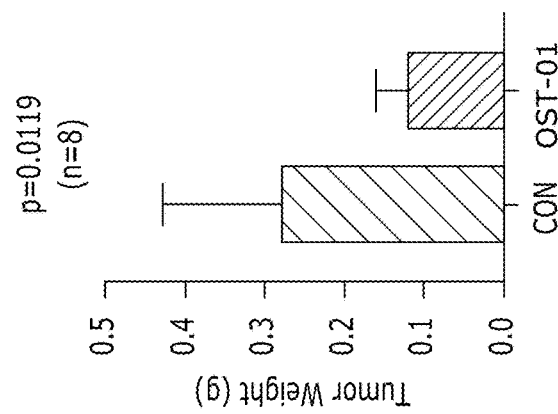
Figure 18F:
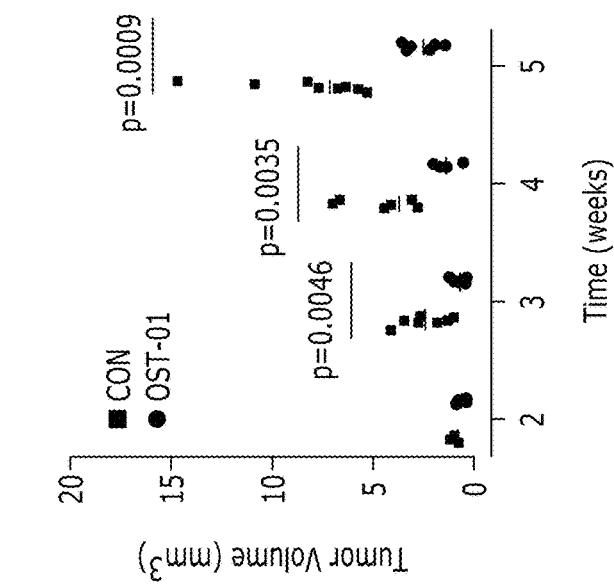
Figure 18E:
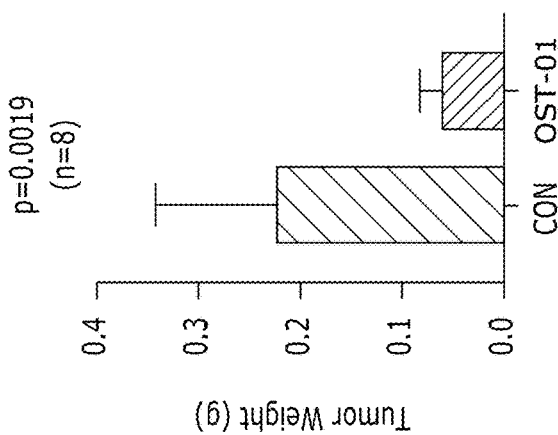

As shown in FIGS. 18E-18F, tumors in xenograft animals from a xenograft mouse model using BT474 treated with OST-01 were reduced by at least 50% in size relative to the tumors formed in animals treated with the vehicle control. For example, FIG. 18E shows that in an animal treated with OST-01, the tumor exhibited a statistically significant ($p=-0.0019$) size reduction of at least 70% relative to tumor treated with the vehicle control. Similarly, FIG. 18F shows that a size reduction in tumor size was observed after three weeks of treatment (3 weeks, $p=0.0046$) and this size reduction progressively continue as treatment continued (4 weeks, $p=0.0035$) and (5 weeks, $p=0.0009$). Taken together, OST-01 treatment significantly suppressed breast tumor formation in these animals and demonstrates that OST-01 has anti-oncogenic activity in vivo.

In another series of experiments, a breast tumor xenograft mouse model was generated by subcutaneously transplanting $0.5 \times 10^6$ MDA-MB-231 cells into left and right side of upper thigh region of three female NOD/SCID/γ chain$^{null}$ mice (NOD scid gamma mouse (NSG), Jackson Laboratory, MA). Animals were housed throughout the experiments in micro-insulator cages in a pathogen-free condition and handled in laminar flow hoods. After cancer cell transplantation, animals were monitored for tumor growth for 14. Treatment commenced on Day 14 after cancer cell transplant. Animals were then randomly divided into two groups of four animals each. Group 1 animals were administered by oral gavage a single dose of 20 μL/25 g of OST-01 twice a day for 5 consecutive weeks and Group 2 animals being administered by oral gavage a single dose of 20 μL/25 g of vehicle control twice a day for 5 consecutive weeks. Animals were housed throughout the experiments in micro-insulator cages in a pathogen-free condition and handled in laminar flow hoods. To examine effects of OST-01, animals were then euthanized and tumor size determined. Data are presented as mean±standard error (SE), as indicated. $p<0.05$ was considered statistically significant.

As shown in FIG. 18G, tumors from a xenograft mouse model using MDA-MB-231 treated with OST-01 were reduced by at least 50% in size relative to the tumors treated with the vehicle control. For example, FIG. 18G shows that in an animal treated with OST-01, the tumor exhibited a statistically significant ($p=-0.0119$) size reduction of at least 60% relative to tumor treated with the vehicle control. Taken together, OST-01 treatment significantly suppressed breast tumor formation in these animals and demonstrates that OST-01 has anti-oncogenic activity in vivo.

Example 17

OST-01 Suppresses Colon Tumor Formation in Animal Model

To investigate the effects of OST-01 in solid tumor formation, a colon cancer mouse model was used to determine whether OST-01 administration was effective in treating this cancer.

The solid cancer cell line HCT-116 was selected for these studies and maintained as described in Example 12.

Figure 19A:
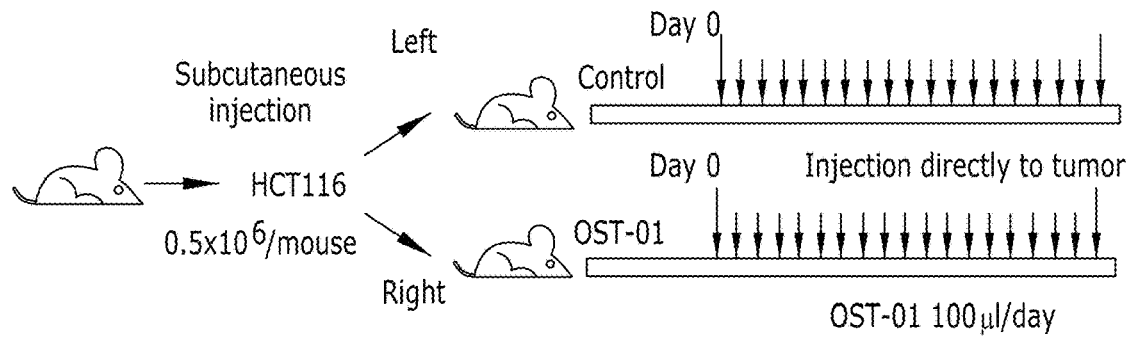
FIGS. 19A-19C show results obtained from a colon tumor xenograft mouse model with FIG. 19A showing a diagram of the study design of colon tumor xenograft mouse model using HCT-116 colon cancer cells.

To generate a colon tumor xenograft mouse model, $0.5 \times 10^6$ HCT-116 cells were subcutaneously transplanted into left and right side of upper thigh region of three female NOD/SCID/γ chain$^{null}$ mice (NOD scid gamma mouse (NSG), Jackson Laboratory, MA). Animals were housed throughout the experiments in micro-insulator cages in a pathogen-free condition and handled in laminar flow hoods. After cancer cell transplantation, animals were monitored for tumor growth for 14. Treatment commenced on Day 14 after cancer cell transplant with each animal being intraperitoneally administered 1) a single dose of 100 μL (or 20 μL) of OST-01 for 14 consecutive days directly to tumor located in right upper thigh region; and 2) a single dose of 100 μL (or 20 μL) of vehicle control for 14 consecutive days directly to tumor located in left upper thigh region (see FIG. 19A).

To examine effects of OST-01 on colon cancer tumor formation, the size of isolated tumors were determined. Animals were sacrificed on Day 15, tumors dissected from the upper thigh regions, and surrounding fat was removed without causing any mechanical damage to tumor. The resulting isolated tumors were then weighted, measured, and photographed.

Figure 19B:
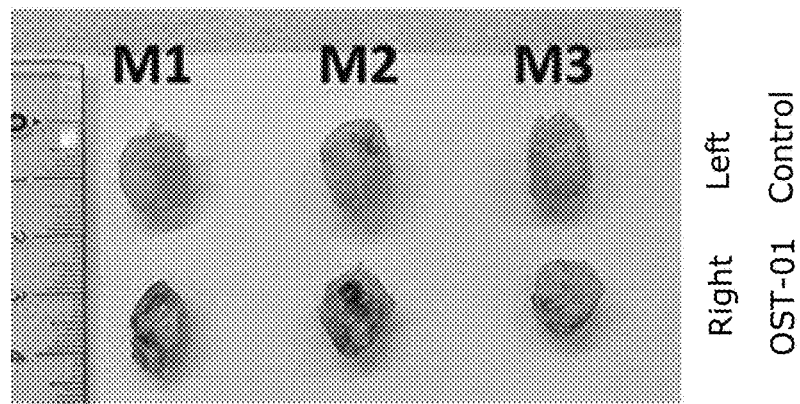
Figure 19C:
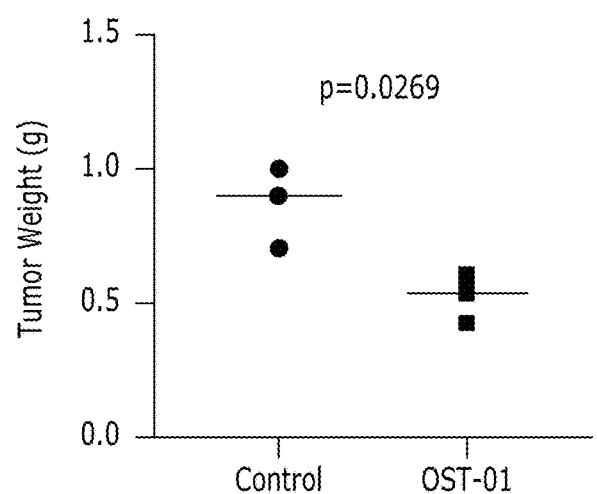

As shown in FIGS. 19B & 19C, tumors in xenograft animals treated with OST-01 were reduced by about 35% in size relative to the tumors formed in animals treated with the vehicle control. For example, FIG. 19B shows that the tumors treated with OST-01 exhibited a size reduction of about 35% relative to tumors treated with the vehicle control. In addition, as shown in FIG. 19C, the mean weight of tumors treated with OST-01 was about 0.5 g while the mean weight of tumors treated with the vehicle control as about 0.9 g, this represents a statistically significant reduction in mean tumor weight ($p=0.0269$). Taken together, OST-01 treatment significantly suppressed colon tumor formation in these animals and demonstrates that OST-01 has anti-oncogenic activity in vivo.

Example 18

OST-01 Suppresses Lung Tumor Formation in Animal Model

To investigate the effects of OST-01 in solid tumor formation, lung cancer mouse models were used to determine whether OST-01 administration was effective in treating this cancer.

The solid cancer cell line A549 was selected for these studies and maintained as described in Example 12.

Figure 20A:
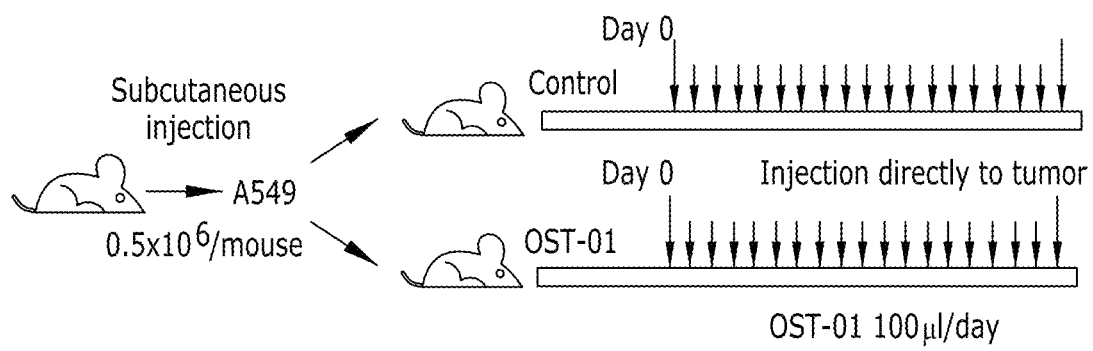

In one series of experiments, a lung tumor xenograft mouse model was generated by subcutaneously transplanted $1\times10^6$ A549 cells into a right inguinal region of eight female NOD/SCID/γ chain$^{null}$ mice (NOD scid gamma mouse (NSG), Jackson Laboratory, MA). Animals were housed throughout the experiments in micro-insulator cages in a pathogen-free condition and handled in laminar flow hoods. After cancer cell transplantation, animals were monitored for tumor growth for 14. Treatment commenced on Day 14 after cancer cell transplant. Animals were then randomly divided into two groups of four animals each. Group 1 animals received both a single dose of 1 μL/g/day of OST-01 administered by oral gavage and a single dose of 100 μL of OST-01 intraperitoneally administered directly into the tumor located in the right inguinal region, with both doses being administered for 20 consecutive days (see FIG. 20A). Group 2 animals received both a single dose of 1 μL/g/day of vehicle control administered by oral gavage and a single dose of 100 μL of vehicle control intraperitoneally administered directly into the tumor located in the right inguinal region, with both doses being administered for 20 consecutive days (see FIG. 20A).

To examine effects of OST-01 on lung cancer tumor formation, the size of isolated tumors as well as the expression of oncogenic and apoptosis regulated proteins were determined. For tumor size determinations, animals were sacrificed on Day 20, tumors dissected from the right inguinal regions, and surrounding fat was removed without causing any mechanical damage to tumor. The resulting isolated tumors were then measured and photographed.

Figures 20B, 20C, 20D, 20E:
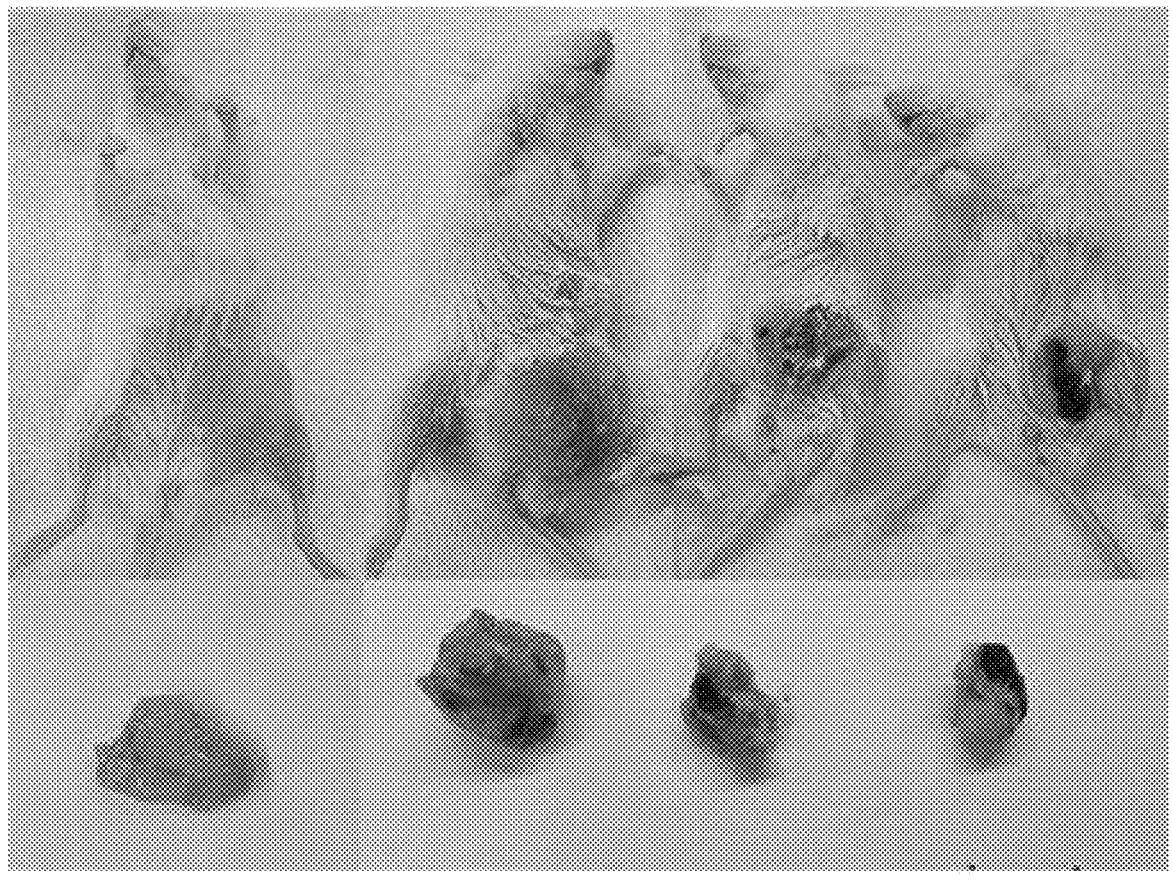

As shown in FIGS. 20B-20I, tumors in xenograft animals treated with OST-01 were reduced by at least 50% in size relative to the tumors formed in animals treated with the vehicle control. For example, FIG. 20D shows that in an animal treated with OST-01, the tumor exhibited a size reduction of at least 50% relative to tumor treated with the vehicle control (see FIGS. 20B & 20C). Similarly, FIG. 20E shows that in an animal treated with OST-01, the tumor exhibited a size reduction of at least 60% relative to tumor treated with the vehicle control (see FIGS. 20B & 20C). Likewise, FIGS. 20G & 20I show that in an animal treated with OST-01, the tumor exhibited a size reduction of at least 60% relative to tumor treated with the vehicle control (see FIGS. 20F & 20H). Taken together, OST-01 treatment significantly suppressed lung tumor formation in these animals and demonstrates that OST-01 has anti-oncogenic activity in vivo.

For protein expression determination, isolated tumors were immediately processed by adding the tumors to 4% paraformaldehyde at 18° C. for 4 hours. Fixed tumor tissue was washed three times with PBS and incubated with ice-cold cryoprotectant (CPT) solution at 4° C. for 24 hours. Tumor tissue was then incubating with embedding media at 60° C. for 45 minutes, transferred to a tissue mold, dried at 18° C. for 30 minutes, and stored at −80° C. at least over night until sectioning. Tissue sections were cut at −23° C. using a microtome with a thickness of 20 μm and transferred to a microscope slide for staining. Tissue frozen section were washed with PBS, fixed in 4% paraformaldehyde for 15 minutes and permeabilized in 0.5% Triton X-100 for 15 minutes. Prepared tissue sections were blocked by incubating in 5% BSA for 30 minutes and then incubated with either 1) an anti-c-myc rabbit monoclonal antibody (AB 5605, Cell Signaling, MA) and then a goat anti-rabbit IgG ALEXA FLUOR® 594-linked secondary antibody (A32740, Thermo Scientific, CO); 2) an anti-p-AKT rabbit monoclonal antibody (AB 4060, Cell Signaling, MA) and then a goat anti-rabbit IgG ALEXA FLUOR® 488-linked secondary antibody (A32731, Thermo Scientific, CO); 3) an anti-PCNA mouse monoclonal antibody (PC-10, Santa Cruz, CA) and then a goat anti-mouse IgG ALEXA FLUOR® 488-linked secondary antibody (A32723, Thermo Scientific, CO); 4) an anti-cleaved caspase 3 rabbit monoclonal antibody (AB 9602, Cell Signaling, MA) and then a goat anti-rabbit IgG HRP-linked secondary antibody (AB A32733, Thermo Scientific, CO); 5) an anti-γH2AX(phospho 139) mouse monoclonal antibody (AB 22551, Abcam, MA) and then a goat anti-mouse IgG ALEXA FLUOR® 488-linked secondary antibody (A32723, Thermo Scientific, CO); or 6) an anti-p53 mouse monoclonal antibody (DO-1, Santa Cruz, CA) and then a goat anti-mouse IgG ALEXA FLUOR® 594-linked secondary antibody (A32742, Thermo Scientific, CO). Cells were then counterstained with the fluorescent nucleic acid dye DAPI (D9542, Sigma-Aldrich, MO) to identify nuclei. After staining, cells were washed with ice-cold PBS, analysis for fluorescence using a confocal microscope (Carl Zeiss, Jena, Germany), and representative images obtained.

As shown in FIGS. 21A-21C, results from the immunofluorescence staining for three oncogenic biomarkers demonstrated that treatment with OST-01 showed a dramatically decreased the expression levels of all three biomarkers in tumors as compared to tumors treated with the vehicle control. For example, as shown in FIG. 21A, expression levels of the oncogenic protein c-MYC was reduced by at least 90% relative to the expression levels present in sections of tumor treated with the vehicle control. Similarly, as shown in FIG. 21B, expression levels of the oncogenic protein p-AKT was reduced by at least 70% relative to the expression levels present in sections of tumor treated with the vehicle control. Likewise, as shown in FIG. 21C, expression levels of the oncogenic protein PCNA was reduced by at least 80% relative to the expression levels present in sections of tumor treated with the vehicle control. Taken together, OST-01 treatment significantly suppressed the expression of oncogenic proteins in colon tumors and further demonstrates that the in vivo anti-oncogenic activity of OST-01 includes the suppression oncogenic protein expression.

Furthermore, as shown in FIGS. 21D-21F, results from the immunofluorescence staining for three apoptosis biomarkers demonstrated that treatment with OST-01 showed a dramatically increased the expression levels of all three biomarkers in tumors as compared to tumors treated with the vehicle control. For example, as shown in FIG. 21D, expression levels of the cleaved active form of the apoptotic protein caspase-3 was increased by at least 80% relative to the expression levels present in sections of tumor treated with the vehicle control. Similarly, as shown in FIG. 21E, expression levels of the phosphorylated active form of the apoptotic protein H2A.X was increased by at least 90% relative to the expression levels present in sections of tumor treated with the vehicle control. Likewise, as shown in FIG. 21F, expression levels of the apoptotic protein p53 was increased by at least 80% relative to the expression levels present in sections of tumor treated with the vehicle control. Taken together, OST-01 treatment significantly enhanced the expression of apoptotic proteins in colon tumors and further demonstrates that the in vivo anti-oncogenic activity of OST-01 includes the activation of apoptosis regulated proteins essential in initiating programed cell death and apoptosis.

In another series of experiments, a lung tumor xenograft mouse model was generated by subcutaneously transplanted $1\times10^6$ A549 cells into a right inguinal region of eight female NOD/SCID/γ chain$^{null}$ mice (NOD scid gamma mouse (NSG), Jackson Laboratory, MA). Animals were housed throughout the experiments in micro-insulator cages in a pathogen-free condition and handled in laminar flow hoods. After cancer cell transplantation, animals were monitored for tumor growth for 7 days. Treatment commenced on Day 7 after cancer cell transplant. Animals were then randomly divided into two groups of four animals each. Group 1 animals were administered by oral gavage a single dose of 20 µL/25 g of OST-01 twice a day for 5 consecutive weeks and Group 2 animals being administered by oral gavage a single dose of 20 µL/25 g of vehicle control twice a day for 5 consecutive weeks. Animals were housed throughout the experiments in micro-insulator cages in a pathogen-free condition and handled in laminar flow hoods. To examine effects of OST-01, animals were then euthanized and tumor size determined. Data are presented as mean±standard error (SE), as indicated. $p<0.05$ was considered statistically significant.

Figure 22A:
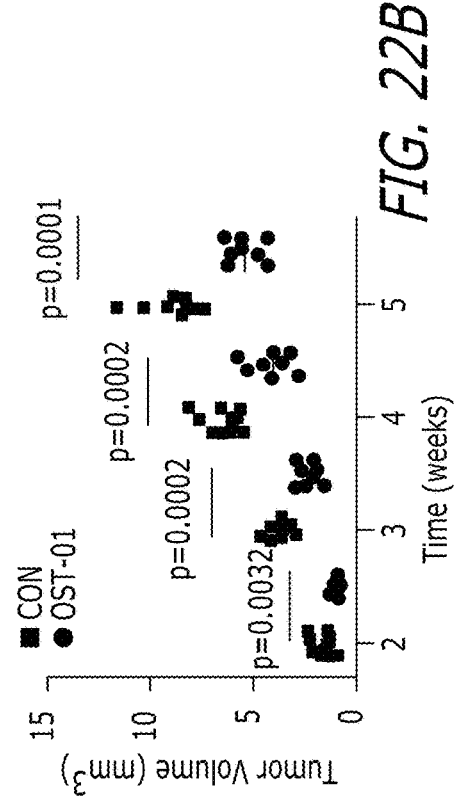
FIGS. 22A-22B show results obtained from a lung tumor xenograft mouse model using A549 lung cancer cells with FIG. 22A showing a graph of tumor weight in animals from xenograft mouse model using A549 lung cancer cells treated with either OST-01 or a vehicle control by oral gavage.
Figure 22B:
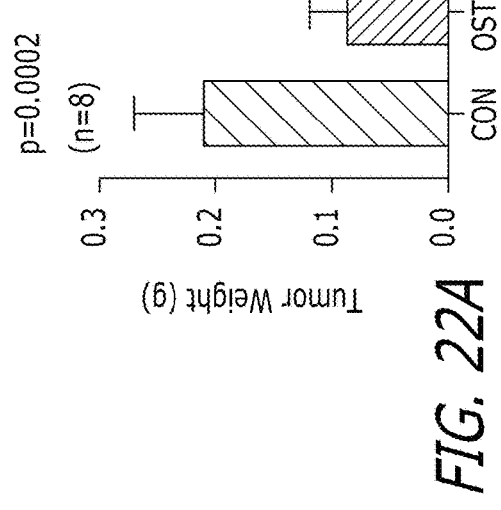

As shown in FIG. 22A-22B, tumors in xenograft animals treated with OST-01 were reduced by at least 50% in size relative to the tumors formed in animals treated with the vehicle control. For example, FIG. 22A shows that in an animal treated with OST-01, the tumor exhibited a statistically significant ($p=-0.0002$) size reduction of at least 50% relative to tumor treated with the vehicle control. Similarly, FIG. 22B shows that a size reduction in tumor size was observed after two weeks of treatment (2 weeks, $p=0.0032$) and this size reduction progressively continue as treatment continued (3 weeks, $p=0.0002$), (4 weeks, $p=0.0002$), and (5 weeks, $p=0.0001$). Taken together, OST-01 treatment significantly suppressed lung tumor formation in these animals and demonstrates that OST-01 has anti-oncogenic activity in vivo.

Example 19

OST-01 Suppresses Brain Tumor Formation in Animal Model

In another series of experiments, a brain tumor xenograft mouse model was generated by subcutaneously transplanting $0.5 \times 10^6$ LN-229 cells into right side of upper thigh region of nine female NOD/SCID/γ chain$^{null}$ mice (NOD scid gamma mouse (NSG), Jackson Laboratory, MA). An LN-229 cell line (CRL-2611) was obtained from the American Type Culture Collection (ATCC). LN-229 cells are epithelial cells isolated from the right frontal parieto-occipital cortex of a 60-year-old human female subject diagnosed with glioblastoma. Animals were housed throughout the experiments in micro-insulator cages in a pathogen-free condition and handled in laminar flow hoods. After cancer cell transplantation, animals were monitored for tumor growth for 7 days. Treatment commenced on Day 7 after cancer cell transplant. Animals were then randomly divided into two groups of four animals each. Group 1 animals were administered by oral gavage a single dose of 20 µL/25 g of OST-01 twice a day for 5 consecutive weeks and Group 2 animals being administered by oral gavage a single dose of 20 µL/25 g of vehicle control twice a day for 5 consecutive weeks. Animals were housed throughout the experiments in micro-insulator cages in a pathogen-free condition and handled in laminar flow hoods. To examine effects of OST-01, animals were then euthanized and tumor size determined. Data are presented as mean±standard error (SE), as indicated. $p<0.05$ was considered statistically significant.

Figure 23A:
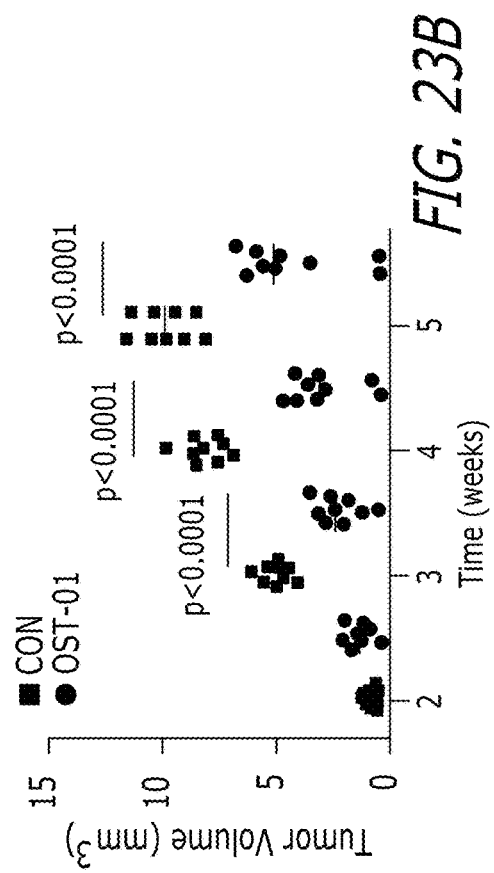
FIGS. 23A-23B show results obtained from a brain tumor xenograft mouse model using LN229 glioblastoma cancer cells with FIG. 23A showing a graph of tumor weight in animals from xenograft mouse model using LN229 glioblastoma cancer cells treated with either OST-01 or a vehicle control by oral gavage.
Figure 23B:
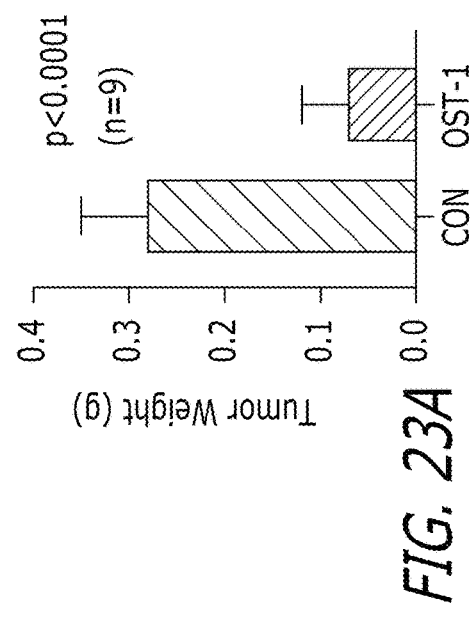

As shown in FIG. 23A-23B, tumors in xenograft animals treated with OST-01 were reduced by at least 50% in size relative to the tumors formed in animals treated with the vehicle control. For example, FIG. 23A shows that in an animal treated with OST-01, the tumor exhibited a statistically significant ($p=0.0001$) size reduction of about 200% relative to tumor treated with the vehicle control. Similarly, FIG. 23B shows that a size reduction in tumor size was observed after three weeks of treatment (3 weeks, $p=0.0001$) and this size reduction progressively continue as treatment continued (4 weeks, $p=0.0001$) and (5 weeks, $p=0.0001$). Taken together, OST-01 treatment significantly suppressed brain tumor formation in these animals and demonstrates that OST-01 has anti-oncogenic activity in vivo.

Example 20

Isolation of OST-01 Active Compounds

To isolate one or more active compounds of OST-01 responsible for its anti-oncogenic activity, purification methods were conducted on extracts disclosed herein to identify and isolate one or more anti-oncogenic phytochemicals disclosed herein.

OST-01 was prepared according to Example 1.

The AML cell lines MV-4-11 and THP-1 were selected for these studies and maintained as described in Example 2. THP-1 cells are monocyte isolated from peripheral blood from an adult male diagnosed with acute monocytic leukemia.

As a first step, high-performance liquid chromatography (HPLC) was used to separate, identify, and quantify one or more active components contained in OST-01. This technique relies on passing a pressurized liquid solvent containing a sample mixture through a column filled with a solid adsorbent material. Components contained within the sample mixture are separated from each other due to their different degrees of interaction with the adsorbent material, causing different flow rates through this material, and leading to the separation of the components as they flow out of the column.

Figures 24A, 24B:
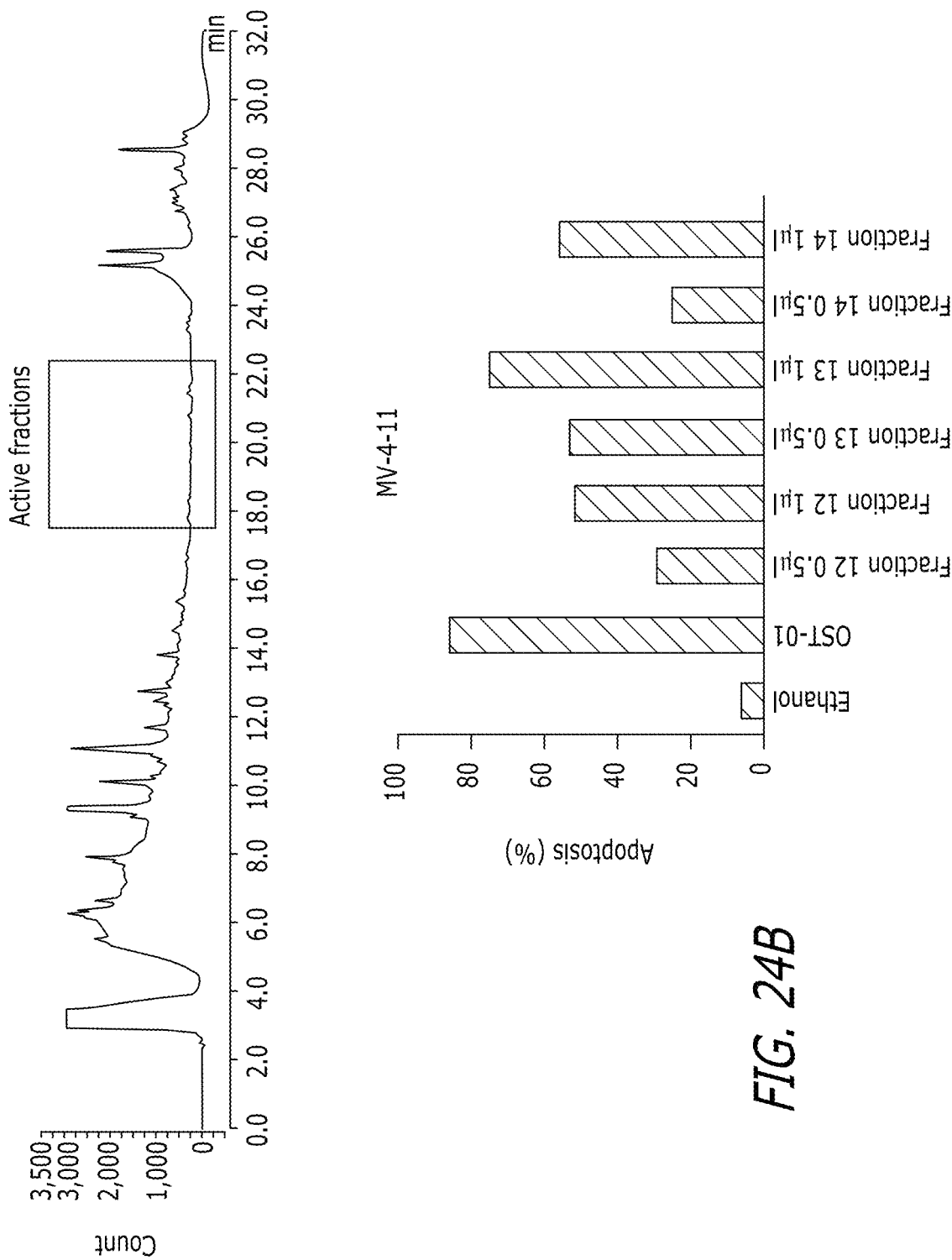
FIGS. 24A-24B show isolation of an antioncogenic compound isolated from OST-01 with FIG. 24A showing a representative UV-HPLC chromatogram at 226 nm showing identification of eighteen fractions of OST-01.

In one series of experiments, 120 µL injection volume of OST-01 was analyzed by ultraviolet reversed phase high performance liquid chromatography (UV-RPHPLC) with a semi-preparative C18 column (XBridge 4.6 mm×250 mm, 3.5 µM particle size, WATERS™, MA) and a mobile phase gradient using water, 0.1% trifluoroacetic acid (Solvent A) and methanol, 0.1%0.1% trifluoroacetic acid (Solvent B). The flow rate was maintained at 1 mL/min with a gradient from 10% to 30% Solvent B for 3 min, 30% to 99% Solvent B, for 22 min, 99% Solvent B for 5 min, 10% Solvent B to 2 min. The elution of metabolites was monitored using UV detection at 214 nm, 226 nm, and 280 nm. The analysis of OST-01 by UV-RPHPLC resulted in the elution of eighteen different fractions, designated F1-F18, over the course of the 32-minute retention time span (FIG. 24A). The fraction eluting under individual peaks were separately collected in different vials, concentrated using a vacuum concentrator, lyophilized, and stored until subsequently analysis for bioactivity and mass spectrometric characterization.

In one series of bioactivity experiments, each fraction was tested for OST-01 activity using an apoptosis flow cytometry assay. Apoptosis flow cytometry assays were performed essentially as described in Example 3. In one series of experiments, cultures MV-4-11 cells were grown to an appropriate density and approximately 20,000 cells/100 µL were seeded into wells of 96-well cell culture microplate.

For each fraction, either 0.5 μL/mL of a fraction or 1 μL/mL of a fraction was then added to transferred cells for each cell line and incubated for 24 hours at 37° C. in 5% $CO_2$ incubator. Control samples included 1 μL/mL of ethanol as a negative control for activity and 1 μL/mL of OST-01 as a positive control for activity. Cells were then assessed for apoptosis by an apoptosis flow cytometry assay employing with a fluorochrome-conjugated Annexin V and/or the fluorescent nucleic acid dye 4,6-diamidino-2-phenylindole (DAPI) (APC Annexin V, BD Bioscience, CA) following protocols provided by the manufacture. Briefly, after OST-01 treatment, cells were washed twice with an Annexin V buffered solution, resuspended in the same buffer at a concentration of $1\times10^6$ cells/mL, and 100 μL aliquoted transferred to 1 mL culture tubes. Aliquots were then incubated in the dark for 15 minutes with either 1) an Annexin-V-APC conjugate and DAPI, 1) an Annexin-V-APC conjugate; or 3) DAPI. An unstained aliquot was also set up as a negative control to define the basal level of apoptotic and dead cells. The percentage of cells that have been induced to undergo apoptosis is then determined by subtracting the percentage of apoptotic cells in the unstained aliquot from percentage of apoptotic cells in the stained aliquot. After staining, cells were washed in ice-cold PBS and resuspended in 300 μL of the Annexin V buffered solution, and analysis by flow cytometry using an LSR II flow cytometer (BD Bioscience, CA). Cells that were Annexin V negative and DAPI negative are considered healthy, cells, Annexin V positive and DAPI negative cells are considered apoptotic, and cells that are positive to both Annexin V and DAPI are considered necrotic. Mean cell numbers between the OST-01 treated and control group was statistically analyzed by using unpaired, two-tailed Student's t test, with values from at least two independent experiments with triplicate determination. Data are presented as mean±standard error (SE) and a $p<0.05$ was considered statistically significant.

As shown in FIG. 24B, results from the apoptosis flow cytometry assay demonstrated that treatment with Fraction 12, Fraction 13, and Fraction 14 each exhibited in a statistically significant increase in Annexin V positive cells as compared to the negative controls. FIG. 24A shows that the three fractions were retained from between 18 minutes to 22 minutes. For example, MV-4-11 cells treated with 0.5 μL/mL of Fraction 12 showed at least a 16-fold increase in Annexin V positive cells relative to cells treated with the negative control, whereas MV-4-11 cells treated with 1 μL/mL of Fraction 12 showed at least a 10-fold increase in Annexin V positive cells relative to cells treated with the negative control. In addition, the 1 μL/mL concentration of Fraction 12 exhibited about 60% the activity of the 1 μL/mL concentration of OST-01. Similarly, MV-4-11 cells treated with 0.5 μL/mL of Fraction 13 showed at least a 11-fold increase in Annexin V positive cells relative to cells treated with the negative control, whereas MV-4-11 cells treated with 1 μL/mL of Fraction 13 showed at least a 15-fold increase in Annexin V positive cells relative to cells treated with the negative control. In addition, the 1 μL/mL concentration of Fraction 13 exhibited about 90% the activity of the 1 μL/mL concentration of OST-01. Likewise, MV-4-11 cells treated with 0.5 μL/mL of Fraction 14 showed at least a 5-fold increase in Annexin V positive cells relative to cells treated with the negative control, whereas MV-4-11 cells treated with 1 μL/mL of Fraction 14 showed at least a 11-fold increase in Annexin V positive cells relative to cells treated with the negative control. In addition, the 1 μL/mL concentration of Fraction 14 exhibited about 65% the activity of the 1 μL/mL concentration of OST-01. The results from the apoptosis flow cytometry assay demonstrated that treatment Fractions 12-14 significantly increased the number of cells undergoing apoptosis in an AML cell line, demonstrating that an anti-oncogenic component present in OST-01 is present in these fractions.

In another series of experiments, the findings were confirmed and extended by repeating apoptosis flow cytometry in MV-4-11 AML cancer cells and further testing the anti-oncogenic efficacy of Fractions 12-14 on THP-1 and HL-60 AML cancer cells. A HL-60 cell line (CRL-240) was obtained from the American Type Culture Collection (ATCC). HL-60 cells have lymphoblast morphology and are promyeoloblasts isolated from peripheral blood of a 36-year-old human female subject diagnosed with acute promyelocytic leukemia. Fractions were separated and collecting using the UV-RPHPLC procedure essentially described above and each fraction was tested for antioncogenic activity using an apoptosis flow cytometry assay essentially as described above.

Figure 25A:
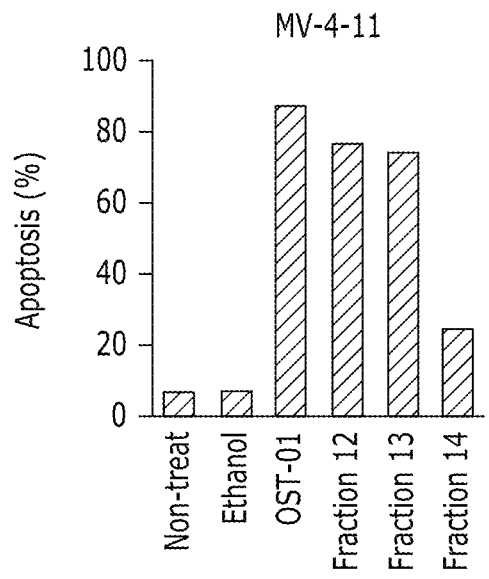
FIGS. 25A-25C show bar graphs of cells stained with Annexin V obtained from apoptosis flow cytometry assays with FIG. 25A showing the results of MV-4-11 cells treated with HPLC fractions of OST-01 containing anti-oncogenic activity.
Figure 25B:
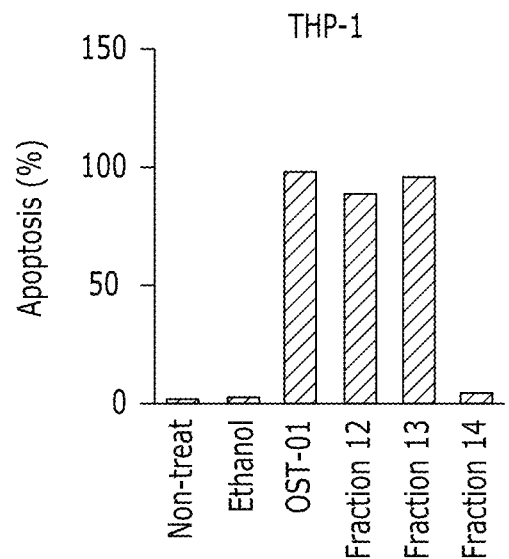
Figure 25C:
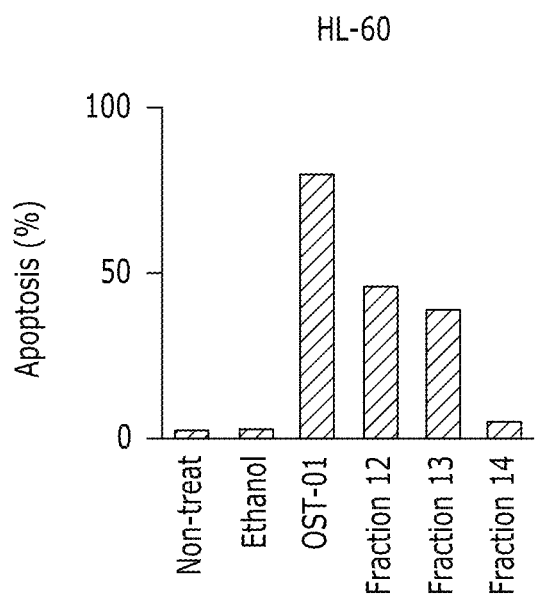

As shown in FIGS. 25A-25C, results from the apoptosis flow cytometry assay demonstrated that treatment with Fraction 12, Fraction 13, and Fraction 14 each exhibited in a statistically significant increase in Annexin V positive cells as compared to the negative controls in all three AML cell lines tested. For example, as shown in FIG. 25A, MV-4-11 cells treated with 1) 1 μL/mL of Fraction 12 showed at least a 15-fold increase in Annexin V positive cells relative to cells treated with the negative control; 2) 1 μL/mL of Fraction 13 showed at least a 15-fold increase in Annexin V positive cells relative to cells treated with the negative control; and 3) 1) 1 μL/mL of Fraction 14 showed at least a 5-fold increase in Annexin V positive cells relative to cells treated with the negative control. In addition, the 1 μL/mL concentration of Fraction 12 exhibited about 90% the activity of the 1 μL/mL concentration of OST-01, while the 1 μL/mL concentration of Fraction 13 exhibited about 85% the activity of the 1 μL/mL concentration of OST-01, and the 1 μL/mL concentration of Fraction 14 exhibited about 30% the activity of the 1 μL/mL concentration of OST-01. Similarly, as shown in FIG. 25B, THP-1 cells treated with 1) 1 μL/mL of Fraction 12 showed at least a 20-fold increase in Annexin V positive cells relative to cells treated with the negative control; 2) 1 μL/mL of Fraction 13 showed at least a 20-fold increase in Annexin V positive cells relative to cells treated with the negative control; and 3) 1) 1 μL/mL of Fraction 14 showed at least a 3-fold increase in Annexin V positive cells relative to cells treated with the negative control. In addition, the 1 μL/mL concentration of Fraction 12 exhibited about 95% the activity of the 1 μL/mL concentration of OST-01, while the 1 μL/mL concentration of Fraction 13 exhibited about 100% the activity of the 1 μL/mL concentration of OST-01, and the 1 μL/mL concentration of Fraction 14 exhibited about 5% the activity of the 1 μL/mL concentration of OST-01. Likewise, as shown in FIG. 25C, HL-60 cells treated with 1) 1 μL/mL of Fraction 12 showed at least a 9-fold increase in Annexin V positive cells relative to cells treated with the negative control; 2) 1 μL/mL of Fraction 13 showed at least a 8-fold increase in Annexin V positive cells relative to cells treated with the negative control; and 3) 1) 1 μL/mL of Fraction 14 showed at least a 2-fold increase in Annexin V positive cells relative to cells treated with the negative control. In addition, the 1 μL/mL concentration of Fraction 12 exhibited about 60% the activity of the 1 μL/mL concentration of OST-01, while the 1 μL/mL concentration of Fraction 13 exhibited about 55% the activity of the 1 μL/mL concentration of OST-01, and the 1 μL/mL concentration of Fraction 14 exhibited about 10% the activity of the 1 µL/mL concentration of OST-01. Taken together, the results from the apoptosis flow cytometry assay demonstrated that the anti-oncogenic activity of OST-01 is primarily contained within Fraction 12 and Fraction 13 and the antioncogenic component contained within these fractions is a significant component of the antioncogenic activity observed for OST-01.

To identify the chemical composition of the antioncogenic component present in OST-01, fractions 12-14 were subjected to Liquid Chromatography-Mass Spectrometry/Mass Spectrometry (LC-MS/MS) as well as Direct Infusion MS (DI-MS) analyses to obtain spectral information on the components contained in these fractions. Raw data obtained from these analyses were searched against a natural product databases, a flavonoid database, and other chemspider databases centered to plant natural products for putative identification. IN addition, based on the most abundant precursor ions detected in DI-MS, compounds were manually searched to assign putative identify of the abundant compounds. These analyses identified seven potential candidates for the antioncogenic compound present in Fractions 12-14. Potential candidates were synthesized and tested for antioncogenic activity using an apoptosis flow cytometry assay essentially as described above.

Figure 26A:
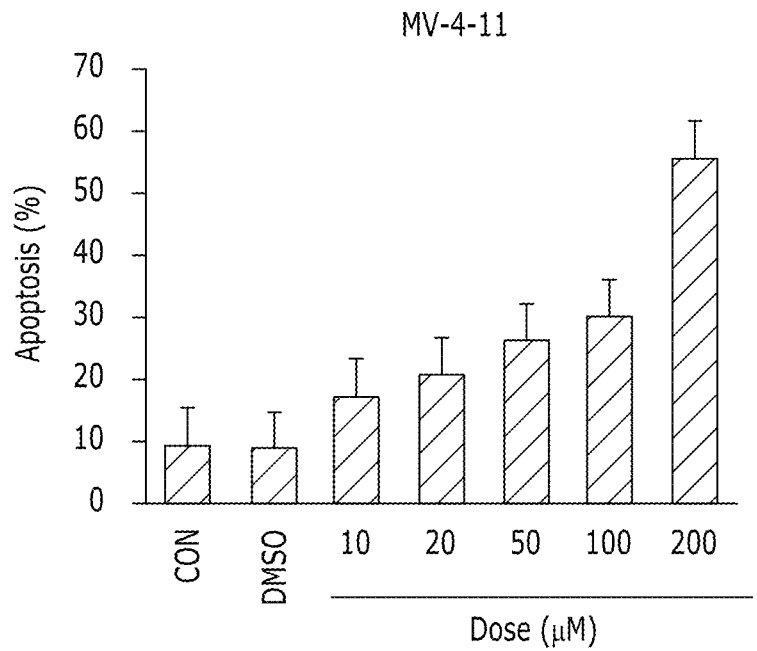
FIGS. 26A-26B show bar graphs of cells stained with Annexin V obtained from apoptosis flow cytometry assays with FIG. 26A showing the results of MV-4-11 cells treated with an escalating dose of (2E)-21-Hydroxy-2-henicosenoic acid.
Figure 26B:
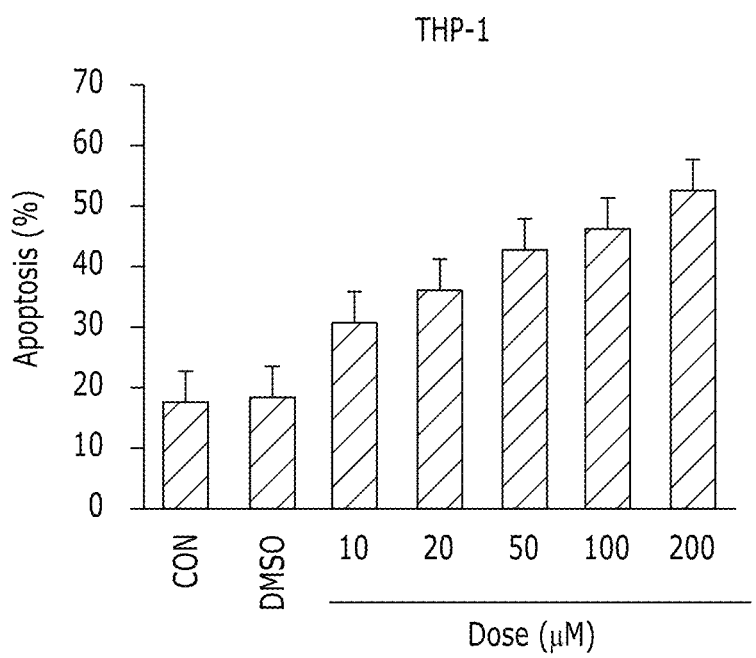

As shown in FIGS. 26A-26B, results from the apoptosis flow cytometry assay demonstrated that treatment with one of the synthesized compounds, (2E)-21-Hydroxy-2-henicosenoic acid, showed a dose-dependent increase in Annexin V positive cells as compared to the negative controls in the two AML cell lines tested. For example, as shown in FIG. 26A, MV-4-11 cells treated with (2E)-21-Hydroxy-2-henicosenoic acid exhibited a dose-dependent increase in Annexin V positive cells relative to cells treated with the ethanol or DMSO negative controls, and reached at least a 55% increase in Annexin V positive cells at the highest amount tested (200 µM). Similarly, as shown in FIG. 26B, THP-1 cells treated with (2E)-21-Hydroxy-2-henicosenoic acid exhibited a dose-dependent increase in Annexin V positive cells relative to cells treated with the ethanol or DMSO negative controls, and reached at least a 50% increase in Annexin V positive cells at the highest amount tested (200 µM). Taken together, the results from the apoptosis flow cytometry assay demonstrated that (2E)-21-Hydroxy-2-henicosenoic acid showed a dose-dependent inhibition of apoptosis, thereby demonstrating that this compound is a significant component of the antioncogenic activity observed for OST-01.

To further explore the antioncogenic activity of (2E)-21-Hydroxy-2-henicosenoic acid, a derivative of this compound, 21-Hydroxyhenicosenoic acid was also tested for antioncogenic activity using an apoptosis flow cytometry assay essentially as described above.

Figure 27A:
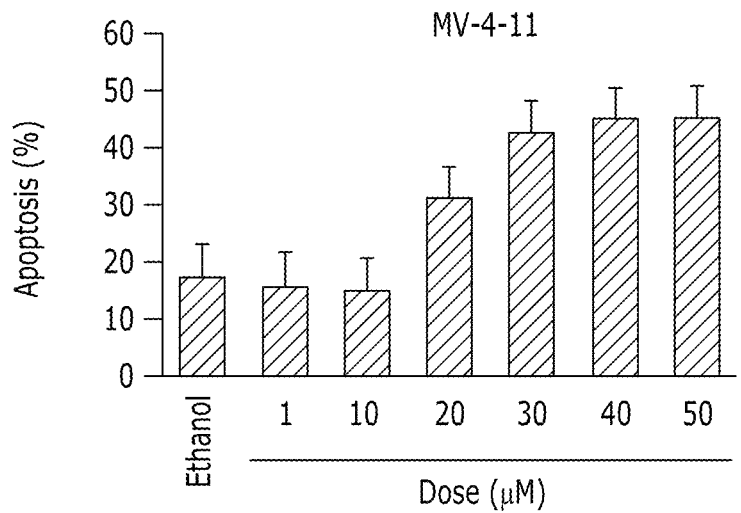
FIGS. 27A-27B show bar graphs of cells stained with Annexin V obtained from apoptosis flow cytometry assays with FIG. 27A showing the results of MV-4-11 cells treated with an escalating dose of 21-Hydroxyhenicosenoic acid.
Figure 27B:
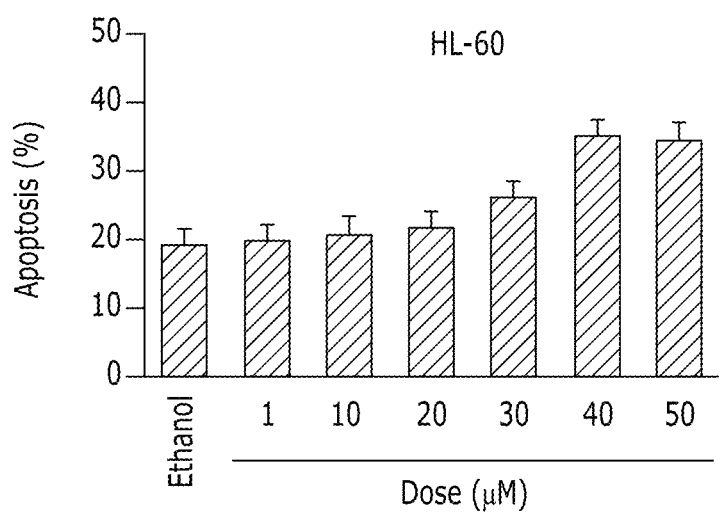

As shown in FIGS. 27A-27B, results from the apoptosis flow cytometry assay demonstrated that treatment with 21-Hydroxyhenicosenoic acid showed a dose-dependent increase in apoptosis as compared to the negative controls in the two AML cell lines tested. For example, as shown in FIG. 27A, MV-4-11 cells treated with (2E)-21-Hydroxy-2-henicosenoic acid exhibited a dose-dependent increase in Annexin V positive cells relative to cells treated with the ethanol negative control, and reached an over 2-fold increase in Annexin V positive cells at the highest amount tested (50 µM). Similarly, as shown in FIG. 27B, HL-60 cells treated with 21-Hydroxyhenicosenoic acid exhibited a dose-dependent increase in Annexin V positive cells relative to cells treated with the ethanol or DMSO negative controls, and reached an over 1.5-fold increase in Annexin V positive cells at the highest amount tested (50 µM). Taken together, the results from the apoptosis flow cytometry assay demonstrated that, like (2E)-21-Hydroxy-2-henicosenoic acid, 21-Hydroxyhenicosenoic acid also showed a dose-dependent inhibition of apoptosis, thereby demonstrating that this compound also has antioncogenic activity.

Figure 28A:
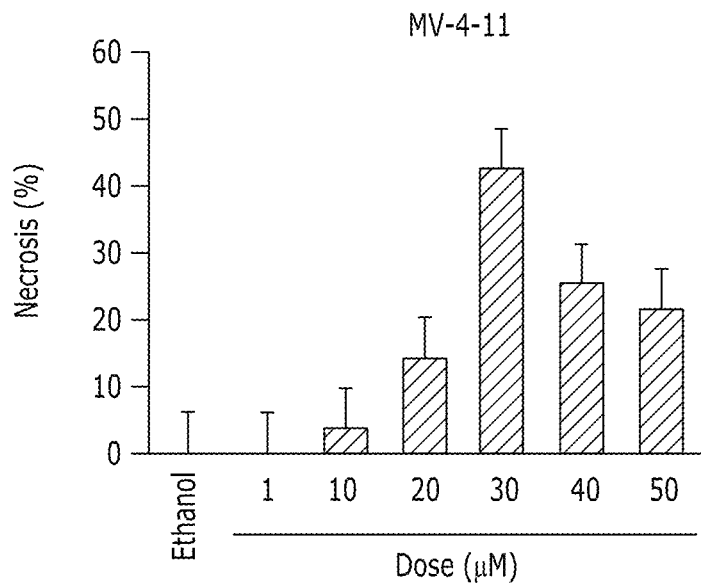
FIGS. 28A-28B show bar graphs of cells stained with DAPI obtained from apoptosis flow cytometry assays with FIG. 28A showing the results of MV-4-11 cells treated with an escalating dose of 21-Hydroxyhenicosenoic acid.
Figure 28B:
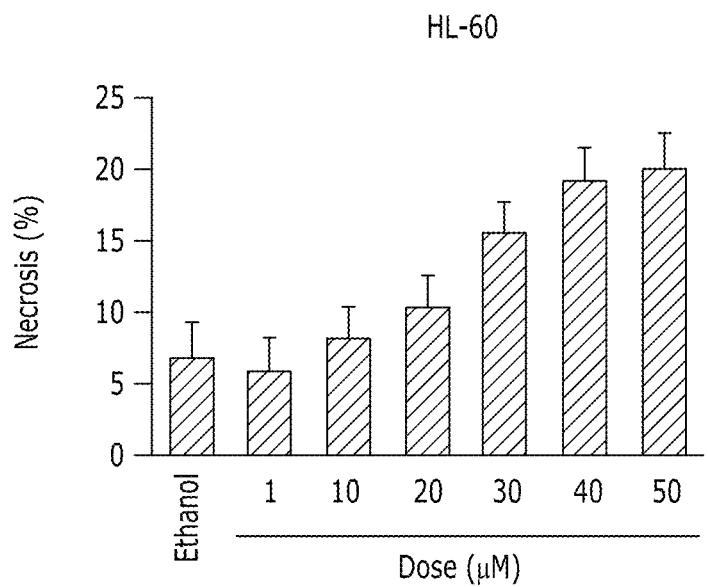

Additionally, as shown in FIGS. 28A-28B, results from the apoptosis flow cytometry assay demonstrated that treatment with 21-Hydroxyhenicosenoic acid showed a dose-dependent increase in cell necrosis as compared to the negative controls in the two AML cell lines tested. For example, as shown in FIG. 28A, MV-4-11 cells treated with (2E)-21-Hydroxy-2-henicosenoic acid exhibited a dose-dependent increase in DAPI positive cells relative to cells treated with the ethanol negative control up to the 30 µM of 21-Hydroxyhenicosenoic acid, and reached at least an 8-fold increase in DAPI positive cells, before a decline in DAPI positive cells was observed at higher concentrations. The decline in necrosis at these higher concentrations was due to the fact that cellular degradation was so extensive, the resulting cellular fragments became undetectable during flow cytometry analysis. As shown in FIG. 28B, HL-60 cells treated with 21-Hydroxyhenicosenoic acid exhibited a dose-dependent increase in DAPI positive cells relative to cells treated with the ethanol negative control, and reached an over 4-fold increase in DAPI positive cells at the highest amount tested (50 µM). Taken together, the results from the apoptosis flow cytometry assay demonstrated that 21-Hydroxyhenicosenoic acid showed a dose-dependent increase in cellular necrosis, thereby demonstrating that this compound also has antioncogenic activity.

In closing, foregoing descriptions of embodiments of the present invention have been presented for the purposes of illustration and description. It is to be understood that, although aspects of the present invention are highlighted by referring to specific embodiments, one skilled in the art will readily appreciate that these described embodiments are only illustrative of the principles comprising the present invention and such examples are not limiting thereto. As such, the specific embodiments are not intended to be exhaustive or to limit the invention to the precise forms disclosed. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

In addition, groupings of alternative embodiments, elements, steps and/or limitations of the present invention are not to be construed as limitations. Each such grouping may be referred to and claimed individually or in any combination with other groupings disclosed herein. It is anticipated that one or more alternative embodiments, elements, steps and/or limitations of a grouping may be included in, or deleted from, the grouping for reasons of convenience and/or patentability. When any such inclusion or deletion occurs, the specification is deemed to contain the grouping as modified, thus fulfilling the written description of all Markush groups used in the appended claims. In addition, all methods described herein can be performed in any suitable order unless otherwise indicated herein or otherwise clearly contradicted by context. Therefore, it should be understood that embodiments of the disclosed subject matter are in no way limited to a particular element, compound, composition, component, article, apparatus, methodology, use, protocol, step, and/or limitation described herein, unless expressly stated as such.

While aspects of the invention have been described with reference to at least one exemplary embodiment, it is to be clearly understood by those skilled in the art that the invention is not limited thereto. Furthermore, those of ordinary skill in the art will recognize that certain changes, modifications, permutations, alterations, additions, subtractions, and sub-combinations thereof can be made in accordance with the teachings herein without departing from the spirit of the present invention. It is intended that the following appended claims and claims hereafter introduced are interpreted to include all such changes, modifications, permutations, alterations, additions, subtractions, and sub-combinations as are within their true spirit and scope. Accordingly, the scope of the present invention is not to be limited to that precisely as shown and described by this specification. Rather, the scope of the invention is to be interpreted only in conjunction with the appended claims and it is made clear, here, that the inventor(s) believe that the claimed subject matter is the invention.

Certain embodiments of the present invention are described herein, including the best mode known to the inventors for conducting the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

The words, language, and terminology used in this specification is for the purpose of describing particular embodiments, elements, steps and/or limitations only and is not intended to limit the scope of the present invention, which is defined solely by the claims. In addition, such words, language, and terminology are to be understood not only in the sense of their commonly defined meanings, but to include by special definition in this specification structure, material or acts beyond the scope of the commonly defined meanings. Thus, if an element, step or limitation can be understood in the context of this specification as including more than one meaning, then its use in a claim must be understood as being generic to all possible meanings supported by the specification and by the word itself.

The definitions and meanings of the elements, steps or limitations recited in a claim set forth below are, therefore, defined in this specification to include not only the combination of elements, steps or limitations which are literally set forth, but all equivalent structure, material or acts for performing substantially the same function in substantially the same way to obtain substantially the same result. In this sense it is therefore contemplated that an equivalent substitution of two or more elements, steps and/or limitations may be made for any one of the elements, steps or limitations in a claim set forth below or that a single element, step, or limitation may be substituted for two or more elements, steps and/or limitations in such a claim. Although elements, steps or limitations may be described above as acting in certain combinations and even initially claimed as such, it is to be expressly understood that one or more elements, steps and/or limitations from a claimed combination can in some cases be excised from the combination and that the claimed combination may be directed to a sub-combination or variation of a sub-combination. As such, notwithstanding the fact that the elements, steps and/or limitations of a claim are set forth below in a certain combination, it must be expressly understood that the invention includes other combinations of fewer, more, or different elements, steps and/or limitations, which are disclosed in above combination even when not initially claimed in such combinations. Furthermore, insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. Accordingly, the claims are thus to be understood to include what is specifically illustrated and described above, what is conceptually equivalent, what can be obviously substituted and also what essentially incorporates the essential idea of the invention.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, all lists of values should be considered as inclusive of intermediate values unless the context indicates the contrary.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a comparable manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc.—for identified elements are used to distinguish between the elements, and do not indicate or imply a required or limited number of such elements, and do not indicate a particular position or order of such elements unless otherwise specifically stated.

When used in the claims, whether as filed or added per amendment, the open-ended transitional term "comprising", variations thereof such as, e.g., "comprise" and "comprises", and equivalent open-ended transitional phrases thereof like "including", "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement, and support for the phrases "consisting essentially of" and "consisting of."

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

Any claims intended to be treated under 35 U.S.C. § 112(f) will begin with the words "means for," but use of the term "for" in any other context is not intended to invoke treatment under 35 U.S.C. § 112(f). Accordingly, Applicant reserves the right to pursue additional claims after filing this application, in either this application or in a continuing application.

It should be understood that the methods and the order in which the respective elements of each method are performed are purely exemplary. Depending on the implementation, they may be performed in any order or in parallel, unless indicated otherwise in the present disclosure.

Finally, all patents, patent publications, and other references cited and identified in the present specification are individually and expressly incorporated herein by reference in their entirety to the same extent as if each individual publication or patent application were specifically and individually indicated to be incorporated by reference. These publications are provided solely for their disclosure prior to the filing date of the present application. The reference to any prior art in this specification is not, and should not be taken as, an acknowledgement or any form of suggestion that the prior art forms part of the common general knowledge from any country. In addition, where a definition or use of a term in an incorporated reference is inconsistent or contrary to the definition of that term provided herein, the definition of that term provided herein applies and the definition of that term in the reference does not apply. Lastly, nothing in this regard is or should be construed as an admission that the inventors are not entitled to antedate such disclosure by virtue of prior invention or for any other reason. All statements as to the date or representation as to the contents of these documents are based on the information available to the applicant and do not constitute any admission as to the correctness of the dates or contents of these documents.

The invention claimed is:

1. A pharmaceutical composition comprising:
   (i) 70% to 99% of a solvent comprising a pharmaceutically acceptable monohydric alcohol selected from the group consisting of ethanol, n-propanol, isopropanol, isobutanol, and 2-methyl-2-butanol, or any combination thereof; and
   (ii) one or more anti-oncogenic phytochemicals comprising one or more compounds of the chemical formula

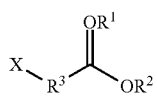
(I)

or a stereoisomer thereof,
wherein:
X is OH, OCH$_3$, or OCH$_2$CH$_3$;
R$^1$ is absent;
R$^2$ is H, CH$_3$, or CH$_2$CH$_3$; and
R$^3$ is:

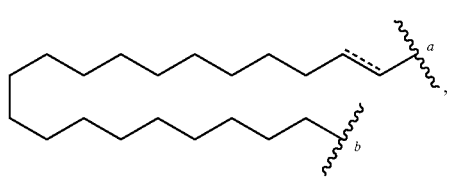

or a stereoisomer thereof,
wherein:
⸺ is a single bond or a double bond; and
a is bonded to C(OR$^1$)OR$^2$ and b is bonded to X;
and
wherein the pharmaceutical composition is produced by a method comprising the following steps:
(a) preparing a macerate comprising a plant material from *Baccharis coridifolia* and a solvent comprising 70% to 100% of the pharmaceutically acceptable monohydric alcohol;
wherein the pharmaceutically acceptable monohydric alcohol is selected from the group consisting of ethanol, n-propanol, isopropanol, isobutanol, and 2-methyl-2-butanol, or any combination thereof;
(b) incubating the macerate prepared in step (a) above in a closed, light-tight container at a temperature in the range of 15° C. to 22° C. over a period of at least 21 days, in order to solubilize the one or more anti-oncogenic phytochemicals comprising the one or more compounds of the chemical formula (I) above; and
(c) purifying the macerate incubated in step (b) above, in order to remove any solid plant material and produce an extract comprising the pharmaceutical composition above comprising:
(i) 70% to 99% of a solvent comprising a pharmaceutically acceptable monohydric alcohol selected from the group consisting of ethanol, n-propanol, isopropanol, isobutanol, and 2-methyl-2-butanol, or any combination thereof; and
(ii) one or more anti-oncogenic phytochemicals comprising one or more compounds of the chemical formula (I):

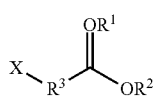
(I)

or a stereoisomer thereof,
wherein:
X is OH, OCH$_3$, or OCH$_2$CH$_3$;
R$^1$ is absent;
R$^2$ is H, CH$_3$, or CH$_2$CH$_3$; and
R$^3$ is:

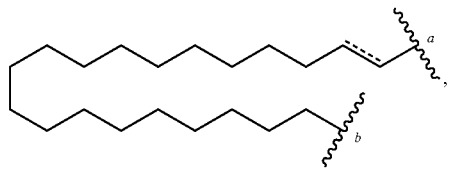

or a stereoisomer thereof,
wherein:
⸺ is a single bond or a double bond; and
a is bonded to C(OR$^1$)OR$^2$ and b is bonded to X.

2. The pharmaceutical composition of claim 1, wherein the pharmaceutical composition comprises 70% to 99% of a solvent comprising a pharmaceutically acceptable monohydric alcohol selected from the group consisting of ethanol, n-propanol, and isopropanol, or any combination thereof.

3. The pharmaceutical composition of claim 2, wherein the pharmaceutical composition comprises 70% to 99% of ethanol.

4. The pharmaceutical composition of claim 1, wherein the pharmaceutical composition is produced by a method comprising:
(a) preparing a macerate comprising a plant material from *Baccharis coridifolia*, wherein the plant material from *Baccharis coridifolia* comprises leaves.

5. The pharmaceutical composition of claim 1, wherein the pharmaceutical composition is produced by a method comprising:
(a) preparing a macerate comprising a solvent comprising 85% to 100% of the pharmaceutically acceptable monohydric alcohol.

6. The pharmaceutical composition of claim 5, wherein the solvent comprises 85% to 95% of the pharmaceutically acceptable monohydric alcohol.

7. The pharmaceutical composition of claim 6, wherein the solvent comprises 88% to 92% of the pharmaceutically acceptable monohydric alcohol.

8. The pharmaceutical composition of claim 1, wherein the pharmaceutical composition is produced by a method comprising:
(a) preparing a macerate comprising a ratio (g/L) of plant material from *Baccharis coridifolia* to solvent comprising 70% to 100% of the pharmaceutically acceptable monohydric alcohol in the range of 10:100 g/L to 40:100 g/L of plant material to solvent.

9. The pharmaceutical composition of claim 8, wherein the macerate comprises a ratio (g/L) of plant material to solvent in the range of 15:100 g/L to 35:100 g/L of plant material to solvent.

10. The pharmaceutical composition of claim 9, wherein the macerate comprises a ratio (g/L) of plant material to solvent in the range of 20:100 g/L to 30:100 g/L of plant material to solvent.

11. The pharmaceutical composition of claim 1, wherein the pharmaceutical composition is produced by a method comprising:
(b) incubating the macerate prepared in step (a) above in a closed, light-tight container at a temperature in the range of 15° C. to 22° C. over a period of at least 28 days, in order to solubilize the one or more anti-oncogenic phytochemicals comprising the one or more compounds of the chemical formula (I) above.

12. The pharmaceutical composition of claim 1, wherein incubating the macerate is performed over a period of at least 35 days.

13. The pharmaceutical composition of claim 1, wherein the pharmaceutical composition is produced by a method comprising:
   (b) incubating the macerate prepared in step (a) above in a closed, light-tight container at a temperature in the range of 15° C. to 22° C. over a period in the range of 21 days to 35 days, in order to solubilize the one or more anti-oncogenic phytochemicals comprising the one or more compounds of the chemical formula (I) above.

14. The pharmaceutical composition of claim 1, wherein the pharmaceutical composition is produced by a method comprising:
   (c) filtering the macerate incubated in step (b) above one or more times, in order to remove any solid plant material and produce an extract comprising the pharmaceutical composition above comprising:
      (i) 70% to 99% of a solvent comprising a pharmaceutically acceptable monohydric alcohol selected from the group consisting of ethanol, n-propanol, isopropanol, isobutanol, and 2-methyl-2-butanol, or any combination thereof; and
      (ii) one or more anti-oncogenic phytochemicals comprising one or more compounds of the chemical formula (I) above.

15. The pharmaceutical composition of claim 1, wherein the pharmaceutical composition comprises one or more anti-oncogenic phytochemicals comprising one or more compounds of the chemical formula (II);

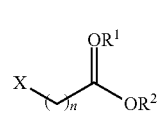

(II)

wherein:
   X is OH or OCH$_3$; and
   n is 20.

16. The pharmaceutical composition of claim 15, wherein X is OH.

17. The pharmaceutical composition of claim 1, wherein the pharmaceutical composition comprises one or more anti-oncogenic phytochemicals comprising one or more compounds of the chemical formula (I), wherein R$^3$ is:

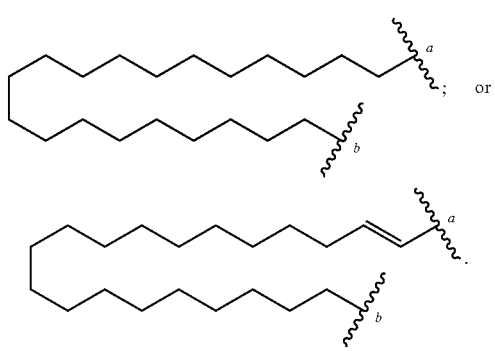

18. The pharmaceutical composition of claim 1, wherein the pharmaceutical composition comprises one or more anti-oncogenic phytochemicals comprising one or more compounds of the chemical formula (I), wherein R$^3$ is:

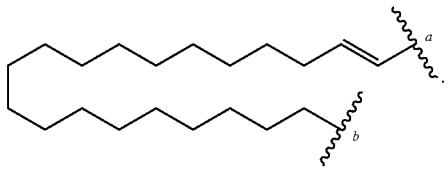

19. The pharmaceutical composition of claim 1, wherein the pharmaceutical composition comprises one or more anti-oncogenic phytochemicals comprising one or more compounds of the chemical formula (I), wherein:
   (i) R$^2$ is H; and
      R$^3$ is:

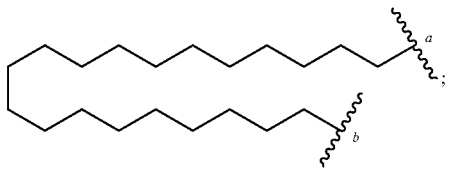 [SMILES: *CCCCCCCCCCCCCCCCCCCC*]

or
   (ii) R$^2$ is H; and
      R$^3$ is:

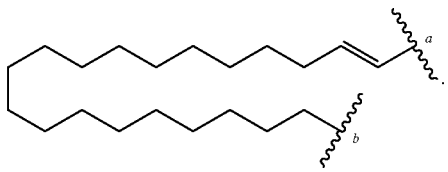 [SMILES: */C=C/CCCCCCCCCCCCCCCCCC*]

20. The pharmaceutical composition of claim 1, wherein the pharmaceutical composition comprises one or more anti-oncogenic phytochemicals comprising one or more compounds of the chemical formula (I) selected from the group consisting of:

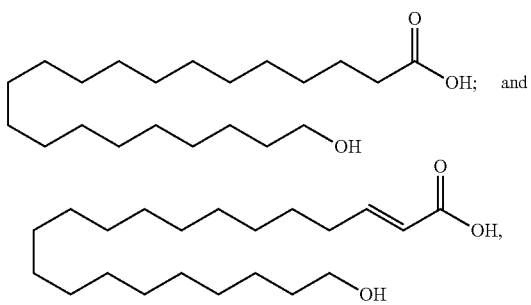

or a stereoisomer thereof.

* * * * *